United States Patent
Basler et al.

(10) Patent No.: US 7,375,075 B2
(45) Date of Patent: *May 20, 2008

(54) ESSENTIAL DOWNSTREAM COMPONENT OF THE WINGLESS SIGNALING PATHWAY AND THERAPEUTIC AND DIAGNOSTIC APPLICATIONS BASED THEREON

(75) Inventors: Konrad Basler, Zürich (CH); Erich Brunner, Zürich (CH); Barbara Froesch, Zürich (CH); Thomas Kramps, Zürich (CH); Oliver Peter, Zürich (CH)

(73) Assignee: Universitat Zürich, Zurich (CH)

( * ) Notice: Subject to any disclaimer, the term of this patent is extended or adjusted under 35 U.S.C. 154(b) by 425 days.

This patent is subject to a terminal disclaimer.

(21) Appl. No.: 10/664,859

(22) Filed: Sep. 22, 2003

(65) Prior Publication Data
US 2004/0038901 A1    Feb. 26, 2004

Related U.S. Application Data

(62) Division of application No. 09/915,543, filed on Jul. 27, 2001, now Pat. No. 7,049,290.

(60) Provisional application No. 60/221,502, filed on Jul. 28, 2000.

(51) Int. Cl.
*C07K 14/00* (2006.01)
(52) U.S. Cl. .......................................... 514/2; 530/350
(58) Field of Classification Search ................ 530/350; 514/12
See application file for complete search history.

(56) References Cited

U.S. PATENT DOCUMENTS

2005/0208558 A1 * 9/2005 Venter et al. .................. 435/6

FOREIGN PATENT DOCUMENTS

WO        WO 01/57188        8/2001

* cited by examiner

*Primary Examiner*—Karen Cochrane Carlson
(74) *Attorney, Agent, or Firm*—Sughrue Mion Pllc.

(57) ABSTRACT

An isolated polypeptide comprising a peptide which consists of a legless homology domain (HD); wherein the peptide inhibits Lgs function in colon cancer cells; and a composition comprising the same, are disclosed.

9 Claims, 32 Drawing Sheets
(2 of 32 Drawing Sheet(s) Filed in Color)

wild type     sev-wg     sev-wg, lgs$^{317}$/+

FIG. 2A

| | |
|---|---|
| ACGAGTGCTTCTCTTATTATGCGAGCTGTTTATTCCAAAGTATGTTCGCAATTTTCGACT | 60 |
| CCTGCTAACATAACGCACGGTTAAAGCAGGAACATTTGGGCCTATAAGCCCAAAATTTCA | 120 |
| TTAGCTTAATACGATGCTCCGAAGTGTTATTGCATTTGCACATATACATAAAATTGTGAC | 180 |
| ATAGAATAGGAGAATTCCACATACAAATACAAAAATACAAAATCCTCCAGTAAAATTTAA | 240 |
| AACGATATCGTGTTTTGCTTCGCGTATCTCACGTGAGATGTAATCGCATGCATATGAGTG | 300 |
| GTGAGTGCCTGCGTGCAGTTCCTGGTCTAAATATGCTTAATTGCGTTCGCCGACTTCAAA | 360 |
| AGCAATAAAACGATGGATTTTAATTGCTACTTGAGCAATTAGCCACACAAGGGATCTTGG | 420 |

| | | |
|---|---|---|
| GAAGGTCGATTTGAAGGAATTCGATTTCTAGGATGCTCTCGACAACAATGCCCCGCAGTC | | 480 |
| | M P R S P | 5 |
| CAACCCAACAACAGCCGCAACCAAACTCCGATGCCTCCTCAACAAGTGCATCTGGATCAA | | 540 |
| T Q Q Q P Q P N S D A S S T S A S G S N | | 25 |
| ATCCTGGAGCAGCGATCGGAAATGGGGACTCGGCGGCGAGCAGAAGTTCTCCGAAGACCC | | 600 |
| P G A A I G N G D S A A S R S S P K T L | | 45 |
| TTAATAGCGAACCCTTTTCTACTTTGTCGCCGGGTAAGACTTGTATTGATTTCTCTTTGT | | 660 |
| N S E P F S T L S P | | 55 |
| CCGGAATTATAACAACTTTCTGTGTTTCCAGATCAAATAAAATTGACGCCAGAAGAAGGC | | 720 |
| D Q I K L T P E E G | | 65 |
| ACTGAGAAAAGCGGACTATCAACTAGTGATAAAGCTGCCACTGGAGGAGCCCCAGGCAGT | | 780 |
| T E K S G L S T S D K A A T G G A P G S | | 85 |
| GGAAATAATCTGCCCGAGGGACAAACTATGCTAAGGCAGAACTCTACGAGCACAATCAAC | | 840 |
| G N N L P E G Q T M L R Q N S T S T I N | | 105 |
| TCGTGCCTAGTCGCTTCTCCACAAAACTCCAGTGAACACTCGAATAGCAGCAATGTGTCT | | 900 |
| S C L V A S P Q N S S E H S N S S N V S | | 125 |
| GCTACAGTGGGCCTTACTCAGATGGTAGATTGTGACGAGCAATCGAAGAAAAACAAATGT | | 960 |
| A T V G L T Q M V D C D E Q S K K N K C | | 145 |
| AGTGTGAAGGACGAGGAAGCTGGTAAGACTGCCCTACAAATGGTTTAAAATTTTAAAATG | | 1020 |
| S V K D E E A | | 152 |
| TATTGGCGTTCACCTTTGTTAATCATTTAATTGTTTTTTTTTGCTATACTTACAATTTT | | 1080 |
| AGTTTTAAACTTGTAAACTTGACTAAAACTCGCGAAGCTCGGATCAAAACAGACATTTTC | | 1140 |
| TTGGAACCGTAATTAAGCTCATAAAAATATTAATTCATCTTGATGGAATGCATATCATAG | | 1200 |

FIG. 2B

```
ATGTACTCAAACATCTCAAGAAAGACCTCAAATTGGATCAACTAATTAGTTTGAGAAAAA    1260

ATTGCTGTACTTTTAAGAATATATTAATTTAAAAATTTGCTGAGTGAAATGATATAATAG    1320

TCACAATAATTTTTAGTTAAACTGCTAAAGCATTTTGAATAGCCGTGCTACGCAGATGCT    1380

ACTAGACGCGGTGTAAAAGCTAATTTTTATTTAAAAGCTGTCCTAATATTCCATAACCAT    1440

TAATGTCCCATTTCAGAAATAAGTTCTAATAAAGCAAAAGGTCAAGCAGCTGGTGGCGGC    1500
            E   I   S   S   N   K   A   K   G   Q   A   A   G   G   G         167

TGCGAAACAGGTTCTACATCCAGTTTGACTGTCAAGGAAGAACCCACCGATGTCTTAGGC    1560
 C   E   T   G   S   T   S   S   L   T   V   K   E   E   P   T   D   V   L   G     187

AGTTTAGTAAATATGAAAAAGAAGAAAGAGAAAATCATTCGCCAACGATGTCCCCTGTT    1620
 S   L   V   N   M   K   K   E   E   R   E   N   H   S   P   T   M   S   P   V     207

GGTTTTGGTTCAATTGGTAATGCACAGGACAACTCCGCTACACCGGGTAAGTTTTAAGAG    1680
 G   F   G   S   I   G   N   A   Q   D   N   S   A   T   P                         222

ATCCATATAAAGCAAATAACAAGAATTAATGTCAGTTACCAATTTTATTTGATAGTCAAA    1740

GAACTACTATAGCGATATCTCCTGCCTTTTAATTTTATTTTAATTAGGAAATACGAATAT    1800

TTCTAATTTGTAAAATAAAATTGATTAATTAACTAGAATTTAAAAACCTTTTGAATTAGG    1860

ACATACCCTTCCAAAAATCAGTAATCATTGGGAACGAGAGTGTGGTCCCGAAGGAGACTA    1920

CTATAAAACCTTTTGAGCTATCTGATACTGCACGCTACTAAAAATGATTAGTTTAGGAAA    1980

ATGGGTGTAATTTTGTAGGAAGTTTTCATTTTAGAAGAAATGTGATTATTTTATTAAACC    2040

CCTTCAAGCGGAACTACATTTGTTCTACGATATTTTGGAAAAACAAATGGTTAAGTTGGA    2100

AAGTGCCTATAAAACAGAATTCCACGGTTTCAAATACTAACCAGGTTTTTGATTTAATTT    2160

TGATTAAATGAGAAATTATCACACTTCAGTTAAAATGTTTAATTCGATTAAGGTCGGACA    2220

ATCACAGCAGATTTCCATTTTTGCGTGTATATATAGAAGTCGCCTTCACACTCTTCTGGC    2280

GCGCTTCACCACTACGTGGAGTTCCGCCCGCAGTGATTTATATAGATGATTTACGAGTTA    2340

TTTAATTTTTTATGGTGTATTTTAATAAATATCTTATTTATTCATTTTACATAGTTAAAA    2400
                                                              V   K   I         225

TTGAAAGAATTTCAAACGACAGTACCACGGAAAAAAAAGGATCGTCCTTGACAATGAATA    2460
 E   R   I   S   N   D   S   T   T   E   K   K   G   S·  S   L   T   M   N   N     245

ATGACGAAATGAGCATGGAAGGCTGCAATCAGTTGAATCCCGATTTTATCAATGAATCTT    2520
 D   E   M   S   M   E   G   C   N   Q   L   N   P   D   F   I   N   E   S   L     265
```

FIG. 2C

```
TAAATAATCCTGCAATTTCGAGCATATTAGTAAGCGGAGTAGGACCAATACCCGGAATCG    2580
  N  N  P  A  I  S  S  I  L  V  S  G  V  G  P  I  P  G  I  G    285

GAGTTGGAGCGGGGACGGGAAATTTATTGACTGCCAACGCCAATGGAATCTCCTCGGGTA    2640
  V  G  A  G  T  G  N  L  L  T  A  N  A  N  G  I  S  S  G  S    305

GCAGTAATTGTTTGGATTACATGCAACAGCAAAATCACATATTCGTGTTTTCAACTCAGC    2700
  S  N  C  L  D  Y  M  Q  Q  N  H  I  F  V  F  S  T  Q  L       325

TGGCCAACAAAGGGGCCGAATCAGTTTTAAGCGGTCAATTTCAAACTATTATTGCGTATC    2760
  A  N  K  G  A  E  S  V  L  S  G  Q  F  Q  T  I  I  A  Y  H    345

ACTGCACTCAGCCTGCTACAAAAAGCTTCCTGGAAGACTTTTTTATGAAAAACCCTTTAA    2820
  C  T  Q  P  A  T  K  S  F  L  E  D  F  F  M  K  N  P  L  K    365

AGATTAACAAGTTACAGCGGCACAATTCCGTCGGTATGCCATGGATAGGCATGGGGCAGG    2880
  I  N  K  L  Q  R  H  N  S  V  G  M  P  W  I  G  M  G  Q  V    385

TTGGACTAACTCCTCCTAATCCTGTAGCCAAAATAACACAACAGCAGCCACATACAAAGA    2940
  G  L  T  P  P  N  P  V  A  K  I  T  Q  Q  Q  P  H  T  K  T    405

CCGTAGGCCTATTGAAACCCCAATTCAATCAACATGAAAACAGCAAACGTAGTACTGTAA    3000
  V  G  L  L  K  P  Q  F  N  Q  H  E  N  S  K  R  S  T  V  S    425

GCGCGCCTAGCAACTCTTTTGTCGACCAGTCTGATCCTATGGGCAACGAAACTGAATTGA    3060
  A  P  S  N  S  F  V  D  Q  S  D  P  M  G  N  E  T  E  L  M    445

TGTGCTGGGAAGGCGGATCCTCAAACACCAGTAGGTCTGGACAAAACTCACGAAATCATG    3120
  C  W  E  G  G  S  S  N  T  S  R  S  G  Q  N  S  R  N  H  V    465

TAGACAGTATCAGTACATCCAGCGAGTCACAGGCAATAAAGATACTGGAAGCAGCTGGCG    3180
  D  S  I  S  T  S  S  E  S  Q  A  I  K  I  L  E  A  A  G  V    485

TTGATTTGGGACAGGTCACAAAAGGAAGCGATCCTGGCCTGACAACTGAAAACAACATTG    3240
  D  L  G  Q  V  T  K  G  S  D  P  G  L  T  T  E  N  N  I  V    505

TATCACTGCAAGGAGTTAAGGTTCCAGACGAAAACCTTACACCACAACAGCGGCAACATC    3300
  S  L  Q  G  V  K  V  P  D  E  N  L  T  P  Q  Q  R  Q  H  R    525

GGGAAGAACAGTTGGCAAAAATAAAAAAAATGAATCAATTTCTTTTTCCTGAAAATGAGA    3360
  E  E  Q  L  A  K  I  K  K  M  N  Q  F  L  F  P  E  N  E  N    545

ATTCAGTAGGAGCTAATGTAAGCTCACAGATAACAAAAATTCCAGGAGATTTAATGATGG    3420
  S  V  G  A  N  V  S  S  Q  I  T  K  I  P  G  D  L  M  M  G    565

GGATGTCGGGTGGCGGAGGCGGATCTATTATAAATCCGACGATGCGACAACTGCATATGC    3480
  M  S  G  G  G  G  S  I  I  N  P  T  M  R  Q  L  H  M  P       585

CAGGTAACGCCAAATCGGAGCTCTTATCGGCGACAAGTTCAGGACTTTCGGAAGATGTAA    3540
  G  N  A  K  S  E  L  L  S  A  T  S  S  G  L  S  E  D  V  M    605
```

FIG. 2D

```
TGCATCCAGGGGATGTTATATCAGATATGGGTGCCGTAATAGGATGTAATAATAATCAAA    3600
 H  P  G  D  V  I  S  D  M  G  A  V  I  G  C  N  N  N  Q  K    625

AAACCAGTGTGCAATGTGGATCTGGAGTAGGTGTTGTCACTGGAACAACTGCAGCTGGAG    3660
 T  S  V  Q  C  G  S  G  V  G  V  V  T  G  T  T  A  A  G  V    645

TAAATGTCAATATGCATTGCTCAAGCTCCGGCGCCCCGAATGGCAATATGATGGGAAGCT    3720
 N  V  N  M  H  C  S  S  S  G  A  P  N  G  N  M  M  G  S  S    665

CTACGGATATGCTAGCCTCGTTTGGCAACACAAGCTGCAACGTCATCGGAACGGCCCCAG    3780
 T  D  M  L  A  S  F  G  N  T  S  C  N  V  I  G  T  A  P  D    685

ATATGTCTAAGGAAGTTTTAAATCAAGATAGCCGAACCCATTCACATCAAGGGGGAGTTG    3840
 M  S  K  E  V  L  N  Q  D  S  R  T  H  S  H  Q  G  G  V  A    705

CTCAAATGGAGTGGTCGAAGATTCAACATCAATTTTTCGAAGAACGCCTCAAGGGGGGCA    3900
 Q  M  E  W  S  K  I  Q  H  Q  F  F  E  E  R  L  K  G  G  K    725

AGCCCAGACAAGTCACTGGAACTGTAGTACCACAACAGCAAACCCCTTCTGGATCTGGTG    3960
 P  R  Q  V  T  G  T  V  V  P  Q  Q  Q  T  P  S  G  S  G  G    745

GAAACTCGTTAAACAACCAGGTGCGACCCCTGCAAGGTCCACCTCCTCCTTACCACTCCA    4020
 N  S  L  N  N  Q  V  R  P  L  Q  G  P  P  P  P  Y  H  S  I    765

TCCAGAGATCTGCGTCAGTACCAATAGCCACTCAATCGCCCAATCCCTCGAGTCCAAACA    4080
 Q  R  S  A  S  V  P  I  A  T  Q  S  P  N  P  S  S  P  N  N    785

ATCTATCTCTCCCGTCACCGCGGACAACCGCAGCAGTCATGGGATTGCCGACCAACTCTC    4140
 L  S  L  P  S  P  R  T  T  A  A  V  M  G  L  P  T  N  S  P    805

CTAGCATGGATGGAACAGGATCATTATCTGGATCTGTTCCGCAAGCTAATACTTCGACGG    4200
 S  M  D  G  T  G  S  L  S  G  S  V  P  Q  A  N  T  S  T  V    825

TTCAGGCAGGCACAACAACAGTGCTCTCAGCAAACAAGAACTGTTTTCAGGCAGACACCC    4260
 Q  A  G  T  T  T  V  L  S  A  N  K  N  C  F  Q  A  D  T  P    845

CATCGCCGTCAAATCAAAATCGTAGTAGAAATACCGGATCGTCAAGCGTTCTTACGCATA    4320
 S  P  S  N  Q  N  R  S  R  N  T  G  S  S  S  V  L  T  H  N    865

ACTTAAGCAGCAACCCAAGTACCCCCTTATCTCATCTATCCCCAAAGGAATTTGAGTCTT    4380
 L  S  S  N  P  S  T  P  L  S  H  L  S  P  K  E  F  E  S  F    885

TCGGTCAGTCCTCTGCTGGTATGTTATATTTGTTTAATTTTTTTAAAGACAAATCAAATA    4440
 G  Q  S  S  A                                                  890

TGAATTGCGTTAATAATAAGTTATATATTACATAACTCGGAAATTTGATAGAAAAAATCA    4500

GGAATAGAAAAAATAAATTATTTTCCGGACCGCCCATCCATTTCTTGAATCCAATTTCTG    4560

GAGTGATTGTTAGAGATAATCTACTATTAAAATTAAACACGAAAATTCATATCCGTTAAT    4620
```

FIG. 2E

```
TGAAAATCACTATTGTTTAATAAGAAATTAAAAATATGTTTATTATAATATTTCTACAGG    4680
                                                           G     891
TGATAACATGAAAAGTAGGCGACCAAGCCCACAGGGTCAGCGGTCACCAGTAAATAGTCT    4740
 D  N  M  K  S  R  R  P  S  P  Q  G  Q  R  S  P  V  N  S  L     911
AATAGAGGCAAATAAAGATGTACGATTTGCTGCATCCAGTCCTGGTTTTAACCCGCATCC    4800
 I  E  A  N  K  D  V  R  F  A  A  S  S  P  G  F  N  P  H  P     931
ACATATGCAAAGCAATTCAAATTCAGCATTAAACGCCTATAAAATGGGCTCTACCAATAT    4860
 H  M  Q  S  N  S  N  S  A  L  N  A  Y  K  M  G  S  T  N  I     951
ACAGATGGAGGTAAATATTTAAATATTTTATTTAACGTTTTGTGTTAATTTATCTTCTT     4920
 Q  M  E                                                         954
TTTCAGCGTCAAGCATCAGCGCAAGGTGGATCCGTACAATTTAGTCGGCGCTCCGATAAT    4980
     R  Q  A  S  A  Q  G  G  S  V  Q  F  S  R  R  S  D  N       972
ATTCCGCTAAATCCCAATAGTGGCAATCGGCCGCCACCAAACAAGATGACCCAAAACTTC    5040
 I  P  L  N  P  N  S  G  N  R  P  P  P  N  K  M  T  Q  N  F     992
GATCCAATCTCTTCTTTGGCACAAATGTCCCAACAACTAACAAGTTGCGTGTCCAGCATG    5100
 D  P  I  S  S  L  A  Q  M  S  Q  Q  L  T  S  C  V  S  S  M    1012
GGTAGTCCAGCCGGAACTGGTGGTATGACGATGATGGGGGGTCCGGGACCGTCCGACATC    5160
```

FIG. 2F

*legless*

```
          G   S   P   A   G   T   G   G   M   T   M   M   G   G   P   G   P   S   D   I        1032
          AATATTGAGCATGGAATAATTTCGGGACTAGATGGATCAGGAATAGATACCATAAATCAA                           5220
          N   I   E   H   G   I   I   S   G   L   D   G   S   G   I   D   T   I   N   Q        1052

AATAACTGTCATTCAATGAATGTCGTAATGAACTCAATGGGTCCCCGAATGCTGAATCCT                           5280
          N   N   C   H   S   M   N   V   V   M   N   S   M   G   P   R   M   L   N   P        1072

AAAATGTGCGTAGCAGGCGGTCCAAATGGACCGCCTGGCTTTAATCCTAATTCCCCCAAT                           5340
          K   M   C   V   A   G   G   P   N   G   P   P   G   F   N   P   N   S   P   N        1092

GGTGGATTAAGAGAGAATTCCATAGGGTCTGGCTGTGGCTCAGCAAACTCTTCAAACTTT                           5400
          G   G   L   R   E   N   S   I   G   S   G   C   G   S   A   N   S   S   N   F        1112

CAAGGGGTTGTTCCACCTGGTGCCAGAATGATGGGTCGAATGCCAGTCAATTTTGGTTCG                           5460
          Q   G   V   V   P   P   G   A   R   M   M   G   R   M   P   V   N   F   G   S        1132

AATTTCAATCCGAATATTCAGGTAAAGGCGAGTACCCCAAACACCATACAATACATGCCA                           5520
          N   F   N   P   N   I   Q   V   K   A   S   T   P   N   T   I   Q   Y   M   P        1152

GTAAGGGCACAGAACGCCAACAACAATAACAACAATGGAGCTAATAATGTGCGAATGCCA                           5580
          V   R   A   Q   N   A   N   N   N   N   N   G   A   N   N   V   R   M   P        1172

CCTAGTCTGGAATTTTTGCAGAGGTACGCTAACCCTCAAATGGGTGCTGTAGGCAATGGG                           5640
          P   S   L   E   F   L   Q   R   Y   A   N   P   Q   M   G   A   V   G   N   G        1192

TCGCCAATATGCCCACCATCAGCCAGCGACGGTACTCCTGGAATGCCAGGATTGATGGCG                           5700
          S   P   I   C   P   P   S   A   S   D   G   T   P   G   M   P   G   L   M   A        1212

GGACCAGGAGCCGGAGGTATGCTAATGAATTCTTCCGGAGAGCAACACCAGAACAAGATC                           5760
          G   P   G   A   G   G   M   L   M   N   S   S   G   E   Q   H   Q   N   K   I        1232

ACAAACAATCCTGGGGCAAGCAATGGTATTAACTTCTTTCAGAATTGCAATCAAATGTCT                           5820
          T   N   N   P   G   A   S   N   G   I   N   F   F   Q   N   C   N   Q   M   S        1252

ATTGTTGACGAAGAGGGTGGATTACCCGGCCATGACGGATCAATGAATATTGGTCAACCA                           5880
          I   V   D   E   E   G   G   L   P   G   H   D   G   S   M   N   I   G   Q   P        1272

TCTATGATAAGGGGCATGCGTCCACATGCCATGCGGCCAAATGTAATGGGTGCGCGGATG                           5940
          S   M   I   R   G   M   R   P   H   A   M   R   P   N   V   M   G   A   R   M        1292

CCACCCGTTAACAGGCAAATTCAGTTTGCACAGTCATCGGATGGTATTGACTGTGTCGGG                           6000
          P   P   V   N   R   Q   I   Q   F   A   Q   S   S   D   G   I   D   C   V   G        1312

GATCCGTCATCATTTTTCACTAACGCTTCCTGCAACAGCGCTGGACCACACATGTTTGGA                           6060
          D   P   S   S   F   F   T   N   A   S   C   N   S   A   G   P   H   M   F   G        1332

TCAGCACAACAGGCCAATCAGCCTAAGACACAACACATAAAGAACATACCTAGTGGAATG                           6120
          S   A   Q   Q   A   N   Q   P   K   T   Q   H   I   K   N   I   P   S   G   M        1352
```

FIG. 2G

```
TGTCAAAACCAATCGGGACTTGCAGTGGCACAAGGGCAGATCCAACTGCATGGGCAAGGA    6180
 C   Q   N   Q   S   G   L   A   V   A   Q   G   Q   I   Q   L   H   G   Q   G    1372
CATGCGCAGGGTCAGTCTTTAATTGGACCTACTAATAATAATTTAATGTCAACTGCCGGA    6240
 H   A   Q   G   Q   S   L   I   G   P   T   N   N   N   L   M   S   T   A   G    1392
AGTGTCAGTGCTACTAACGGTGTCTCTGGCATCAATTTCGTAGGTCCCTCTTCTACGGAC    6300
 S   V   S   A   T   N   G   V   S   G   I   N   F   V   G   P   S   S   T   D    1412
CTGAAGTATGCCCAGCAATATCATAGTTTTCAGCAGCAGTTATATGCTACCAACACCAGA    6360
 L   K   Y   A   Q   Q   Y   H   S   F   Q   Q   Q   L   Y   A   T   N   T   R    1432
AGTCAACAACAACAGCATATGCACCAGCAGCACCAGAGCAACATGATAACAATGCCGCCG    6420
 S   Q   Q   Q   Q   H   M   H   Q   Q   H   Q   S   N   M   I   T   M   P   P    1452
AATTTATCACCAAATCCAACGTTCTTTGTCAACAAATAAACTTCTAAATTTTTGCCGCCC    6480
 N   L   S   P   N   P   T   F   F   V   N   K   *                                1465
TCGTCATGTATTGTTTACTAGTCTCCAAATTAAGACATGCATCTCTAAATAAGATTTTTT    6540
GAAGCTTATTTACTTAGGTGTTTTTACAACGGAGAAAATAAACTTTTGGATATGCAAATG    6600
ATAACGTTGGAAACAACATAATTCATTTGCAACTTTTAGAAGTCACGTCGAAGTTAAATG    6660
TAGAATCTGTATTTTAACATAATAGGTCATCTGTAAAAATAATTAAACATCGAAATTTTA    6720
GTTATCAGCAGCTATTTTCTGTTATTATTTAATATGTGCGCTGCTCTCTCTGTGTTAAAT    6780
GAAATTAAAATATATATATAAATGTAAAACGCTATTGATATATATTGCTCTCAACTGTAT    6840
TGTAATCAATATTAAGAGAACTGTAAATTCTTCCATATAAAGGTAATGAAAAAAAAAAAA    6900
AAAAAAAAA                                                       6909
``` yw x lgs anti-sense yw x lgs sense

EGFP-Lgs

EGFP-Lgs + pcDNA3-Arm-NLS

Figure 5D

| | | BAIT fusions: pLex | | | | | | |
|---|---|---|---|---|---|---|---|---|
| | | Lgs 1-1464 | BCL9 199-392 | BCL9 1-1426 | Dco+ | ΔArmC | ΔB-Cat | Pan |
| PREY fusions: pJG4-5 | lgs364-555 | | | | | + | | |
| | lgs1-385 | | | | | + | | |
| | lgs1-732 | | | | | + | | |
| | lgs364-1090 | | | | | + | | |
| | lgs726-1464 | | | | | + | | |
| | lgs1-1464 | | | | + | + | n.d | + |
| | BCL9 199-392 | | | | | + | n.d | |
| | BCL91-1426 | | | | | + | + | |
| | Dco+ | + | | | | | | |
| | DAxin | (+) | | | - | + | | |
| | ΔArmC | + | + | + | | | | + |
| | B-Cat | + | + | + | | | | |
| | Pan | + | | | | + | | |
| | pJG4-5 | + | + | + | | + | + | |

+: interaction seen in yeast two-hybrid assay
-: no interaction seen in yeast two-hybrid assay
n.d.: not done
numberings refer to amino acid positions.

Figure 5E
Figure 5F
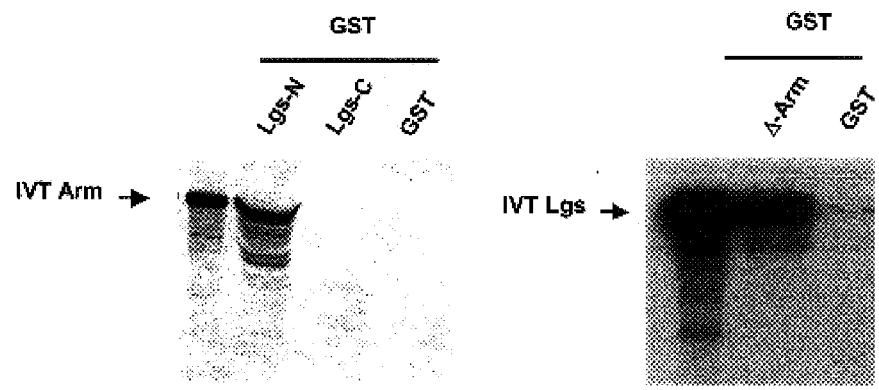
Figure 5G
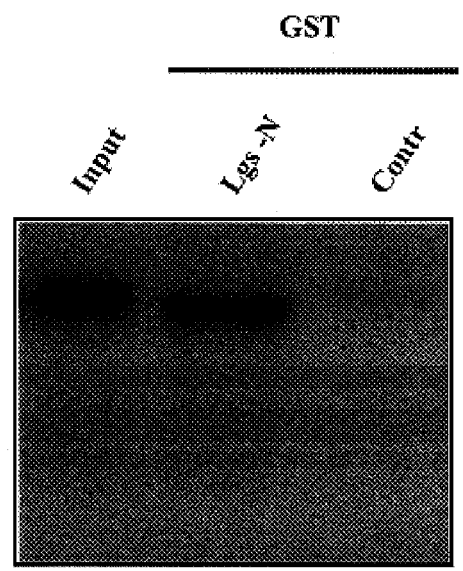

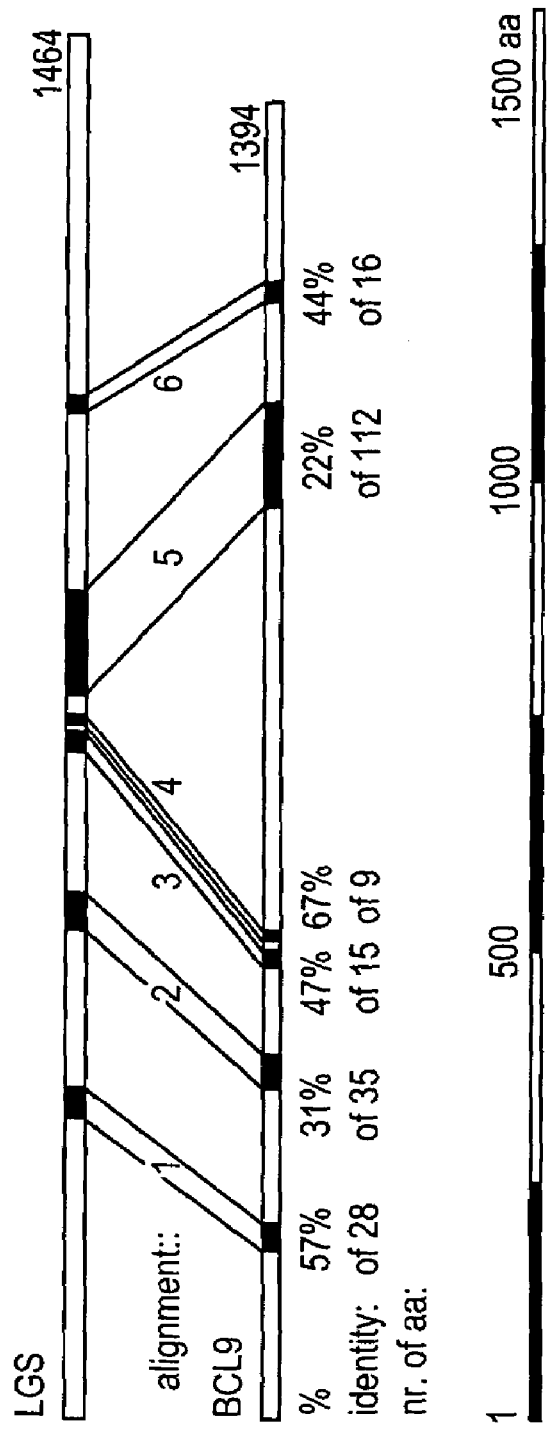

FIG. 7B

Sequence homology domain 1:57.1% identity in 28 aa

```
         320       330       340
LGS      IFVFSTQLANKGAESVLSGQFQTIIAYH
         ..:::::..:::.:::.::  :: .::....:
BCL9     VYVFSTEMANKAAEAVLKGQVETIVSFH
         180       190       200
```

Sequence homology domain 2:31.4% identity in 35 aa

```
          520       530       540
LGS      ENLTPQQRQHREEQLAKIKKMNQFLFPENENSVGA
         ..:....:  .:::   :   .. ...  :::..  . .::
BCL9     DGLSQEQLEHRERSLQTLRDIQRMLFPDEKEFTGA
          350       360       370       380
```

Sequence homology domain 3:46.7% identity in 15 aa

```
         710       720
LGS      QMEWSKIQHQFFEER
         :..:  :.:...:.::.
BCL9     QIAWLKLQQEFYEEK
         470       480
```

Sequence homology domain 4:66.6% identity in 9 aa

```
         760
LGS      LQGPPPPYH
         ..::::::.
BCL9     VRGPPPPYQ
              520
```

Sequence homology domain 5:22.3% identity in 112 aa

```
         770       780       790       800       810       820
LGS      SASVPIATQSPNPSSPNNLSLPSPRTTAAVMGLPTNSPSMDGTGSLSGSVPQANTSTVQA
         ... :.:.:....  :.::....:  :  . .. .  . ..: . ...:. ..
BCL9     GPPPPTASQPASVNIPGSLPSSTPYTMPPEPTLSQNPLSIM-MSRMSKFAMPSSTPLYHD
         970       980       990       1000        1010      1020

830       840       850       860       870
LGS      GTTTVLSANKNCFQADTPSPSNQNRSRNTGSSSVLTHNLSSNPSTPLSHLSP
         .. :: :...  ..:  .:. ..  :   . : ..   ..::: .:.. :::
BCL9     AIKTVASSDDDSPPARSPNLPSMNNMPGMGINTQNPRISGPNPVVPMPTLSP
         1030      1040      1050      1060      1070
```

Sequence homology domain 6:43.8% identity in 16 aa

```
             1080
LGS      NPKMCVAGGPNGPPGF
         .. .:  .:::.::  .:
BCL9     DAALCKPGGPGGPDSF
         1190      1200
```

Figure 8A

ATGCATTCCAGTAACCCTAAAGTGAGGAGCTCTCCATCAGGAAACACACA
GAGTAGCCCTAAGTCAAAGCAGGAGGTGATGGTCCGTCCCCCTACAGTGA
TGTCCCCATCTGGAAACCCCCAGCTGGATTCCAAATTCTCCAATCAGGGT
AAACAGGGGGGCTCAGCCAGCCAATCCCAGCCATCCCCCTGTGACTCCAA
GAGTGGGGGCCATACCCCTAAAGCACTCCCTGGCCCAGGTGGGAGCATGG
GGCTGAAGAATGGGGCTGGAAATGGTGCCAAGGGCAAGGGGAAAAGGGAG
CGAAGTATTTCCGCCGACTCCTTTGATCAGAGAGATCCTGGGACTCCAAA
CGATGACTCTGACATTAAAGAATGTAATTCTGCTGACCACATAAAGTCCC
AGGATTCCCAGCACACACCACACTCGATGACCCCATCAAATGCTACAGCC
CCCAGGTCTTCTACCCCCTCCCATGGCCAAACTACTGCCACAGAGCCCAC
ACCTGCTCAGAAGACTCCAGCCAAAGTGGTGTACGTGTTTTCTACTGAGA
TGGCCAATAAAGCTGCAGAAGCTGTTTTGAAGGGCCAGGTTGAAACTATC
GTCTCTTTCCACATCCAGAACATTTCTAACAACAAGACAGAGAGAAGCAC
AGCGCCTCTGAACACACAGATATCTGCCCTTCGGAATGATCCGAAACCTC
TCCCACAACAGCCCCCAGCTCCGGCCAACCAGGACCAGAATTCTTCCCAG
AATACCAGACTGCAGCCAACTCCACCCATTCCGGCACCAGCACCCAAGCC
TGCCGCACCCCACGTCCCTGGACCGGGAGAGTCCTGGGGTAGAAAACA
AACTGATTCCTTCTGTAGGAAGTCCTGCCAGCTCCACTCCACTGCCCCCA
GATGGTACTGGGCCCAACTCAACTCCCAACAATAGGGCAGTGACCCCTGT
CTCCCAGGGGAGCAATAGCTCTTCAGCAGATCCCAAAGCCCCTCCGCCTC
CACCAGTGTCCAGTGGCGAGCCCCCACACTGGGAGAGAATCCCGATGGC
CTATCTCAGGAGCAGCTGGAGCACCGGGAGCGCTCCTTACAAACTCTCAG
AGATATCCAGCGCATGCTTTTTCCTGATGAGAAAGAATTCACAGGAGCAC
AAAGTGGGGGACCGCAGCAGAATCCTGGGGTATTAGATGGGCCTCAGAAA
AAACCAGAAGGGCCAATACAGGCCATGATGGCCCAATCCCAAAGCCTAGG
TAAGGGACCTGGGCCCCGGACAGACGTGGGAGCTCCATTTGGCCCTCAAG
GACATAGAGATGTACCCTTTTCTCCAGATGAAATGGTTCCACCTTCTATG
AACTCCCAGTCTGGGACCATAGGACCCGACCACCTTGACCATATGACTCC
CGAGCAGATAGCGTGGCTGAAACTGCAGCAGGAGTTTTATGAAGAGAAGA
GGAGGAAGCAGGAACAAGTGGTTGTCCAGCAGTGTTCCCTCCAGGACATG
ATGGTCCATCAGCACGGGCCTCGGGGAGTGGTCCGAGGACCCCCCCCTCC
ATACCAGATGACCCCTAGTGAAGGCTGGGCACCTGGGGGTACAGAGCCAT
TTTCTGATGGTATCAACATGCCACATTCTCTGCCCCCGAGGGGCATGGCT
CCCCACCCCAACATGCCAGGGAGCCAGATGCGCCTCCCTGGATTTGCAGG
CATGATAAACTCTGAAATGGAAGGGCCGAATGTCCCCAACCCTGCATCTA
GACCAGGTCTTTCTGGAGTCAGTTGGCCAGATGATGTGCCAAAAATCCCA
GATGGTCGAAATTTTCCTCCTGGCCAGGGCATTTTCAGCGGTCCTGGCCG
AGGGGAACGCTTCCCAAACCCCCAAGGATTGTCTGAAGAGATGTTTCAGC
AGCAGCTGGCAGAGAAACAGCTGGGTCTCCCCCCAGGGATGGCCATGGAA
GGCATCAGGCCCAGCATGGAGATGAACAGGATGATTCCAGGCTCCCAGCG
CCACATGGAGCCTGGGAATAACCCCATTTTCCCTCGAATACCAGTTGAGG
GCCCTCTGAGTCCTTCTAGGGGTGACTTTCCAAAAGGAATTCCCCCACAG

Figure 8A (Cont.)

```
ATGGGCCCTGGTCGGGAACTTGAGTTTGGGATGGTTCCTAGTGGGATGAA
GGGAGATGTCAATCTAAATGTCAACATGGGATCCAACTCTCAGATGATAC
CTCAGAAGATGAGAGAGGCTGGGGCGGGCCCTGAGGAGATGCTGAAATTA
CGCCCAGGTGGCTCAGACATGCTGCCTGCTCAGCAGAAGATGGTGCCACT
GCCATTTGGTGAGCACCCCAGCAGGAGTATGGCATGGGCCCCAGACCAT
TCCTTCCCATGTCTCAGGGTCCAGGCAGCAACAGTGGCTTGCGGAATCTC
AGAGAACCAATTGGGCCCGACCAGAGGACTAACAGCCGGCTCAGTCATAT
GCCACCACTACCTCTCAACCCTTCCAGTAACCCCACCAGCCTCAACACAG
CTCCTCCAGTTCAGCGCGGCCTGGGGCGGAAGCCCTTGGATATATCTGTG
GCAGGCAGCCAGGTGCATTCCCCAGGCATTAACCCTCTGAAGTCTCCCAC
GATGCACCAAGTCCAGTCACCAATGCTGGGCTCGCCCTCGGGGAACCTCA
AGTCCCCCCAGACTCCATCGCAGCTGGCAGGCATGCTGGCGGGCCCAGCT
GCTGCTGCTTCCATTAAGTCCCCCCCTGTTTTGGGGTCTGCTGCTGCTTC
ACCTGTCCACCTCAAGTCTCCATCACTTCCTGCCCCGTCACCTGGATGGA
CCTCTTCTCCAAAACCTCCCCTTCAGAGTCCTGGGATCCCTCCAAACCAT
AAAGCACCCCTCACCATGGCCTCCCCAGCCATGCTGGGAAATGTAGAGTC
AGGTGGCCCCCCACCTCCTACAGCCAGCCAGCCTGCCTCTGTGAATATCC
CTGGAAGTCTTCCCTCTAGTACACCTTATACCATGCCTCCAGAGCCAACC
CTTTCCCAGAACCCACTCTCTATTATGATGTCTCGAATGTCCAAGTTTGC
AATGCCCAGTTCCACCCCGTTATACCATGATGCTATCAAGACTGTGGCCA
GCTCAGATGACGACTCCCCTCCAGCTCGTTCTCCCAACTTGCCATCAATG
AATAATATGCCAGGAATGGGCATTAATACACAGAATCCTCGAATTTCAGG
TCCAAACCCCGTGGTTCCGATGCCAACCCTCAGCCCAATGGGAATGACCC
AGCCACTTTCTCACTCCAATCAGATGCCCTCTCCAAATGCCGTGGGACCC
AACATACCTCCTCATGGGGTCCCAATGGGGCCTGGCTTGATGTCACACAA
TCCTATCATGGGGCATGGGTCCCAGGAGCCACCGATGGTACCTCAAGGAC
GGATGGGCTTCCCCCAGGGCTTCCCTCCAGTACAGTCTCCCCCACAGCAG
GTTCCATTCCCTCACAATGGCCCCAGTGGGGGGCAGGGCAGCTTCCCAGG
AGGGATGGGTTTCCCAGGAGAAGGCCCCCTTGGCCGCCCCAGCAACCTGC
CCCAAAGTTCAGCAGATGCAGCACTTTGCAAGCCTGGAGGCCCCGGGGGT
CCTGACTCCTTCACTGTCCTGGGGAACAGCATGCCTTCGGTGTTTACAGA
CCCAGATCTGCAGGAGGTCATCCGACCTGGAGCCACCGGAATACCTGAGT
TTGATCTATCCCGCATTATTCCATCTGAGAAGCCCAGCCAGACGCTGCAA
TATTTCCCTCGAGGGGAAGTTCCAGGCCGTAAACAGCCCCAGGGTCCTGG
ACCTGGGTTTTCACACATGCAGGGGATGATGGGCGAACAAGCCCCAGAA
TGGGACTAGCATTACCTGGCATGGGAGGTCCAGGGCCAGTGGGAACTCCG
GACATCCCTCTTGGTACAGCTCCATCCATGCCAGGCCACAACCCCATGAG
ACCACCAGCCTTTCTCCAACAAGGCATGATGGGACCTCACCATCGGATGA
TGTCACCAGCACAATCTACAATGCCCGGCCAGCCCACCCTGATGAGCAAT
CCAGCTGCTGCCGTGGGCATGATTCCTGGCAAGGATCGGGGGCCTGCCGG
GCTCTACACCCACCCTGGGCCTGTGGGCTCTCCAGGCATGATGATGTCCA
TGCAGGGCATGATGGGACCCCAACAGAACATCATGATCCCCCCACAGATG
AGGCCCCGGGGCATGGCTGCTGACGTGGGCATGGGTGGATTTAGCCAAGG
ACCTGGCAACCCAGGAAACATGATGTTTTAA
```

Figure 8B

MHSSNPKVRSSPSGNTQSSPKSKQEVMVRPPTVMSPSGNPQLDSKFSNQG
KQGGSASQSQPSPCDSKSGGHTPKALPGPGGSMGLKNGAGNGAKGKGKRE
RSISADSFDQRDPGTPNDDSDIKECNSADHIKSQDSQHTPHSMTPSNATA
PRSSTPSHGQTTATEPTPAQKTPAKVVYVFSTEMANKAAEAVLKGQVETI
VSFHIQNISNNKTERSTAPLNTQISALRNDPKPLPQQPPAPANQDQNSSQ
NTRLQPTPPIPAPAPKPAAPPRPLDRESPGVENKLIPSVGSPASSTPLPP
DGTGPNSTPNNRAVTPVSQGSNSSSADPKAPPPPPVSSGEPPTLGENPDG
LSQEQLEHRERSLQTLRDIQRMLFPDEKEFTGAQSGGPQQNPGVLDGPQK
KPEGPIQAMMAQSQSLGKGPGPRTDVGAPFGPQGHRDVPFSPDEMVPPSM
NSQSGTIGPDHLDHMTPEQIAWLKLQQEFYEEKRRKQEQVVVQQCSLQDM
MVHQHGPRGVVRGPPPPYQMTPSEGWAPGGTEPFSDGINMPHSLPPRGMA
PHPNMPGSQMRLPGFAGMINSEMEGPNVPNPASRPGLSGVSWPDDVPKIP
DGRNFPPGQGIFSGPGRGERFPNPQGLSEEMFQQQLAEKQLGLPPGMAME
GIRPSMEMNRMIPGSQRHMEPGNNPIFPRIPVEGPLSPSRGDFPKGIPPQ
MGPGRELEFGMVPSGMKGDVNLNVNMGSNSQMIPQKMREAGAGPEEMLKL
RPGGSDMLPAQQKMVPLPFGEHPQQEYGMGPRPFLPMSQGPGSNSGLRNL
REPIGPDQRTNSRLSHMPPLPLNPSSNPTSLNTAPPVQRGLGRKPLDISV
AGSQVHSPGINPLKSPTMHQVQSPMLGSPSGNLKSPQTPSQLAGMLAGPA
AAASIKSPPVLGSAAASPVHLKSPSLPAPSPGWTSSPKPPLQSPGIPPNH
KAPLTMASPAMLGNVESGGPPPPTASQPASVNIPGSLPSSTPYTMPPEPT
LSQNPLSIMMSRMSKFAMPSSTPLYHDAIKTVASSDDDSPPARSPNLPSM
NNMPGMGINTQNPRISGPNPVVPMPTLSPMGMTQPLSHSNQMPSPNAVGP
NIPPHGVPMGPGLMSHNPIMGHGSQEPPMVPQGRMGFPQGFPPVQSPPQQ
VPFPHNGPSGGQGSFPGGMGFPGEGPLGRPSNLPQSSADAALCKPGGPGG
PDSFTVLGNSMPSVFTDPDLQEVIRPGATGIPEFDLSRIIPSEKPSQTLQ
YFPRGEVPGRKQPQGPGPGFSHMQGMMGEQAPRMGLALPGMGGPGPVGTP
DIPLGTAPSMPGHNPMRPPAFLQQGMMGPHHRMMSPAQSTMPGQPTLMSN
PAAAVGMIPGKDRGPAGLYTHPGPVGSPGMMMSMQGMMGPQQNIMIPPQM
RPRGMAADVGMGGFSQGPGNPGNMMF*

Figure 10A

```
ATGGCCTGCTTCCCATCCCCTGCTGCCATCTCCTGCACCCTTAGGGCACAGTGGGCATCT
CGGGAGCTGCTCAGCGGACAGACTAGGGTTACCCCCACCCCAGGAGGAGAGAAGCTCCAG
GGAGCCCGCCGCTGTCCCCCGCGGTCATTGCCCCCTGCCCCAGCCAAGCCAATGCACCCA
GAAAATAAATTGACCAATCATGGCAAGACAGGGAATGGCGGGGCCCAATCTCAGCACCAG
AATGTGAACCAAGGACCCACCTGCAACGTGGGCTCGAAGGGCGTGGGGGCGGGGAACCAT
GGGGCCAAGGCCAACCAGATCTCGCCTAGCAACTCAAGTCTGAAGAACCCCCAGGCAGGG
GTGCCCCCTTTCAGCTCGCTCAAGGGCAAGGTGAAGAGGGACCGGAGTGTGTCTGTGGAC
TCTGGAGAGCAGCGAGAGGCTGGGACCCCATCCCTGGATTCAGAGGCCAAAGAGGTGGCG
CCGCGGAGTAAGCGGCGCTGTGTGCTGGAGCGGAAGCAGCCGTACAGTGGGGACGAATGG
TGCTCTGGACCGGACAGTGAGGAGGACGACAAGCCCATTGGGGCCACCCACAAAGCTGCT
TTCAAAGAAGACGGCTTTCAGGACAAGGCATCACACTTCTTCTCCAGCACGTACAGTCCT
GAAACCTCCAGGAGGAAGCTGCCCCAAGCCCCGAAGGCTTCCTTCCTGGGGCAGCAGGGC
CGAGTCATTTGGAAACCTCTCTCGGAGGAGCTCCGTGATCAAGGTGCAGATGCGGCAGGT
GGGCCGGCCTCAATCATGTCTCCAATCGCGACGGTGAATGCGAGTGGCTTGTCCAAAGAG
CAGCTGGAGCATCGGGAACGGTCCCTCCAGACGCTGCGAGACATTGAGCGACTGCTGCTC
CGCAGCGGAGAGACTGAGCCCTTCCTCAAGGGGGCCCCAGGAGGAGCGGCGGGCTGAAG
AAATATGAGGAACCCTTGCAGTCCATGATTTCACAGACACAGAGCCTAGGGGGCCCCCG
CTGGAGCATGAAGTGCCTGGGCACCCCCCGGGTGGGGACATGGGGCAGCAGATGAACATG
ATGATACAGAGGCTGGGCCAGGACAGCCTCACGCCTGAGCAGGTGGCCTGGCGCAAGCTG
CAGGAGGAGTACTACGAAGAGAAACGGCGGAAAGAGGAACAGATTGGGCTGCATGGGAGC
CGTCCTCTGCAGGACATGATGGGCATGGGGGGCATGATGGTGAGGGGCCCCCGCCTCCT
TACCACAGCAAGCCTGGGGATCAGTGGCCACCTGGAATGGGTGCGCAGCTGCGGGGGCCC
ATGGATGTTCAAGATCCCATGCAGCTCCGGGGCGGACCTCCCTTTCCTGGGCCCCGTTTC
CCAGGCAACCAGATACAACGGGTACCTGGGTTTGGGGGCATGCAGAGTATGCCCATGGAG
GTGCCCATGAATGCCATGCAGAGGCCCGTGAGACCAGGCATGGGCTGGACCGAAGACTTG
CCCCCTATGGGGGGACCCAGCAATTTTGCCCAGAACACCATGCCCTACCCAGGTGGGCAG
GGTGAGGCGGAGCGATTCATGACTCCCCGGGTCCGTGAGGAGCTGCTGCGGCACCAGCTG
CTGGAGAAGCGGTCGATGGGCATGCAGCGCCCCCTGGGCATGGCAGGCAGTGGCATGGGA
CAGAGCATGGAGATGGAGCGGATGATGCAGGCGCACCGACAGATGGATCCTGCCATGTTT
CCCGGGCAGATGGCTGGTGGTGAGGGCCTGGCGGGCACTCCCATGGGCATGGAGTTTGGT
GGAGGCCGGGGCCTCCTGAGCCCTCCCATGGGGCAGTCTGGGCTGAGGGAGGTGGACCCA
CCCATGGGGCCAGGCAACCTCAACATGAACATGAATGTCAACATGAACATGAACATGAAC
CTGAACGTGCAGATGACCCCGCAGCAGCAGATGCTGATGTCGCAGAAGATGCGGGGCCCT
GGGGACTTGATGGGGCCCCAGGGCCTCAGTCCTGAGGAGATGGCCCGGGTTCGGGCCCAG
AACAGCAGTGGCATGGTGCCCTTGCCTTCTGCCAACCCGCCAGGACCTCTCAAGTCGCCC
CAGGTCCTCGGCTCCTCCCTCAGTGTCCGTTCACCCACTGGCTCGCCCAGCAGGCTCAAG
TCTCCTTCCATGGCGGTGCCTTCTCCAGGCTGGGTTGCCTCACCCAAGACGGCCATGCCC
AGCCCGGGGGTCTCCCAGAACAAGCAGCCGCCTCTCAACATGAACTCTTCCACCACCCTG
AGCAACATGGAACAGGACCCCACACCTTCCCAGAACCCCCTGTCACTGATGATGACCCAG
ATGTCCAAGTACGCCATGCCCAGCTCCACCCCGCTCTACCACAATGCCATCAAGACCATC
GCCACCTCAGACGACGAGCTGCTGCCCGACCGGCCCTGCTGCCCCCCCCACCACCACCG
CAGGGCTCCGGGCCAGGTGGCCCCGACTCCCTGAATGCCCCCTGTGGCCCAGTGCCCAGC
TCCTCCCAGATGATGCCCTTCCCCCCTCGGCTGCAGCAGCCCCATGGTGCCATGGCCCCC
ACTGGGGGTGGGGCGGGGGGCCTGGCCTGCAGCAGCACTACCCGTCAGGCATGGCCCTG
CCTCCCGAGGACCTGCCCAACCAGCCGCCAGGCCCCATGCCTCCCCAGCAGCACCTGATG
GGCAAAGCCATGGCTGGGCGCATGGGCGACGCATACCCACCGGGTGTGCTCCCTGGGGTG
GCATCAGTGCTGAACGACCCCGAGCTGAGCGAGGTGATCCGGCCCACCCCAACGGGGATC
CCCGAGTTCGACTTGTCGAGGATCATCCCCTCTGAGAAGCCAAGCAGCACCCTCCAGTAC
TTCCCCAAGAGCGAGAACCAGCCCCCAAGGCTCAGCCCCTAATCTGCATCTCATGAAC
CTGCAGAACATGATGGCGGAGCAGACTCCCTCTCGGCCTCCCAACCTCCCAGGCCAGCAG
GGCGATCGGCCGCTGGTGGTGGTGATACCGGGTACCCGGGCTATGGCGCCGGCGCAGCGC
TGCCCTCTGTGCCGCCAGACCTTCTTCTGTGGTCGCGGGCACGTTTACAGCCGCAAGCAC
CAGCGGCAGCTGAAGGAGGCTTTGGAGAGGCTCCTGCCCCAGGTGGAGGCGGCCCGCAAG
GCCATCCGCGCCGCTCAGGTGGAGCGCTATGTGCCCGAACACGAGCGATGCTGCTGGTGC
CTGTGCTGCGGCTGTGAGGTGCGGGAACACCTGAGCCATGGAAACCTGACGGTGCTGTAC
```

Figure 10A (Cont.)

```
GGGGGGCTGCTGGAGCATCTGGCCAGCCCAGAGCACAAGAAAGCAACCAACAAATTCTGG
TGGGAGAACAAAGCTGAGGTCCAGATGAAAGAGAAGTTTCTGGTCACTCCCCAGGATTAT
GCGCGATTCAAGAAATCCATGGTGAAAGGTTTGGATTCCTATGAAGAAAAGGAGGATAAA
GTGATCAAGGAGATGGCAGCTCAGATCCGTGAGGTGGAGCAGAGCCGACAGGAGGTGGTT
CGGTCTGTCTTAGAGACAGGTCCCCAAGATACGCCCTCACAGTCCGGTCCCCCGCCGTC
CTCTCCCGGCGCACGCTCAAGTCCGGTGCCTTCCCCCGCAGACCCCCGAGGCGCACCCT
CAAGCTCGGTGCCTCTGCGCCCCCGCAGGGGCGCCCTCAAGCCTGAGCCCCCCGGGCGC
ACCCTCAAGCTCGGTGTACCCCCCCATACCACCCGCAAGGCGCGCCCTCATGCCGCGAAG
ACTTCGCCCCGCCCAAGGTGCACCCGTCAAGCCCCGAATAAAACCCAGTCACTCCAACTT
GCAGGCAAAGCTAGAAAAACTGCGCTGCATTTGCAAACAAAAGCTCTTGTTGGCGATGAC
GATACTGTTTTGGGTGTGAAACTGTCAATTGCTAACTACGATCTGTGA
```

Figure 10B

FKEDGFQDKASHFFSSTYSPETSRRKLPQAPKASFLGQQGRVIWKPLSEE
LRDQGADAAGGPASIMSPIATVNASGLSKEQLEHRERSLQTLRDIERLLL
RSGETEPFLKGAPRRSGGLKKYEEPLQSMISQTQSLGGPPLEHEVPGHPP
GGDMGQQMNMMIQRLGQDSLTPEQVAWRKLQEEYYEEKRRKEEQIGLHGS
RPLQDMMGMGGMMVRGPPPPYHSKPGDQWPPGMGAQLRGPMDVQDPMQLR
GGPPFPGPRFPGNQIQRVPGFGGMQSMPMEVPMNAMQRPVRPGMGWTEDL
PPMGGPSNFAQNTMPYPGGQGEAERFMTPRVREELLRHQLLEKRSMGMQR
PLGMAGSGMGQSMEMERMMQAHRQMDPAMFPGQMAGGEGLAGTPMGMEFG
GGRGLLSPPMGQSGLREVDPPMGPGNLNMNMNVNMNMNMNLNVQMTPQQQ
MLMSQKMRGPGDLMGPQGLSPEEMARVRAQNSSGMVPLPSANPPGPLKSP
QVLGSSLSVRSPTGSPSRLKSPSMAVPSPGWVASPKTAMPSPGVSQNKQP
PLNMNSSTTLSNMEQDPTPSQNPLSLMMTQMSKYAMPSSTPLYHNAIKTI
ATSDDELLPDRPLLPPPPPQGSGPGGPDSLNAPCGPVPSSSQMMPFPPR
LQQPHGAMAPTGGGGGGPGLQQHYPSGMALPPEDLPNQPPGPMPPQQHLM
GKAMAGRMGDAYPPGVLPGVASVLNDPELSEVIRPTPTGIPEFDLSRIIP
SEKPSSTLQYFPKSENQPPKAQPPNLHLMNLQNMMAEQTPSRPPNLPGQQ
GDRPLVVVIPGTRAMAPAQRCPLCRQTFFCGRGHVYSRKHQRQLKEALER
LLPQVEAARKAIRAAQVERYVPEHERCCWCLCCGCEVREHLSHGNLTVLY
GGLLEHLASPEHKKATNKFWWENKAEVQMKEKFLVTPQDYARFKKSMVKG
LDSYEEKEDKVIKEMAAQIREVEQSRQEVVRSVLETGPPRYALTVRSPAV
LSRRTLKSGAFPPQTPEAHPQARCLCAPRRGALKPEPPGRTLKLGVPPHT
TRKARPHAAKTSPRPRCTRQAPNKTQSLQLAGKARKTALHLQTKALVGDD
DTVLGVKLSIANYDL

FIG. 12A
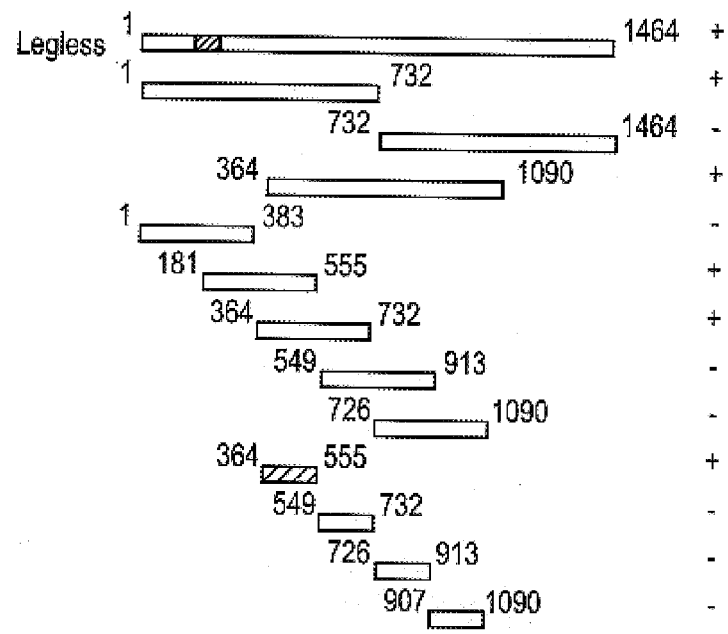
FIG. 12B
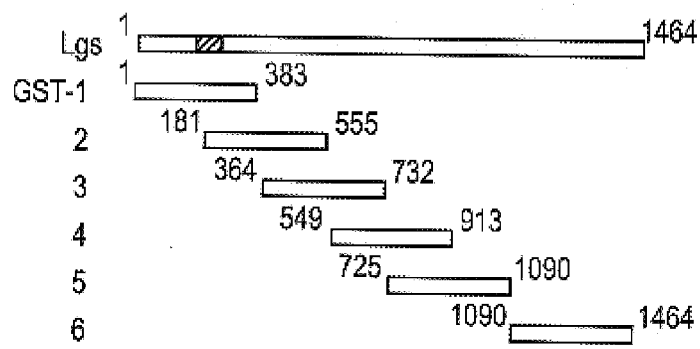
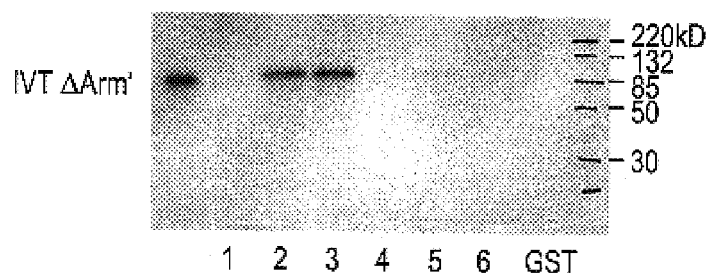

FIG. 12E

| Construct | Invitro interaction |
|---|---|
| N▨ 1 2 3 4 5 6 7 8 9 10 11 12 13 ▨ C | + + |
| 1 2 3 4 5 6 7 8 9 10 11 12 13 ▨ C | + + |
| ▨ C | - |
| N▨ 1 2 3 4 5 6 7 8 9 10 11 12 13 | + + |
| N▨ 1 2 3 4 5 6 7 8 | + + + |
| N▨ 1 2 3 4 5 6 | + + + |
| N▨ 1 2 3 4 | + + |
| N▨ 1 2 | - |
| 1 2 3 4 5 6 7 8 9 10 11 12 13 | + + |
| 1 2 3 4 5 6 7 8 | + + + |
| 1 2 3 4 5 6 | + + + |
| 1 2 3 4 | + + |
| 1 2 | - |
| 3 4 5 6 7 8 | (+) |
| 5 6 7 8 | (-) |
| 7 8 9 10 11 12 13 | (-) |
| 9 10 11 12 13 | (-) |

ESSENTIAL DOWNSTREAM COMPONENT OF THE WINGLESS SIGNALING PATHWAY AND THERAPEUTIC AND DIAGNOSTIC APPLICATIONS BASED THEREON

CROSS-REFERENCE TO RELATED APPLICATION

This application is a Divisional of application Ser. No. 09/915,543, filed Jul. 27, 2001 (now U.S. Pat. No. 7,049,290); which claims benefit under 35 U.S.C. § 111(a) and 35 U.S.C. § 119(e) (1) of the filing date of Provisional Application No. 60/221,502, filed Jul. 28, 2000, pursuant to 35 U.S.C. § 111(b); the disclosure of each of which is incorporated herein by reference in their entirety.

FIELD OF THE INVENTION

The present invention relates to a new essential downstream component of the Wnt/Wingless (Wnt/Wg) signaling pathway and therapeutic and diagnostic applications based thereon. The invention relates to nucleotide sequences of the *Drosophila melanogaster* legless (lgs) gene, of its encoded proteins, as well as derivatives (e.g., fragments) and analogues thereof. The invention further includes vertebrate and invertebrate homologues of the Lgs protein, comprising proteins that contain a contiguous stretch of amino acids with similarity to the *Drosophila* lgs gene. The invention further relates to the function of the *Drosophila* and the human Lgs proteins. Methods for producing the Lgs proteins, derivatives and analogs, e.g., by recombinant means and antibodies to Lgs are provided by the present invention. In addition, the invention also relates to therapeutic and diagnostic methods and compositions based on Lgs proteins and nucleic acids or fragments thereof.

BACKGROUND OF THE INVENTION

Wnt genes encode a large family of secreted, cysteine rich proteins that play key roles as intercellular signaling molecules in a wide variety of biological processes (for an extensive review see (Wodarz and Nusse 1998)). The first Wnt gene, mouse wnt-1, was discovered as a proto-oncogene activated by integration of mouse mammary tumor virus in mammary tumors (Nusse and Varmus 1982). Consequently, the involvement of the Wnt pathway in cancer has been largely studied. With the identification of the *Drosophila* polarity gene wingless (wg) as a wnt-1 homologue (Cabrera, Alonso et al. 1987; Perrimon and Mahowald 1987; Rijsewijk, Schuermann et al. 1987), it became clear that wnt genes are important developmental regulators. Thus, although at first glance dissimilar, biological processes like embryogenesis and carcinogenesis both rely on cell communication via identical signaling pathways. In a current model of the pathway, the secreted Wnt protein binds to Frizzle cell surface receptors and activates the cytoplasmic protein Dishevelled (Dsh). Dsh then transmits the signal to a complex of several proteins, including the protein kinase Shaggy/GSK3 (Sgg), the APC tumor supressor, the scaffold protein Axin and β-Catenin (β-Cat), the vertebrate homologue of *Drosophila* Armadillo. In this complex β-Cat is targeted for degradation after being phosphorylated by Sgg. After Wnt signaling and the resulting down-regulation of Sgg activity, β-Cat (or its *Drosophila* homologue Armadillo) escape from degradation and accumulate into the cytoplasm. Free cytoplasmic β-Cat translocates to the nucleus by a still obscure mechanism, and modulates gene transcription through binding the Tcf/Lef family of transcription factors (Grosschedl R 1999). Mutations of β-Cat itself or of negative regulatory elements, like APC and Axin, that lead to nuclear accumulation of β-Cat and consequently to constitutive activation of the Wnt pathway have been observed in many types of cancers, including colon, skin and breast cancer (Barker N 1999; Morin 1999; Potter 1999; Roose and Clevers 1999; Waltzer and Bienz 1999). Currently, there are no known therapeutic agents effectively inhibiting β-Cat transcriptional activation. This is partly due to the fact that many of the essential components required for its full activation and nuclear translocation are still unknown. Consequently, there is an urge to understand more about this pathway to develop effective drugs against these highly malignant diseases.

In order to identify new components required for Wingless (Wg) activation we used a *Drosophila* genetic approach. Specifically, we screened for dominant suppressors of the rough eye phenotype caused by a transgene that drives ectopic expression of Wg, the *Drosophila* homologue of Wnt, during eye development. Three genes were identified: the β-cat homologue armadillo (arm), the tcf/lef-1 homologue pangolin (pan) and legless (lgs), a completely new gene. We subsequently cloned lgs and confirmed its in vivo requirement for Wg signal transduction in embryo and in developing tissues. Epistasis experiments revealed that Lgs is at the same level or downstream of Arm. In addition, we found that the Lgs protein binds to and translocates to the nucleus with Arm in mammalian cells. Biochemical experiments confirmed the binding of Lgs to Arm. Lgs forms a tri-molecular complex with Pan and Arm and enhances the transcriptional activity of the complex.

Sequence homology search using the Blast search tool at NCBI revealed at least two human proteins sharing short amino acids domains with up to 66% sequence identity with *Drosophila* Lgs (dLgs). One of them, hLgs/Bcl9, has been previously implicated in B cell malignancies (Willis, Zalcberg et al. 1998). The other, hLgs-1, is a completely new gene. Several Expressed Sequence Tags (EST) could be found for both human homologues in the public human genome database, demonstrating the presence of their gene products in human normal and tumor tissues. Subsequent genetic and biochemical experiments confirmed the functional homology of hLgs to dLgs. Particularly, hLgs/Bcl9 not only binds to β-Cat and its *Drosophila* homologue Armadillo (Arm), but is also able to substitute for lack of dLgs during fly development. Furthermore, point mutations or deletions in the homology domains between dLgs and hLgs disrupt Lgs function, highlighting the essential role of these evolutionary conserved domains.

Lgs thus represents an exquisite target for all the diseases caused by the over-activation of the β-Cat/Tcf complex.

SUMMARY OF THE INVENTION

The present invention relates to the discovery of a novel family of proteins present in insects and vertebrate organisms, referred to hereinafter as "Legless (Lgs)" proteins. These proteins play an essential role in the Wnt/Wg signaling pathway, and thus in the formation and maintenance of spatial arrangements and proliferation of tissues during development, and in the formation and growth of many human tumors.

In general, the invention relates to nucleotide sequences of the *Drosophila melanogaster* lgs gene, of its encoded protein, as well as derivatives (e.g., fragments) and structural and functional analogs thereof. The invention further includes the predicted nucleotide and protein sequences of a human lgs homologue, hlgs-1, and the use of another human Lgs homologue hLgs/Bcl9 (Willis, Zalcberg et al. 1998), to modulate or diagnose diseases related to the Wnt signaling pathway.

In one embodiment, the isolated nucleic acid comprises a sequence having at least 50% sequence identity, preferably at least 70% sequence identity, more preferably at least 80% sequence identity, even more preferably at least 90% sequence identity, yet even more preferably at least 98% sequence identity, and most preferably 100% identity to (a) a nucleic acid molecule encoding a Lgs polypeptide having the sequence of amino acid residues from 1 to 1484 of FIGS. 2A-2G (SEQ ID NO:1), or (b) the complement of the nucleic acid molecule of (a).

In another embodiment, the isolated nucleic acid containing a sequence having at least 30% sequence identity, preferably 50% sequence identity, more preferably at least 70% sequence identity, even more preferably 90% sequence identity, yet even more preferably 95% sequence identity to (a) a nucleic acid molecule encoding a human Lgs polypeptide of FIG. 10A (SEQ ID NO:16) or (b) the complement of the nucleic acid molecule of (a).

In a further embodiment, the isolated nucleic acid comprises a sequence with a low overall sequence identity but shows a sequence identity of at least 30%, preferably at least 50%, more preferably at least 70%, even more preferably at least 90% and most preferably 100% in the evolutionary conserved domains described in FIG. 7B (SEQ ID NOs:2-13).

In yet another embodiment of the present invention isolated nucleic acids encode polypeptides having a function resembling that of the lgs gene products.

In another embodiment, the invention relates to a fragment of the *Drosophila* or human lgs nucleic acid sequences that can find use as hybridization probe. Such nucleic acid fragments are about 18 to about 100 nucleotides in length, preferably from about 20 to about 60 nucleotides in length, most preferably from 20 to 50 nucleotides in length and can be derived from the nucleotides sequences shown in FIGS. 2A-2G (SEQ ID NO:1) and FIG. 10(A) (SEQ ID NO:16).

In another aspect, the invention provides a vector comprising a nucleic acid molecule encoding vertebrate or invertebrate Lgs proteins or a fragment thereof. The vector can comprise any of the molecules or fragments thereof described above.

The invention also includes host cells comprising such a vector. By the way of example, the host cells can be mammalian cells, yeast cells, insect cells or bacteria cells.

Methods of production, isolation and purification of the Lgs proteins, derivatives and analogs, e.g., by recombinant means, are also provided. In a specific embodiment, the invention concerns an isolated Lgs polypeptide or a fragment thereof, comprising an amino acid sequence of at least 80%, preferably at least about 85% sequence identity, more preferably at least 90% sequence identity, even more preferably at least 95% sequence identity, yet most preferably 100% identity with the sequence of amino acid residues 1 to 1464 of *Drosophila* Lgs of FIGS. 2A-2G (SEQ ID NO:1) or amino acids residues of hLgs-1 of FIG. 10B (SEQ ID NO:17).

In yet another embodiment the invention relates to chimeric proteins comprising a Lgs polypeptide fused to a heterologous polypeptide or amino acid sequence. An example of such chimeric molecule comprises a Lgs polypeptide fused to an epitope tag sequence, glutathione-S-transferase protein or to a protein with an enzymatic activity, such as beta-galactosidase or alkaline phosphatase, a thioredoxin moiety, or an antibody moiety.

A further aspect of the invention concerns an isolated full length Lgs polypeptide, comprising the sequence of amino acid residues 1 to 1464 of FIGS. 2A-2G (SEQ ID NO:1), or any Lgs polypeptide or fragment thereof comprised in this invention sufficient to provide a binding site for an anti-Lgs antibody.

In another embodiment the invention provides antibodies, which specifically recognize Lgs polypeptides. The antibodies can be a polyclonal or a monoclonal preparation or fragments thereof.

The present invention also provides an antisense oligonucleotide having a sequence capable of specifically hybridizing to RNA encoding vertebrate and invertebrate Lgs, so as to prevent translation of such RNA. This invention further provides an antisense oligonucleotide having a sequence capable of specifically hybridizing to genomic DNA encoding a vertebrate and invertebrate Lgs, so as to prevent transcription of such genomic DNA. In one embodiment, the oligonucleotide comprises chemically modified nucleotides or nucleotide analogues.

The invention also relates to transgenic animals, e.g., *Drosophila*, mice, rats, chicken, frogs, pigs or sheep, having a transgene, e.g., animals that include and preferably express, a heterologous form of the Lgs genes described herein, or that misexpress an endogenous lgs gene. Such a transgenic animal can serve as a model to study diseases with disrupted Wnt signaling pathway, for the production of Lgs proteins, or for drug screening.

In yet another embodiment, the invention also features animals, e.g., *Drosophila*, mice, rats, chicken, frogs, pigs or sheep, having a mutation in a lgs gene, e.g., deletions, point mutations, foreign DNA insertions or inversions. Such animals can serve to study diseases characterized by disrupted Wnt function or in drug screening.

The invention also relates to therapeutic and diagnostic methods and compositions based on Lgs proteins and their homologues as well as the respective nucleic acids or fragments thereof. In particular, the invention provides for treatment of disorders of cell fate, differentiation or proliferation involving the Wnt pathway by administration of a therapeutic compound of the invention. Such therapeutic compounds include: *Drosophila* and vertebrate Lgs protein homologues or fragments thereof, antibodies or antibody fragments thereto, lgs antisense DNA or RNA, lgs double stranded RNA, and any chemical or natural occurring compound interfering with Lgs-function, synthesis or degradation. In a preferred embodiment, a therapeutic product according to the invention is administered to treat a cancerous condition or to prevent progression from a pre-neoplastic or non-malignant condition to a neoplastic or malignant state.

In a specific embodiment, a therapeutic product of the invention is administered to treat a blood disease or to promote tissue regeneration and repair. Disorders of cell fate, especially hyperproliferative or hypoproliferative disorders, involving aberrant or undesirable expression, or localization, or activity of the Lgs protein can be diagnosed by detecting such levels.

The present invention also provides a pharmaceutical composition comprising (a) an amount of a Lgs oligonucleotide in accordance with this invention capable of passing through a cell membrane and effective to reduce expression of Lgs and (b) a pharmaceutically acceptable carrier capable of passing through the cell membrane or to make the cell membrane permeable for such an oligonucleotide.

In yet another embodiment, the oligonucleotide is coupled to a moiety, which inactivates Lgs mRNA. In a specific embodiment, the moiety inactivating mRNA is a ribozyme. In another embodiment, the pharmaceutically acceptable carrier comprises a structure, which binds to a receptor on a cell capable of being taken up by the cells after binding to the structure.

In yet another embodiment the oligonucleotide is a double stranded lgs RNA molecule. Such ribonucleic acid fragments are about 18 to about 1000 nucleotides in length, preferably from about 20 to about 500 nucleotides in length, more preferably from 20 to 50, most preferably from 20 to 22 nucleotides in length and can be derived from the nucleotides sequences shown in FIGS. 2A-2G (SEQ ID NO:1), 8A (SEQ ID NO:14) or 10A (SEQ ID NO:16).

Methods of preparing and employing antisense oligonucleotides, double stranded RNA oligonucleotides, antibodies, nucleic acid probes and transgenic animals directed to Lgs are well known by persons skilled in the art.

The invention also includes methods of screening a plurality of chemical compounds to identify a compound, which specifically inhibits binding of mammalian Lgs proteins to β-Cat, Doll (U.S. provisional application No. 60/277,976) or any interacting partner identified by methods described by the invention. These methods comprise determining whether the binding of Lgs to an interacting partner is reduced in the presence of the compound, relative to the binding in the absence of the compound.

The invention also relates to nucleotide sequences and the respective peptides derived thereof comprising at least one of the homology domains between *Drosophila* and human Lgs described in FIG. 7B (SEQ ID NOs:2-13) and the use of said peptides to block Lgs function in cancer cells. Furthermore, the present invention comprises specific compounds that bind to said domains.

BRIEF DESCRIPTION OF THE DRAWINGS

The patent or application file contains at least one drawing executed in color. Copies of this patent application publication with color drawing(s) will be provided by the Office upon request and payment of the necessary fee.

(B) Typical phenotype of animals with two mutated lgs alleles. The picture shows a pharate removed from the pupal case. Note the almost complete absence of legs, the wing to notum transformation (on the left side), and the complete lack of antennae.

(C) Intensification of the wingless lack of function phenotype by additional reduction of lgs function. These flies display notches in the wing margins (left panel), and dorsalization of ventral leg structures (right panel).

FIGS. 2A-2G The *Drosophila* lgs sequence (SEQ ID NO:1). cDNA is shown with introns from flies genomic DNA, introns are underlined. The first in-frame stop codon upstream of the ORF is underlined, the Kozak/Cavener sequence upstream of the initiator codon is marked by a bold underline, the beginning of the poly(A) tail is italicised.

The polypeptide sequence is shown in SEQ ID NO:23.

Figure 3A:
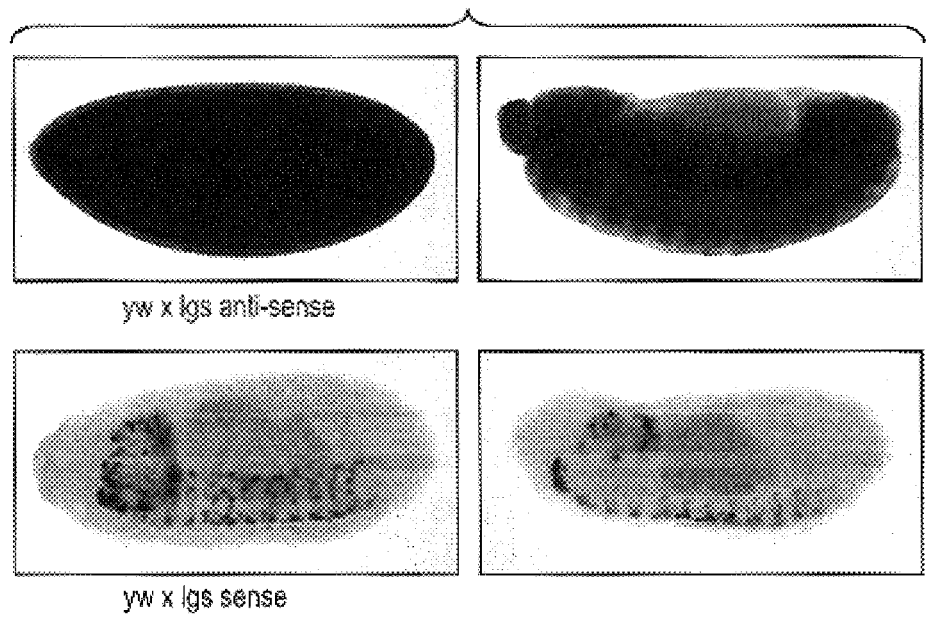
Figure 3B:
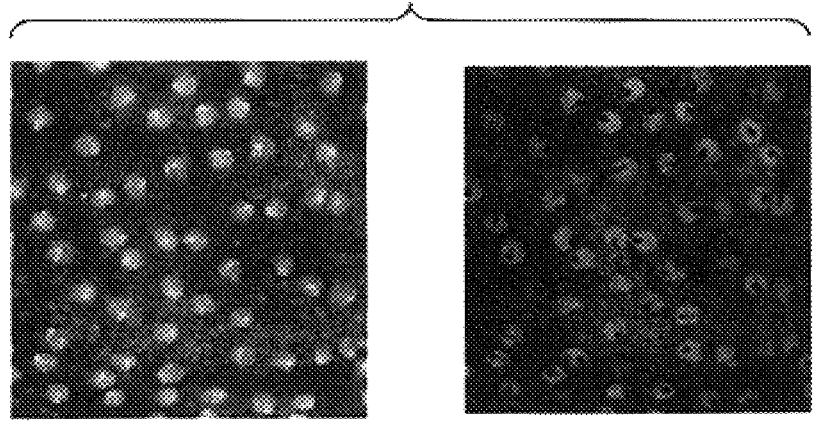

FIG. 3 (A) Lgs mRNA in situ hybridization. Lgs is maternally contributed and strongly and ubiquitously transcribed throughout embryonic development. The sense control probe reveals weaker transcription in a specific CNS pattern, probably due to repetitive elements transcribed in the opposite direction.

(B) Lgs-HA localization in peripodial membrane cells. Imaginal discs from larvae of genotype tub:lgs-HA were immunostained with mouse-anti-HA antibody and anti-mouse-FITC antibody conjugate. Lgs-HA specific staining can be seen in the nucleus (left panel). As a comparison, nuclei are specifically stained with green YO-PRO fluorescent dye (Molecular Probes) (right panel). As a background control, imaginal discs not expressing HA-tagged Lgs protein were stained in the same way (data not shown). Similar results were obtained when the anti-dLgs antibody provided by this invention was used instead of the anti-HA.

Figure 4:
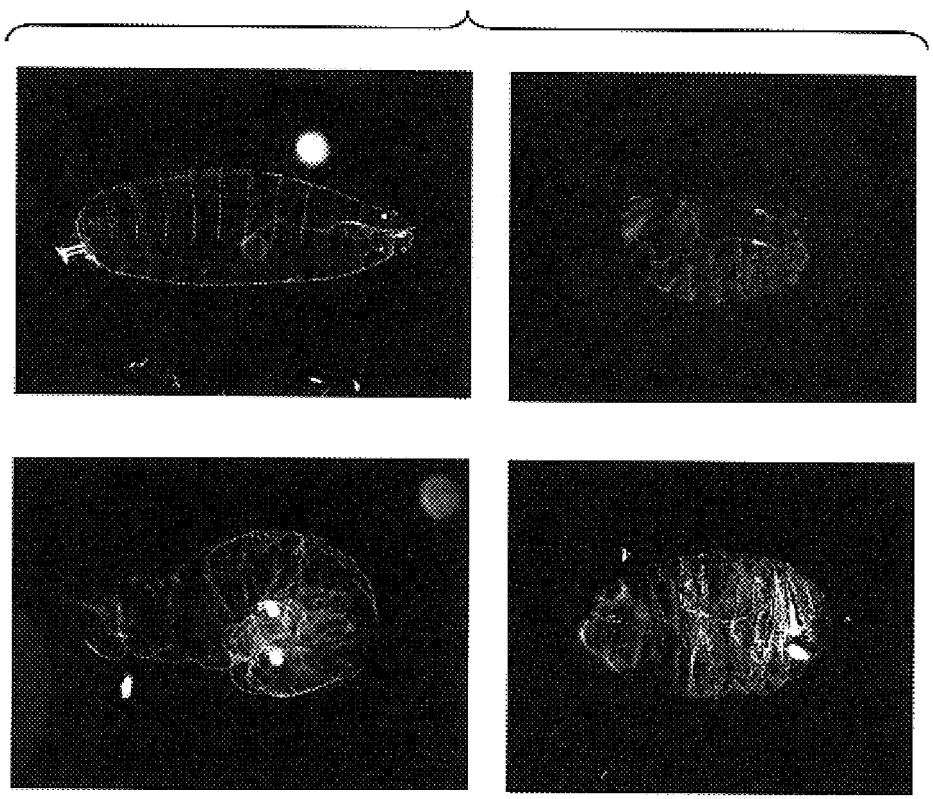

FIG. 4 Embryonic lgs mutant phenotype and epistasis analysis. Top. Cuticle preparation of larvae derived from wild type (left), and $dLgs^{17E}/dLgs^{17E}$ mutant embryo (right). The ventral epidermis of wild type larvae displays regular denticle belts, spaced by naked cuticle. No naked cuticle is observed in $dLgs^{17E}/dLgs^{17E}$ mutant animals. Bottom. The Wg signaling pathway was activated by ubiquitous expression of a constitutively active form of Arm (ΔArm) under the control of a hs-GAL4 driver. In these mutants embryo, ventral denticles are replaced by naked cuticle (left). Mutation of dLgs blocks over-activation of the Wg signaling pathway by ΔArm (right) and the phenotype is more reminiscent of wg loss of function mutations.

Figure 5A:
Figure 5B:
Figure 5C:
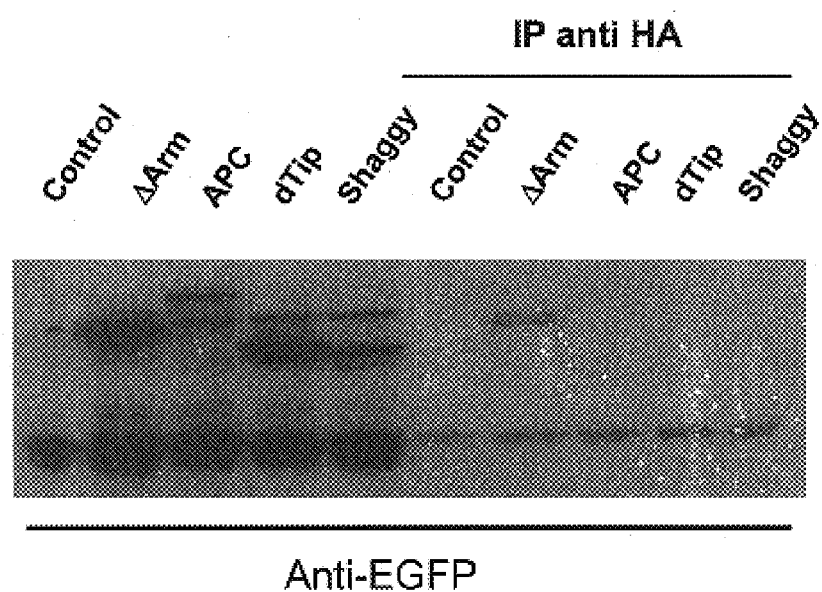

FIGS. 5 (A-B) Localization of Lgs protein in the absence and presence of NLS-Arm. HEK 293 cells were seeded into polylysine-coated 8 well chambers (Nalge-Nunc Internat.) and grown overnight at 37° C. Cells were then transfected by the lipofection method described below either with a green fluorescence tagged dLgs mammalian expression plasmid alone (FIG. 5A) or together with a mammalian expression plasmid encoding for a nuclear localization sequence tagged Arm protein (FIG. 5B). The cells were then washed and fixed with 3.7% formaldehyde in PBS for 10 min. The washing step was repeated three times for 5 min before applying coverslips using Vectashield® mounting medium (Vector Laboratories, Inc.). FIG. 5(C) Co-immunoprecipitation of Lgs protein with Arm. HEK 293 cells at 50% confluence were transfected by a lipofection method. Seven μg of DNA were diluted into 0.8 ml of OPTI-MEM Medium (Life Technologies, Inc.) and combined with 20 μl of Lipofectamine (Life Technologies, Inc.) in 0.8 ml OPTI-MEM. After incubation for 20 min, 1.6 ml of OPTI-MEM was added and the mixtures were overlaid onto monolayers of cells. After culturing at 37° C./5% $CO_2$ for 6 hr, 3 ml of OPTI-MEM containing 20% fetal calf serum (FCS) was added to the cultures. Cells were lysed 25 h after transfection in co-IP buffer (20 mM Tris HCl pH 7.5, 140 mM NaCl, 1.5 mM $MgCl_2$, 1 mM EDTA, 1 mM DTT, 1% Triton-X100, 10% glycerol, 1 mM Natrium vanadate, 50 mM NaF, and protease inhibitors). Immunoprecipitations were performed in co-IP buffer either using the rat $IgG_1$ anti-HA monoclonal antibody or the mouse anti-myc monoclonal antibody (Clone 9E10, Calbiochem) conjugated to protein G-agarose (Boehringer Mannheim). Control Immunoprecipitations were performed using rat or mouse IgG (Sigma-Aldrich). After 3 h incubation at 4° C., beads were washed 4 times in washing buffer (20 mM Tris HCl pH 7.5, 140 mM NaCl, 1.5 mM $MgCl_2$, 1 mM EDTA, 1 mM DTT, 1% Triton-X100, 1 mM Natrium vanadate, 50 mM NaF) and resuspended in 25 μl of Laemmli buffer (Sambrook, Fritsch et al. 1989). Immune complexes were analyzed by sodium dodecylsulfate polyacrylamide gel electrophoresis (SDS-PAGE) immunoblot assay using anti-GFP monoclonal antibody (Clontech Laboratories Inc.), followed by horseradish peroxidase conjugated secondary antibody (Amersham Pharmacia Biotech). Detection was performed using an enhanced chemiluminescence detection method (ECL, Amersham Pharmacia Biotech).

FIG. 5(D) Summary of the binding interactions in the yeast-two-hybrid assay. The desired cDNA were subcloned into the pLexA DNA binding domain vector (Clontech) and the pGJ4-5 activation domain vector (Clontech, sold as pAD). Yeast two hybrid was done by standard methods (Fields and Sternglanz 1994). Briefly, the appropriate pairs of plasmids were transformed together with the reporter plasmid pSH18-34 (Clontech) into the yeast strain EGY48 by the lithium acetate-polyethylene glycol method and grown on selective media. Transformants were analyzed for beta galactosidase activity as described (Fields and Sternglanz 1994). To establish reproducibility the interactions were tested in both directions. FIGS. 5(E-G) In Vitro Binding Assays. Proteins were in vitro translated (IVT) using reticulocyte lysates (TNT-lysates, Promega Corporation) containing [$^{35}$S]-methionine (Amersham Pharmacia Biotech). Glutathione S-transferase (GST) fusion proteins were immobilized on glutathione-Sepharose and blocked in binding buffer (20 mM Tris pH 8.0, 200 mM NaCl, 1 mM EDTA, 1 mM DTT, 1 mM MgCl$_2$, 10% glycerol, 0.5% NP40, 0.05% BSA, and proteinase inhibitors) for 45 min. Two µg of immobilized GST proteins were then incubated for 1.5 hrs with 0.5-4 µl of IVT proteins in binding buffer. The beads were washed four times in washing buffer (20 mM Tris pH 8.0, 200 mM NaCl, 1 mM EDTA, 1 mM DTT, 1 mM MgCl$_2$, 0.5% NP40) and boiled in Laemmli SDS sample buffer. The use of equivalent amounts of intact GST fusion proteins and successful IVT was confirmed by SDS-PAGE analysis using Coomassie staining or autoradiography, respectively.

FIG. 5(E-F) Binding of in vitro translated (IVT) Arm to GST-dLgs(1-732), GST-dLgs(733-1464) or GST alone (FIG. 5E), and of IVT Lgs to GST-Arm or GST alone (FIG. 5F).

FIG. 5(G) Binding of in vitro translated mouse β-Cat to GST-hLgs(1-732) or GST alone.

Figure 6:
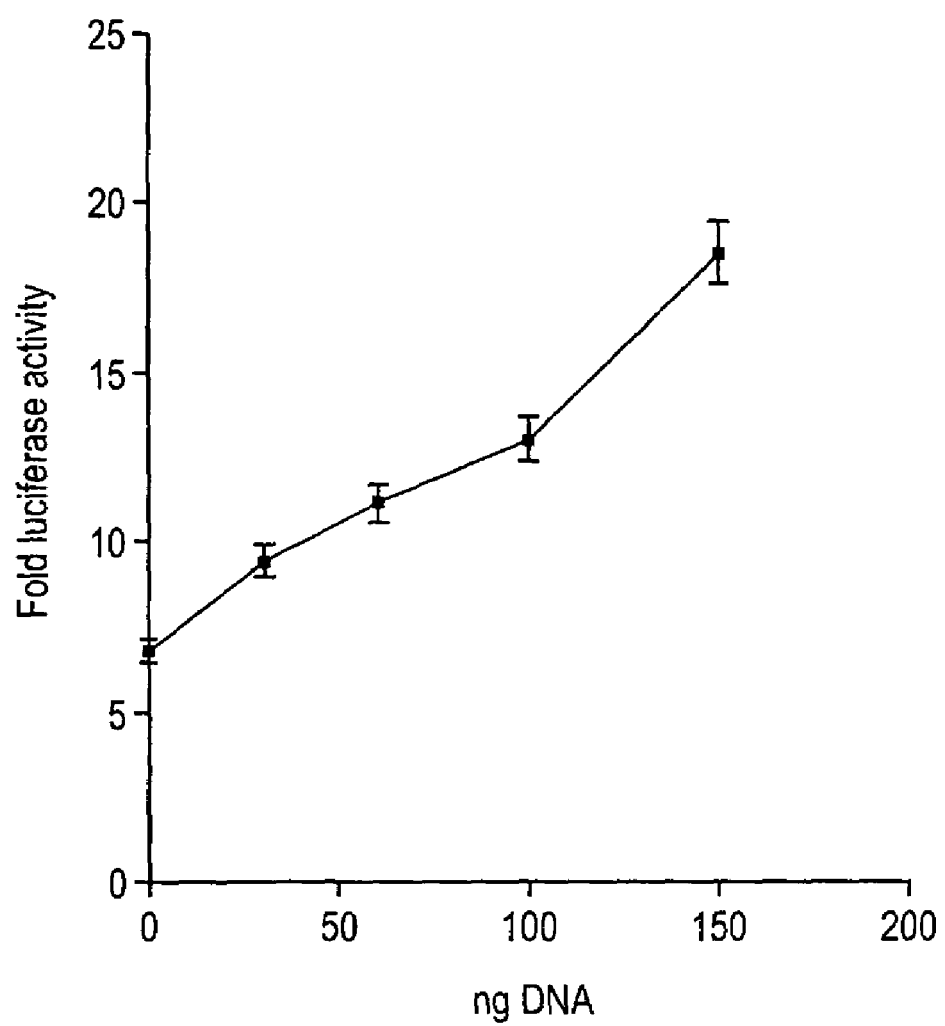

FIG. 6 Effect of Lgs on Tcf-Arm mediated transactivation of a Tcf response element driving a luciferase reporter gene. HEK293 cells at 50% confluence were transfected by a lipofection method. 450 ng of TOPFLASH luciferase reporter plasmid (Upstate biotechnology, New York, USA), 8 ng of pEGFP-Arm, 30-200 ng of pcDNA3-dLgs and 20 ng of a *renilla* luciferase reporter plasmid pRL-SV40 (Promega Corporation, Madison USA) to normalize the transfection efficiency, were diluted into 50 µl of OPTI-MEM Medium (Life Technologies, Inc.) and combined with 2.4 µl of Lipofectamine (Life Technologies, Inc.) in 50 µl OPTI-MEM. After incubation for 20 min, 0.35 ml of OPTI-MEM was added and the mixtures were overlaid onto monolayers of cells. After culturing at 37° C./5% CO$_2$ for 6 hr, 0.45 ml of OPTI-MEM containing 20% FCS was added to the cultures. Cell extracts were prepared 48 h after transfection and assayed for firefly and *renilla* luciferase activity as described by the manufacturer (Dual luciferase reporter assay system, Promega Corporation). All transfection experiments were carried out in triplicate, repeated at least three times, and normalized for *renilla* luciferase activity. Similar results are obtained using β-Cat and hLgs instead of Arm and dLgs, respectively.

FIG. 7 (A) Distribution of short local alignments (sequence homology domains) between dLgs and hLgs/Bcl9. The number of each alignment refers to FIG. 7B (SEQ ID NOs:2-13) which displays them in detail. A similar degree of homology is obtained by comparing homologues domains of dLgs and the predicted amino acid sequence of hLgs-1. hLgs/Bcl9 and hLgs display up to 95% homology in the same domains, (B) Local alignments of dLgs with hLgs/Bcl9 (SEQ ID NOs:2-13). A WWW server implementation of LALIGN (version 2.0u63 was used (matrix: pam120; gap penalties: −14/−4; alignment 4 edited by hand).

FIG. 8 The human lgs/bcl9 sequence.

(A) cDNA sequence (SEQ ID NO:14).

(B) Protein sequence (SEQ ID NO:15).

Figure 9:
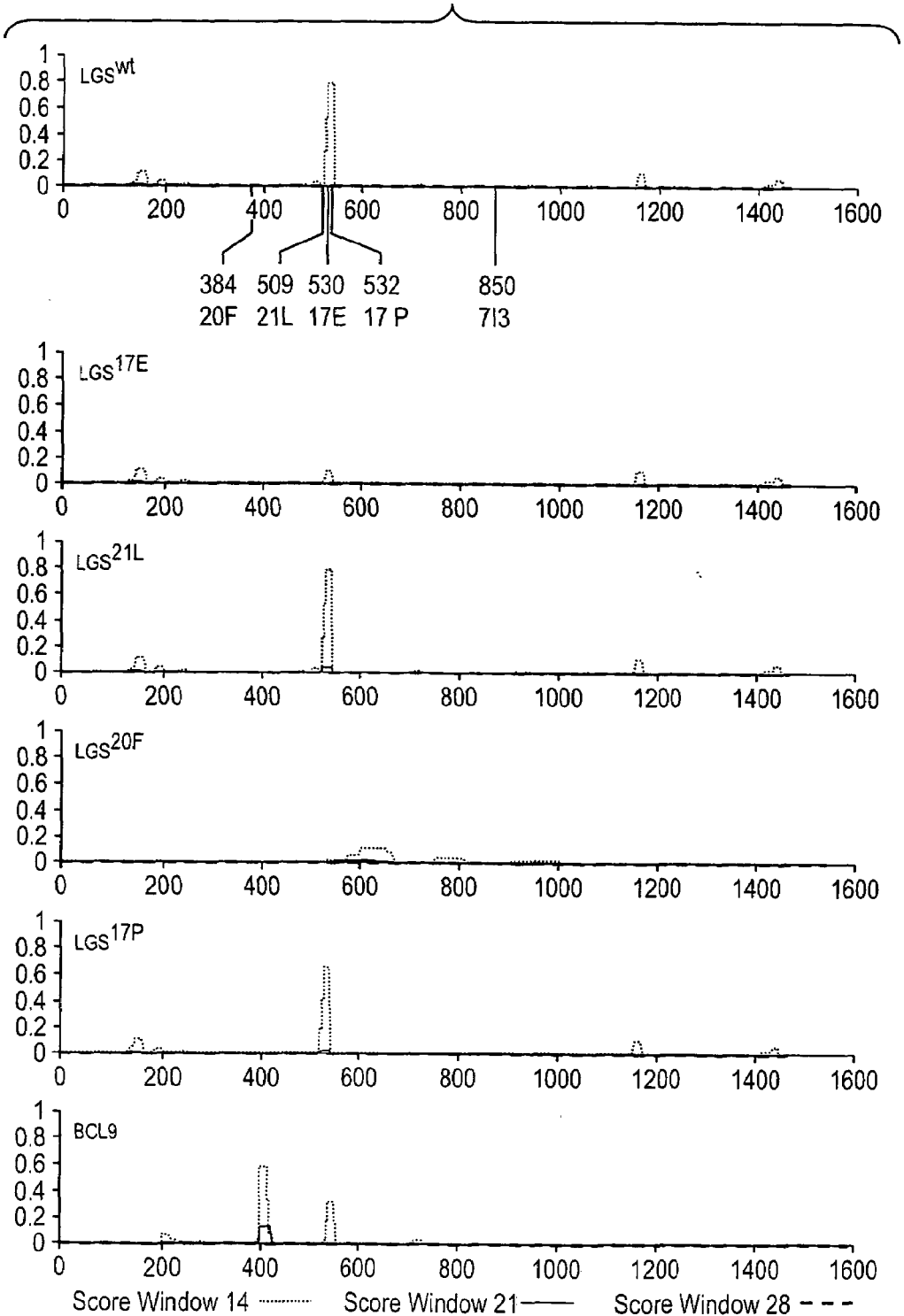

FIG. 9 Prediction of the formation of coiled-coil structures by wild type dLgs, 4 mutant dLgs forms, and hLgs/Bcl9. One occurrence of a coiled coil between amino acids 526-539 is predicted for dLgs, and the overall picture is somewhat similar for hLgs/Bcl9. The peak is lost in dLGS$^{17E}$ with the single amino acids exchange at position 531, and it is cut off by premature termination in the case of dLGS$^{20F}$. dLGS$^{17P}$ with an amino acids exchange at position 532 has a reduced score, and the homozygous viable allele dlgs$^{21L}$ with an amino acid exchange at position 509 is unaffected. A WWW server implementation of COILS version 2.1 was used with the MTDK matrix and without weights (Lupas, Van Dyke et al. 1991; Lupas 1997). All major peaks represent results obtained with a 14-residue window, the main peak also scores weakly with a 21-residue window, but nothing is detected with a 28-residue window. Remarkably, these mutated amino acids disrupting dLgs function are conserved in hLgs/Bcl9 (FIGS. 7A-7B (SEQ ID NOs:2-13)).

FIG. 10 (A) Putative hLgs/bcl9 homologue (hlgs-1) partial C-terminal cDNA (SEQ ID NO:16). Found by Blast search against hLgs/Bcl9 protein sequence. Following hs_genome/GS_mRNA was found which contains part of the hLgs-1 cDNA sequence: lcl|Hs11__9491__24__72__2. Most of the N-terminal region can be derived, e.g., from following EST: BF752124, D63746, BG116685, and the hs_genome/GS_mRNA: lcl|Hs11__9491__22__28__8 (amino acid 1-225) (www.ncbi.nlm.nih.gov/blast/Blast.cgi)

FIG. 10(B) Predicted protein (C-terminal part of hLgs-1) (fragment) (SEQ ID NO:17) derived by translation of the predicted cDNA in FIG. 10(A) (SEQ ID NO:16). The N-terminus can to be derived by translation of the EST described above. The proteins contain all lgs sequence homology domains described in FIGS. 7A-7B (SEQ ID NOs:2-13).

Figure 11A:
Figure 11B:

FIG. 11 Rescue experiments with hlgs/bcl9 in *Drosophila*. A tub:hlgs/bcl9 transgene was introduced into mutant dlgs20F/dlgs20F and dlgs17° E./dlgs21L. These mutant flies are characterized by larval or pupal lethality. Pupae lack antenna and legs and have small wings (FIG. 11A). In contrast, flies carrying the tub:hlgs/bcl9 transgene survive to adulthood and look like Lgs wild type flies (FIG. 11B). This demonstrated that hLgs can replace dLgs function in *Drosophila*.

Figure 12C:
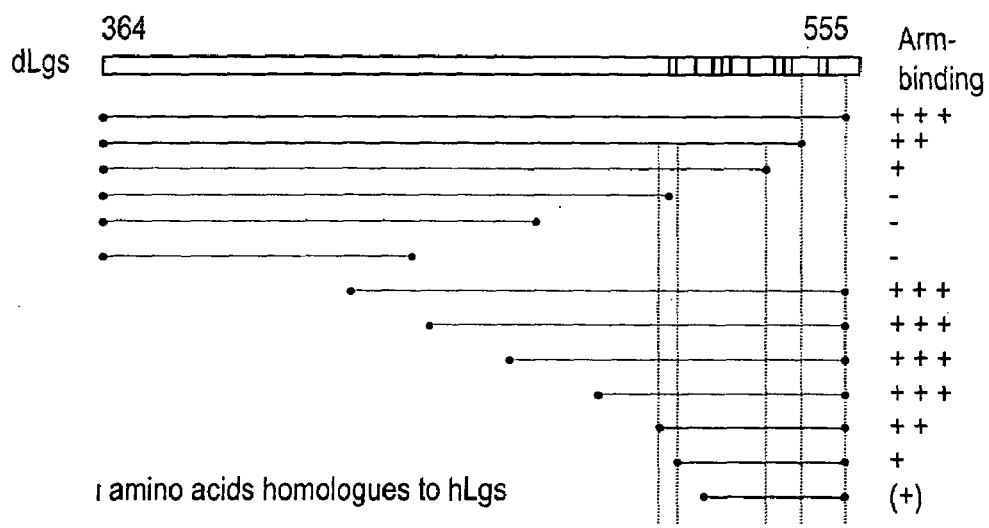
Figure 12D:
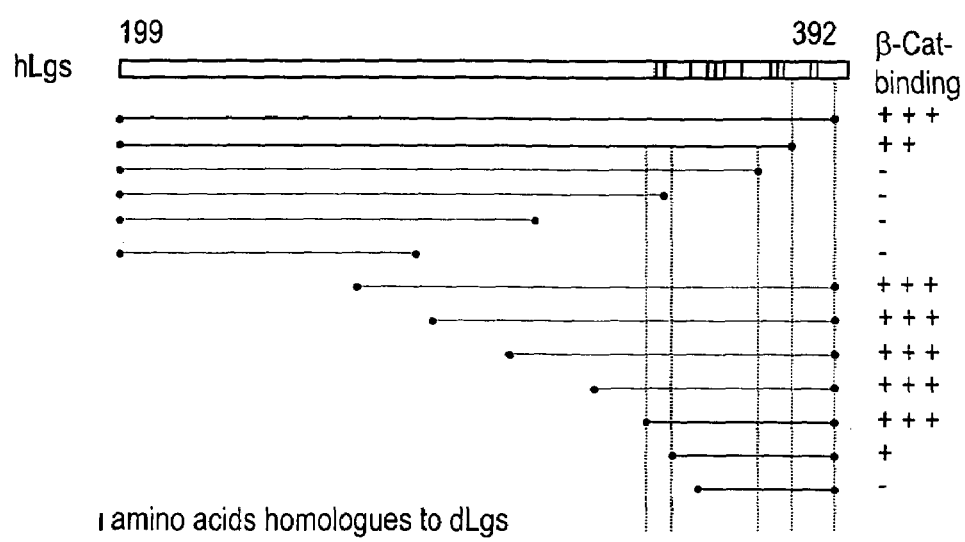
Figure 13A:
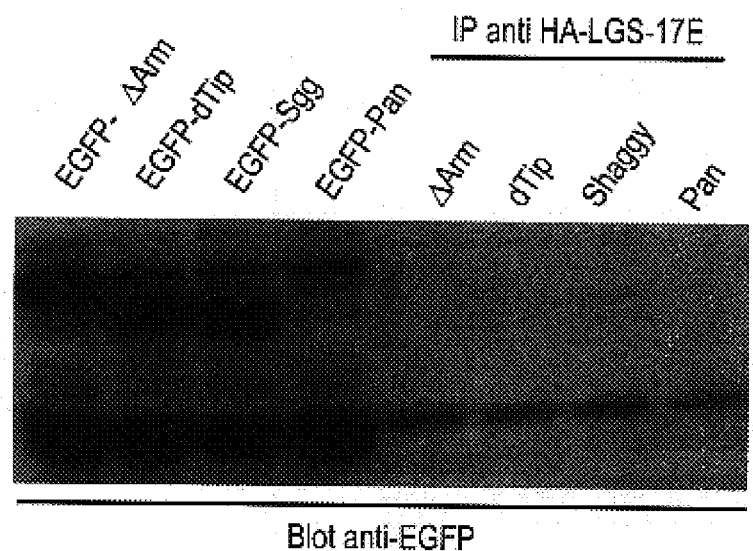
Figure 13B:
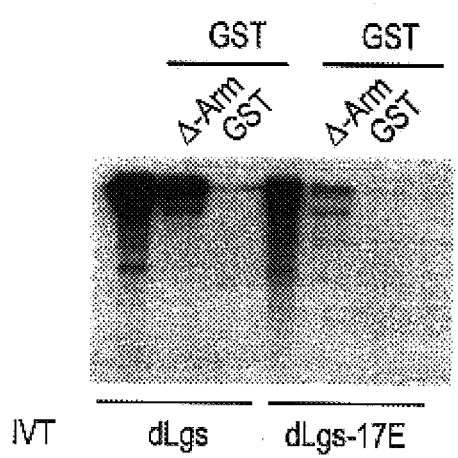
Figure 13C:
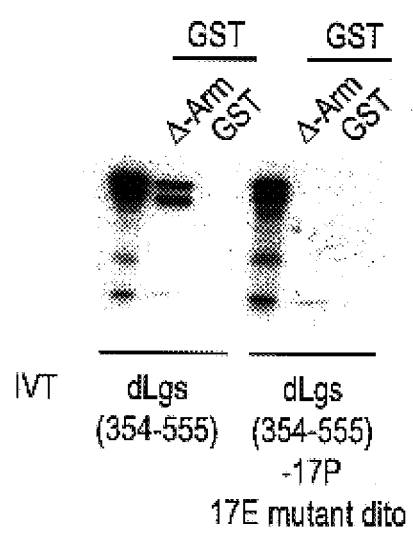
Figure 13D:
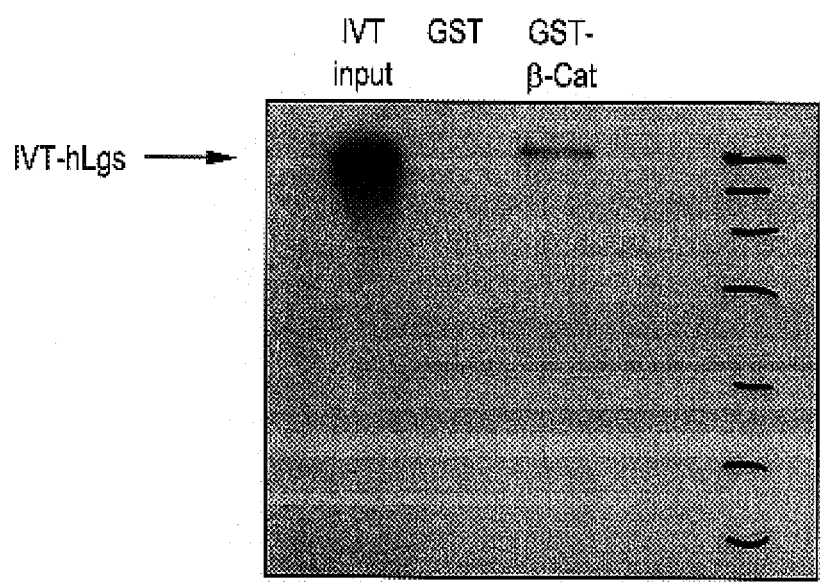
Figure 13E:
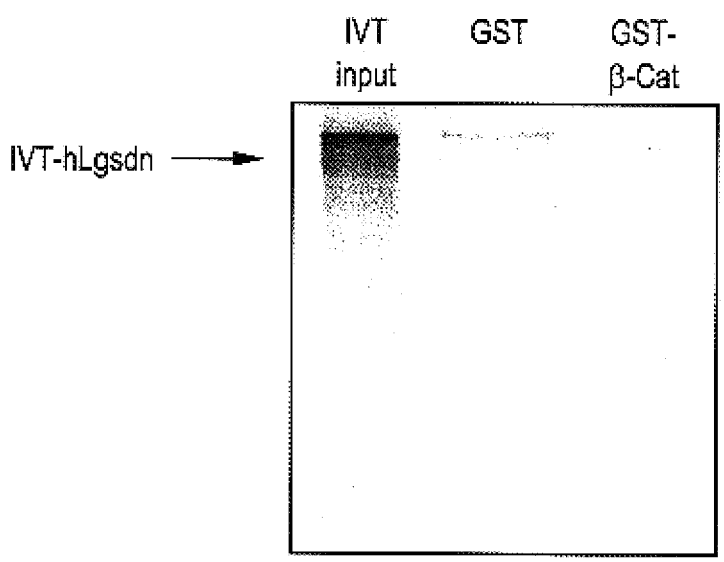

FIG. 12 (A-E) In Vitro Binding Assays, fine mapping. Proteins were in vitro translated (IVT) using reticulocyte lysates (TNT-lysates, Promega Corporation) containing [$^{35}$S]-methionine (Amersham Pharmacia Biotech). Glutathione S-transferase (GST) fusion proteins were immobilized on glutathione-Sepharose and blocked in binding buffer (20 mM Tris pH 8.0, 200 mM NaCl, 1 mM EDTA, 1 mM DTT, 1 mM MgCl$_2$, 10% glycerol, 0.5% NP40, 0.05% BSA, and proteinase inhibitors) for 45 min. Two µg of immobilized GST proteins were then incubated for 1.5 hrs with 0.5-4 µl of IVT proteins in binding buffer. The beads were washed four times in washing buffer (20 mM Tris pH 8.0, 200 mM NaCl, 1 mM EDTA, 1 mM DTT, 1 mM MgCl$_2$, 0.5% NP40) and boiled in Laemmli SDS sample buffer. The use of equivalent amounts of intact GST fusion proteins and successful IVT was confirmed by SDS-PAGE analysis using Coomassie staining or autoradiography, respectively. FIGS. 12(A-B) Binding of IVT dLgs fragments to GST-Arm (FIG. 12A), and of IVT ΔArm to GST-dLgs-fragments (FIG. 12B). FIGS. 12(C-D) Precise mapping of the Arm binding sites in dLgs (FIG. 12C), and of the β-Cat binding sites in hLgs (FIG. 12D). The figures depict the binding of in vitro translated dLgs and hLgs fragments to GST-Arm and GST-β-Cat, respectively. The minimal protein fragment, which still binds to Arm or β-Cat comprises the dLgs-hLgs sequence homology domain 2 of FIGS. 7A-7B (SEQ ID NOs:4-5). FIG. 12(E) Precise mapping of the Lgs binding sites in Arm. In vitro translated Arm fragments were tested for their binding to GST-dLgs(1-732).

FIG. 13(A-E) Binding of mutants dLgs and hLgs to Arm/β-Cat. FIG. 13(A) Co-immunoprecipitation of mutant HA-dLgs-17E protein with GFP fused-Arm, -dTip, -dAPC and -Shaggy. HEK293 cells at 50% confluence were transfected by a lipofection method. Seven µg of DNA were diluted into 0.8 ml of OPTI-MEM Medium (Life Technologies, Inc.) and combined with 20 µl of Lipofectamine (Life Technologies, Inc.) in 0.8 ml OPTI-MEM. After incubation for 20 min, 1.6 ml of OPTI-MEM was added and the mixtures were overlaid onto monolayers of cells. After culturing at 37° C./5% CO$_2$ for 6 hr, 3 ml of OPTI-MEM containing 20% fetal calf serum (FCS) was added to the cultures. Cells were lysed 25 h after transfection in co-IP buffer (20 mM Tris HCl pH 7.5, 140 mM NaCl, 1.5 mM MgCl$_2$, 1 mM EDTA, 1 mM DTT, 1% Triton-X100, 10% glycerol, 1 mM Natrium vanadate, 50 mM NaF, and protease inhibitors). Immunoprecipitations were performed in co-IP buffer either using the rat IgG$_1$ anti-HA monoclonal antibody or the mouse anti-myc monoclonal antibody (Clone 9E10, Calbiochem) conjugated to protein G-agarose (Boehringer Mannheim). Control Immunoprecipitations were performed using rat or mouse IgG (Sigma-Aldrich). After 3 h incubation at 4° C., beads were washed 4 times in washing buffer (20 mM Tris HCl pH 7.5, 140 mM NaCl, 1.5 mM MgCl$_2$, 1 mM EDTA, 1 mM DTT, 1% Triton-X100, 1 mM Natrium vanadate, 50 mM NaF) and resuspended in 25 µl of Laemmli buffer. Immune complexes were analyzed by SDS-PAGE/immunoblot assay using anti-GFP monoclonal antibody (Clontech Laboratories Inc.), followed by horseradish peroxidase conjugated secondary antibody (Amersham Pharmacia Biotech). Detection was performed using an enhanced chemiluminescence detection method (ECL, Amersham Pharmacia Biotech). FIGS. 13(B-E) In Vitro Binding Assays. Proteins were in vitro translated (IVT) using reticulocyte lysates (TNT-lysates, Promega Corporation) containing [$^{35}$S]-methionine. Glutathione S-transferase (GST) fusion proteins were immobilized on glutathione-Sepharose and blocked in binding buffer (20 mM Tris pH 8.0, 200 mM NaCl, 1 mM EDTA, 1 mM DTT, 1 mM MgCl$_2$, 10% glycerol, 0.5% NP40, 0.05% BSA, and proteinase inhibitors) for 45 min. Two µg of immobilized GST proteins were then incubated for 1.5 hrs with 0.5-4 µl of IVT proteins in binding buffer. The beads were washed four times in washing buffer (20 mM Tris pH 8.0, 200 mM NaCl, 1 mM EDTA, 1 mM DTT, 1 mM MgCl$_2$, 0.5% NP40) and boiled in Laemmli SDS sample buffer. The use of equivalent amounts of intact GST fusion proteins and successful IVT was confirmed by SDS-PAGE analysis using Coomassie staining or autoradiography, respectively. FIGS. 13 (B-C) Binding of IVT wild type dLgs and dLgs-17E mutant to GST-ΔArm or GST alone (FIG. 13B), and of IVT wild type dLgs(354-555) or dLgs(354-555)-17E and -17P mutants to GST-ΔArm or GST alone (FIG. 13C). FIGS. 13(D-E) Binding of IVT wild type hLgs/Bcl9 to GST alone or GST-β-Cat (FIG. 13D) and of IVT hLgs(Δ345-385) (also named hLgsdn) to GST alone or GST-β-Cat (FIG. 13E). Mutations in the conserved amino acids of the sequence homology domain 2 of FIGS. 7A-7B (SEQ ID NOs:4-5) abolish binding of Lgs to Arm and β-Cat.

Figure 14A:
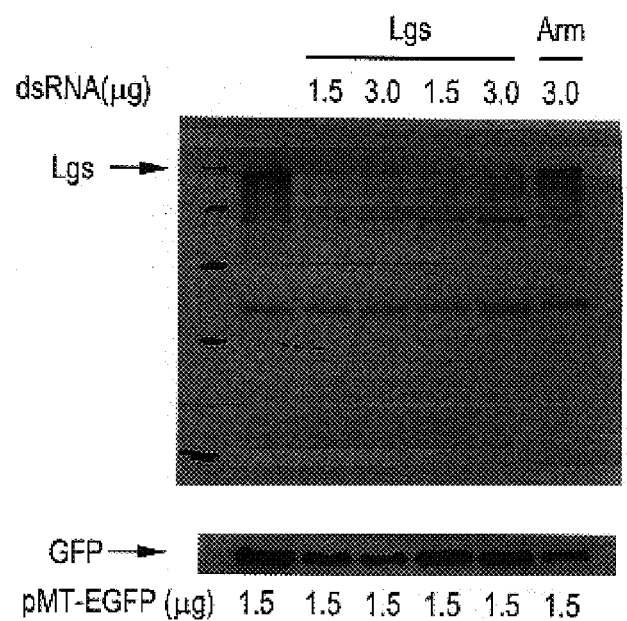
Figure 14B:
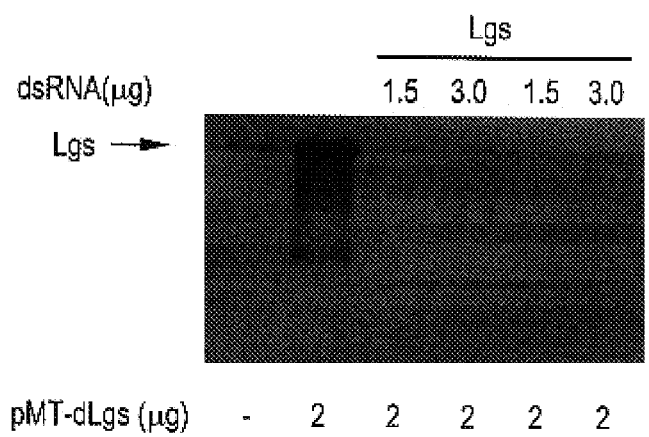

FIGS. 14(A-B) Down-regulation of dLgs protein levels by RNA interference. dLgs dsRNA was synthesized by PCR from pBS-dLgs (full length cDNA) using the T7 promoter containing dsRNA-Lgs-R1 (TAATACGACTCACTAT-AGGGAGACCACTTCCATGCTCATTTCGTCATTA (SEQ ID NO:18)) and dsRNA-Lgs-F1 (TAATACGACT-CACTATAGGGAGACCACTAGGATCTCTC-GACAACAATG (SEQ ID NO:19)) primers. As a control a PCR fragment was amplified from Arm cDNA using following primers: F primer (TAATACGACTCACTATAGG-GAGACCACACAAGACCAAGTGGACGATATG (SEQ ID NO:20)), R Primer (TAATACGACTCACTATAGG-GAGACCACAATTTGCAAGCAATCTGTGAC (SEQ ID NO:21)).

The amplified 700 base pairs products were purified using the PCR-Purification kit from Quiagen and the DNA was eluted with 50 µl water. The DNA concentration was determined by UV absorption. The RNA synthesis reaction was then performed in 50 µl volume with 1 µg of the purified PCR products using the MEGAscript™ kits from Ambion. The DNA templates were removed with RNase-free DNAase and the dsRNAs were purified by phenol-chloroform extraction and ethanol precipitation. The RNAs became double-stranded during the synthesis reaction as confirmed by native agarose gel electrophoresis in TBE. For the RNA interference experiments, S2 cells were propagated in Schneider S2 Drosophila medium (GIBCO) supplemented with 10% FCS. One day before transfection one million cells were seeded into 6 well plates and grown overnight at 25° C. A total of 5 µg DNA and dsRNA was complexed with 20 µl of CellFectine lipid mix (GIBCO) in 1.2 ml serum free growth medium (DES expression medium, Invitrogen, Carlsbad, USA). As a control, EGFP (Clontech Laboratories Inc., Palo Alto, USA) protein was expressed in the same cells under the control of the methallothionin promoter (vector used: pMT-V5/HISB, Invitrogen). The complexes were incubated for 15 minutes at RT and then added to the cells from which the normal growth medium was replaced with 1 ml serum free medium. Four hour later 1.2 ml growth medium supplemented with 30% FCS was added to the cells. One day after transfection the medium was replaced with fresh medium with 10% FCS. Where an expression plasmid under the control of the insect metallothionin promoter (pMT/V5-HisB, Invitrogen) was transfected together with the dsRNA, copper sulfate was added to the cells to a final concentration of 0.5 mM. Cells were lysed in RIPA buffer 2 days after transfection. The cleared lysates were analyzed by SDS-PAGE/immunoblot assay using anti-Lgs polyclonal antiserum described herein and anti-GFP monoclonal antibody (Clontech Laboratories Inc.), followed by horseradish peroxidase conjugated secondary antibody (Amersham Pharmacia Biotech). Detection was performed using an enhanced chemiluminescence detection method (ECL, Amersham Pharmacia Biotech). (FIG. 14A) Downregulation of endogenous Lgs expression by Lgs dsRNA. As a control, cells were treated with Arm dsRNA. EGFP expression is not affected by the treatment with lgs dsRNA. (FIG. 14B) Downregulation of exogeneous dLgs expression. dLgs levels are brought under endogeneous levels by Lgs dsRNA treatment.

Figure 15A:
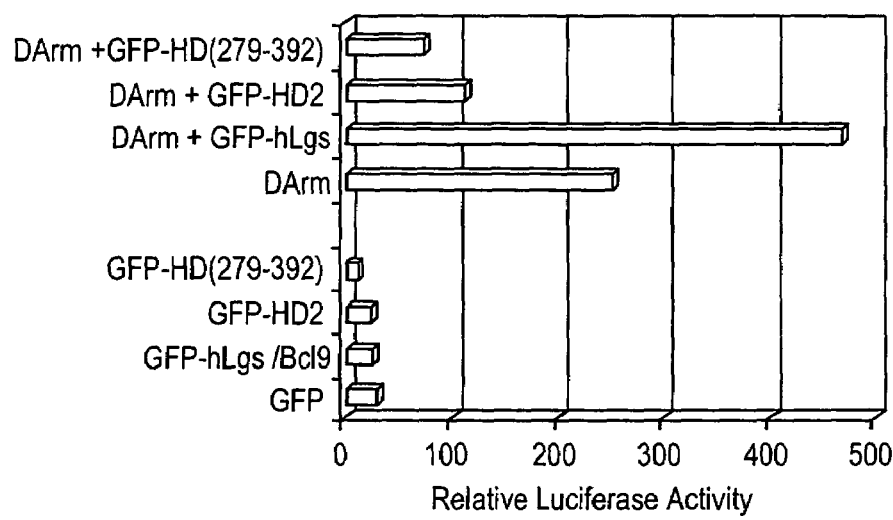

FIG. 15 (A) Effect of the expression of Lgs sequence homology 2-peptides on Tcf transcriptional activity. HEK293 cells at 50% confluence were plated into 24-well plates and transfected by a lipofection method. 240 ng of TOPFLASH luciferase reporter plasmid (Upstate biotechnology, New York, USA), 4 ng of pcDNA3-ΔArm, 200 ng of pcDNA3-EGFP-Lgs-peptide and 10 ng of a renilla luciferase reporter plasmid pRL-SV40 (Promega Corporation, Madison USA) were diluted into 25 µl of OPTI-MEM Medium (Life Technologies, Inc.) and combined with 1.2 µl of Lipofectamine (Life Technologies, Inc.) in 25 µl OPTI-MEM. After incubation for 20 min, 0.175 ml of OPTI-MEM was added and the mixtures were overlaid onto monolayers of cells. After culturing at 37° C./5% $CO_2$ for 6 hr, 0.225 ml of OPTI-MEM containing 20% FCS was added to the cultures. Cell extracts were prepared 48 h after transfection and assayed for firefly and renilla luciferase activity as described by the manufacturer (Dual luciferase reporter assay system, Promega Corporation). All transfection experiments were carried out in triplicate, repeated at least three times, and normalized for renilla luciferase activity. (B) Effect of Lgs HD2 peptides on Tcf-driven luciferase activity in SW480 colon carcinoma cells (American Tissue Culture Collection, ATCC). In these cancer cells the Wnt pathway is constitutively active due to a mutation in the APC tumor suppressor gene. As a positive control, a dominant negative hTcf4 (dnTcf4) protein was used [Roose, 1999 #187]. Cells were transfected as described above but using Lipofectamine 2000 (GIBCO Life Technologies) instead of Lipofectamine following the manufacturer recommendations.

DETAILED DESCRIPTION OF THE INVENTION

The Wnt signaling cascade is essential for the development of both invertebrates and vertebrates, and has been implicated in tumorogenesis. The Drosophila wg genes are one of the best characterized within the Wnt-protein family, which includes more than hundred genes. In the Drosophila embryo, wg is required for formation of parasegment boundaries and for maintenance of engrailed (en) expression in adjacent cells. The epidermis of embryo defective in wg function shows only a rudimentary segmentation, which is reflected in an abnormal cuticle pattern. While the ventral cuticle of wild type larvae displays denticle belts alternating with naked regions, the cuticle of wg mutant larvae is completely covered with denticles. During imaginal disc development, wg controls dorso-ventral positional information. In the Leg disc, wg patters the future leg by the induction of ventral fate (Struhl and Basler 1993). In animals with reduced wg activity, the ventral half of the leg develops into a mirror image of the dorsal side (Baker 1988). Accordingly, reduced wg activity leads to the transformation of wing to notal tissue, hence the name of the gene (Sharma and Chopra 1976). In the eye disc, wg suppresses ommatidial differentiation in favor of head cuticle development, and is involved in establishing the dorso-ventral axis across the eye field (Heberlein, Borod et al. 1998).

Additional genes have been implicated in the secretion, reception or interpretation of the Wg signaling. For instance, genetic studies in Drosophila revealed the involvement of frizzled (Dfz), dishevelled (dsh), shaggy/zeste-white-3 (sgg/zw-3), armadillo (arm), adenomatous polyposis coli (apc), axin, and pangolin (pan) in wg signaling. The genetic order of these transducers has been established in which Wg acts through Dsh to inhibit Sgg, thus relieving the repression of Arm by Sgg, resulting in the cytoplasmic accumulation of Arm and its translocation to the nucleus. In the nucleus Arm interacts with Pan to activate transcription of target genes. Vertebrate homologues have been identified for all these components (for an updated review see (Peifer and Polakis 2000)), suggesting that novel identified members of the Drosophila signaling pathway may likely have vertebrate counterparts.

Mutations leading to nuclear accumulation of the mammalian homologue of Arm, β-Cat, and consequently to constitutive activation of the Wnt pathway have been observed in many type of cancers, including colon, breast, skin, tyroid, medulloblastoma, and head and neck cancer (Morin 1999; Polakis, Hart et al. 1999). Currently, there are no known therapeutic agents effectively inhibiting β-Cat transcriptional over-activation in these cancers. This is partly due to the fact that many of the essential components required for β-Cat full activation, nuclear translocation and for its role in transcription of target genes are still unknown.

Figure 1A:
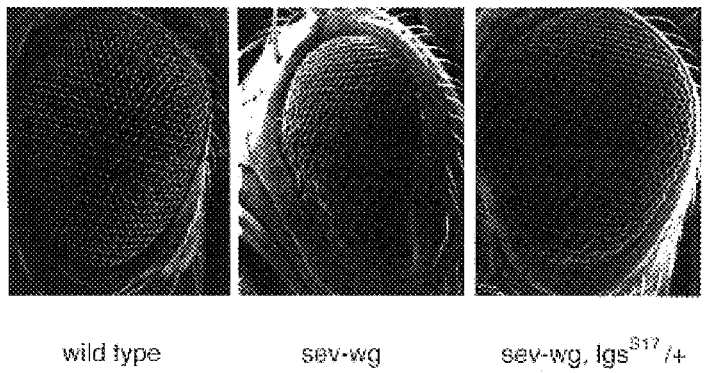
FIG. 1 (A) Scanning electron micrographs of a wild type eye (left), a sevenless-wingless transgenic eye (centre), and an eye carrying the same transgene plus a loss of function lgs allele. Note the restoration of the hexagonal array of the ommatidia by mutant Lgs.
Figure 1B:
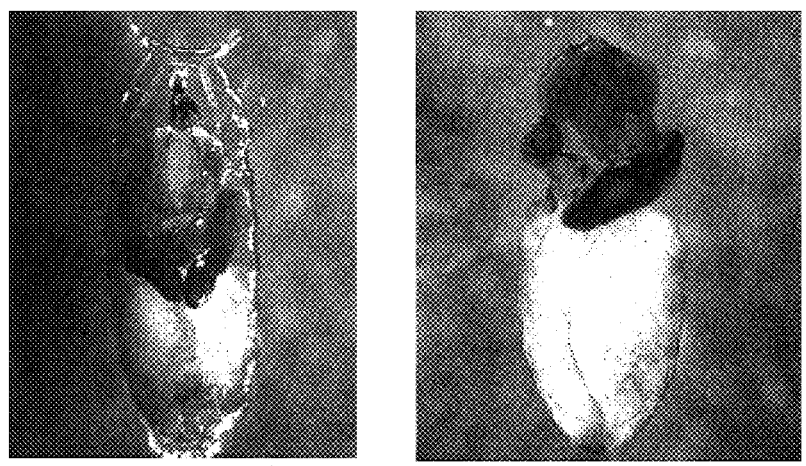
Figure 1C:
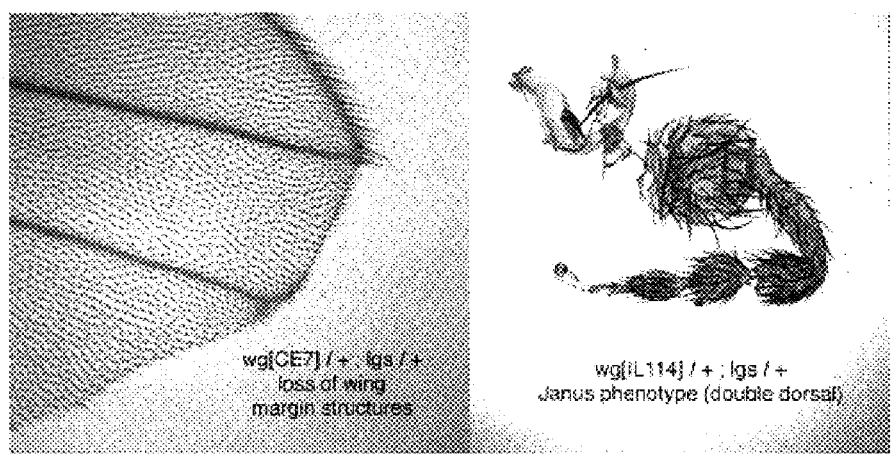

In order to identify new positive acting components of Wg signaling pathway Drosophila genetic was used. Methods to generate a particular genetically modified Drosophila strain and how to screen for specific mutations in a define signaling pathway are well known by people skilled in the art and are not part of this invention.

dLgs was found in a genetic screen for dominant suppressors of the rough eye phenotype induced by a transgene which drives ectopic wg expression under the control of the sevenless (sev) promoter during eye development in Drosophila (Brunner 1997) (FIG. 1). dLgs mRNA is maternally contributed and strongly and ubiquitously expressed during all the developmental stages (FIG. 3A). Consequently, embryos lacking both embryonal and maternal dlgs are characterized by a strong segment polarity phenotype, while weaker loss of function dlgs mutants display pupal lethality with transformation of sternites to pleura and a partial or complete loss of the antennae and the legs (hence its name). The wings of these animals are usually not affected, but are occasionally transformed into secondary notum (FIG. 1). The fact that similar phenotypes are caused by loss of function of wg, dsh and arm confirmed the essential role of lgs in the Wg signaling pathway.

dLgs is located on the fourth chromosome. The dlgs gene was cloned by positional cloning and genomic walk, techniques frequently used by persons skilled in the art. Dlgs encodes for a 1464 amino acid protein of an expected molecular mass of 153 kDa. The dLgs protein is predicted to be predominantly hydrophilic and positively charged with a small hydrophobic stretch around amino acid 300 (FIGS. 2A-2G (SEQ ID NO:1)). Neither obvious dLgs homologue nor any characterized functional motif can be found by common search tools (dot.imgen.bcm.tmc.edu:9331). However, by modification of the standard search parameters, several short stretches of amino acids within the dLgs protein are found to be highly homologue to a human protein, known as Bcl9, which has been linked to the development of B-cell lymphoma (Willis, Zalcberg et al. 1998; Busson-Le Coniat, Salomon-Nguyen et al. 1999), and to several translated EST coming from a predicted gene on chromosom 11. Interestingly, Bcl9, from now on named hLgs/Blc19, displays similar structural feature compared to dLgs, like length, hydrophility and the presence of a predicted coiled region (FIG. 9). In addition, it is remarkable that the short stretches of homology occur in a similar spacing and in the same succession as in dLgs (FIG. 7A). As we show below, despite the overall very modest homology, hLgs/Bcl9 revealed to be the true functional human homologue of dLgs, and its function, as well as any lgs homologues, is hence part of the present invention.

In order to gain further biochemical and functional insight into the role of Lgs in the Wg/Wnt signaling pathway, we screened for potential interaction partners. The data presented herein (see examples) show that dLgs but not loss of function dLgs mutants, physically interacts with Arm and Doll (For Doll interaction see U.S. provisional application No. 60/277,976). In contrast, no interaction can be detected with other Wg pathway components such as dAPC and Shaggy. Accordingly, epistasis experiments in Drosophila embryo clearly place dLgs at the same level or downstream of Arm (FIG. 4).

The interaction with Arm is also confirmed in mammalian cells, where dLgs can be directed to the nucleus in the presence of nuclear but not cytoplasmic Arm (FIG. 5A). Moreover, when co-transfected with Arm, Lgs increases the transcriptional activity of hTcf (see examples and FIG. 6). Similarly, we report herein the binding of hLgs/Bcl9 to β-Cat and its effect on β-Cat dependent transcriptional activation. We also demonstrate that dLgs and hLgs bind Arm and β-Cat, respectively, with the homology region No. 2 described in FIGS. 7A-7B (SEQ ID NOs:4-5), and that the homology region No. 1 is also essential for Lgs function (since it binds to Doll, another essential component of the Wg/Wnt pathway (provisional patent application No. 60/221,502).

Methods and vectors to achieve such results are well known in the art, and are reported herein by mean of examples.

In summary, the biochemical interactions demonstrated herein between dLgs and Arm and between their human homologues hLgs/Bcl9 and β-Cat, respectively, in conjunction with a Tcf-activation assay, complement genetic studies in Drosophila and indicate that Lgs proteins are positive regulators of the Wg/Wnt signaling pathway and are required for β-Cat dependent gene activation. Importantly, since Lgs is involved in late events of the Wg/Wnt signaling cascade, blocking its function, e.g., by interfering with its interaction with β-Cat or Doll, would result in blockade of the Wnt signal propagation, also where β-Cat is out of control due to oncogenic mutations in such a pathway. Consequently, this invention also relates to therapeutic and diagnostic methods and compositions based on Lgs proteins and their homologues as well as the respective nucleic acids or fragments thereof. In particular, the invention provides for treatment of disorders of cell fate, differentiation or proliferation involving the Wnt pathway by administration of a therapeutic compound of the invention. Such therapeutic compounds include but are not limited to: Drosophila and vertebrate Lgs protein homologues or fragments thereof, antibodies or antibody fragments thereto, lgs antisense DNA or RNA, lgs double stranded RNA, and any chemical or natural occurring compound interfering with Lgs function, synthesis or degradation.

The invention also includes methods of screening a plurality of chemical compounds to identify a compound, which specifically inhibits binding of mammalian Lgs proteins to β-Cat, Doll (U.S. provisional application No. 60/277,976) or any positive acting, interacting partner identified by methods described by the invention. These methods comprise, but they are not limited to, determining whether the binding of Lgs to an interacting partner is reduced in the presence of the compound, relative to the binding in the absence of the compound. Such assays can be performed in vivo or in vitro. If an in vivo assay is used, then the interacting proteins have to be fused, e.g., to a protein which allow the detection of such interaction. Such an example are mammalian or yeast two hybrid assays or methods measuring the energy transfer between a donor and an acceptor protein in vivo. If an in vitro assay is to be used, several methods are available to persons skilled in the art. These include but are not limited to fluorescent resonance energy transfer based methods (Kolb, Burke et al. 1997; Sittampalam, Kahl et al. 1997). All the methods indicated in this context are well known by people skilled in the art.

The invention also relates to Lgs nucleotide sequences and the respective peptides derived thereof comprising at least one of the homology domains between Drosophila and human Lgs described in FIGS. 7A-7B (SEQ ID NOs:2-13) and the use of said peptides to block Lgs function in cancer cells. Suitable techniques are known in the art for administering peptide to tumors. This can be achieved by direct administration of the peptide itself together with an appropriate pharmaceutical preparation which allow the penetration of such peptides into cells, or by mean of a gene therapy format. The latter bases of the administration of a DNA sequence coding for the peptide using suitable expression vectors. Such vectors are known in the art and it is in the skill of the artisan to select an appropriate one. In the tumor cells, the peptides will bind to their interaction partner, e.g., β-Cat if the homology domain 2 peptide is chosen, and titrate it away from the endogenous Lgs proteins thus preventing expression of target genes by uncontrolled β-Cat.

The above disclosure generally describes the present invention. A more complete understanding can be achieved by the following specific examples, which are provided herein for purposes of illustration only, and are not intended to limit the scope of the invention.

1. Definitions

The terms "Lgs sequence", "Lgs polypeptide", "Lgs protein" when used herein encompasses native vertebrate and invertebrate Lgs and Lgs variant sequences (which are further defined herein).

A "wild type Lgs sequence" comprises a polypeptide having the same amino acid sequence as a Lgs protein derived from nature. Such wild type sequence of Lgs can be isolated from nature or produced by recombinant and/or synthetic means. The term "wild type sequence Lgs" specifically encompasses naturally occurring truncated forms, naturally occurring variant forms (e.g., alternatively spliced forms) and naturally occurring allelic variants of Lgs. In one embodiment of the invention, the native Lgs sequence is a mature or full-length Lgs sequence comprising amino acids 1 to 1464 of FIGS. 2A-2G (SEQ ID NO:1) or amino acids 1 to 1394 of FIG. 8B (SEQ ID NO:15).

"Lgs variant" means an active Lgs, having at least about 50% amino acid sequence identity with the amino acid sequence of residue 1 to 1464 of the Drosophila Lgs polypeptide of the sequence of FIGS. 2A-2G (SEQ ID NO:1) or amino acids 1 to 1394 of FIG. 8B (SEQ ID NO:15). The term "lgs variant" however, does also include functional homologues of Lgs in the Wnt pathway.

"Percent (%) amino acid sequence identity" with respect to the Lgs sequences identified herein is defined as the percentage of amino acid residues in a candidate sequence that is identical with the amino acid residues in the Lgs sequence described herein, after aligning the sequence and introducing gaps, if necessary, to achieve the maximum percentage sequence identity, and not considering any conservative amino acid substitution as part of the sequence identity. The % identity values used herein can be generated by WU-BLAST-2, which was obtained from (Tatusova TA 1999). WU-BLAST-2 uses several search parameters, most of which are set to the default values.

The term "positive", in the context of sequence comparison performed as described above, includes residues in the sequence compared that are not identical but have similar properties (e.g., as a result of a conservative substitution). The % value of positive is determined by the fraction of residues scoring a positive value in the BLOSUM 62 matrix divided by the total number of residues in the longer sequence as defined above.

In a similar manner, "percent (%) nucleic acid sequence identity" with respect to the coding sequence of the Lgs polypeptides identified herein is defined as the percentage of nucleotide residues in a candidate sequence that are identical with the nucleotide residues in the Lgs coding sequence. The identity values used herein can be generated using BLAST module of WU-BLAST-2 set to the default parameters.

The term "epitope tag" refers to a chimeric polypeptide comprising a Lgs polypeptide fused to a "tag polypeptide". The tag polypeptide has enough residues to provide an epitope against which an antibody can be made, yet is short enough that it does not interfere with the activity of the Lgs polypeptide to which it is fused.

Nucleic acids are "operably linked" when they are placed in a functional relationship with another nucleic acid sequence.

The term "epistasis" means hierarchy in gene action. Epistasis experiments are performed to place components of a signaling pathway in the right order.

The term "rescue experiments" are designed to determine which gene is responsible for a specific mutant phenotype. Specifically, mutant embryos are injected with coding or genomic DNA, and the effect of the introduced DNA is determined on the basis of the capacity to revert the mutant phenotype.

"Active" or "activity" refers to forms of Lgs polypeptides that retain the biological and/or immunological activity. A preferred activity includes for instance the ability to positively modulate the Wnt signaling pathway.

The term "antagonist" is used in a broad sense, and includes any molecule that partially or fully inhibits, blocks or neutralizes a biological activity of Lgs polypeptides described herein. In a similar way, the term "agonist" is used in the broadest sense and includes any molecule that mimics a biological activity of an active Lgs polypeptide.

"Treatment" refers to both therapeutic treatments and prophylactic or preventive measures, wherein the objective is to prevent or slow down the targeted pathologic condition or disorder. Those in need of treatment include those already with the disorder as well as those prone to have the disorder or those in whom the disorder is to be prevented.

2. General Methods

EXAMPLE I

Isolation of Lgs cDNA a) *Drosophila* Lgs:

Lgs was found by positional cloning. A *Drosophila* genomic region of about 150 kDa was cloned, and by a combination of genetic and molecular methods known in the art, the region containing the gene was reduced to 75 kDa. dLgs was then identified by the analysis of mutant sequences and by rescue experiments. Alternatively, lgs primers can be used to screen cDNA libraries as described in (Sambrook, Fritsch et al. 1989).

b) Human Lgs:

Human Lgs was identified by searching a public sequence database (www.ch.embnet.org/software/aBLAST.html) with the amino acid sequence of *Drosophila* Lgs. DLgs shows statistically significant similarity to the human Bcl9 protein, a previously described protein of unknown function. The main regions of homology are Lgs amino acids 323-554 and Bcl9 amino acids 177-383.

The hlgs/bcl9 full-length cDNA was assembled from partial EST clone sequences (NCBI:AI338959 and NCBI:AL039210) and PCR fragments obtained on human cDNA and genomic DNA preparations. After the assembly process, the sequence was verified by crosschecking with genomic DNA sequences and the publicly available data.

EXAMPLE II

Use of Lgs as a Hybridization Probe

The following method describes use of a non-repetitive nucleotide sequence of lgs as a hybridization probe. The method can be applied to screen for lgs homologues as well. DNA comprising the sequence of lgs (as shown in FIGS. 2A-2G (SEQ ID NO:2), 8A (SEQ ID NO:14) and 10A (SEQ ID NO:16)) is employed as probe to screen for homologue DNAs (such as those included in cDNA or genomic libraries).

Hybridization and washing of the filters containing either library DNAs is performed under standard high stringency conditions (Sambrook, Fritsch et al. 1989). Positive clones can be used to further screen larger cDNA library platings. Representative cDNA-clones are subsequently cloned into pBluescript (pBS, Stratagene) or similar cloning vectors, and sequenced.

EXAMPLE III

Use of Lgs as a Hybridization Probe for In Situ Hybridization

In situ hybridization of *Drosophila* lgs mRNA can be performed in embryo as described in (Tautz and Pfeifle 1989). However, with small modifications it can also be used to detect any mRNA transcript in *Drosophila* larval imaginal discs or vertebrate tissue sections. Labeled RNA probes can be prepared from linearized lgs cDNA (as showed in FIG. 2), or a fragment thereof, using the DIG RNA labeling Kit (SP6/T7) (Boehringer Mannheim) following the manufacturer's recommendations. A similar method can be used with hLgs as a hybridization probe to screen human tissues.

EXAMPLE IV

Expression of Lgs in *Drosophila melanogaster*

Lgs can be expressed in *Drosophila* in the whole organism, in a specific organ or in a specific cell type, during the whole life or only at a specific developmental stage, and at different levels. An overview of the standard methods used in *Drosophila* genetics can be found in (Brand and Perrimon 1993; Perrimon 1998; Perrimon 1998).

Generation of Lgs Mutant Embryos

Mosaic germlines are generated by help of site-specific recombination through the FLP recombinase (Xu and Rubin 1993). Females of the genotype hsp70:flp,tub:>dlgs-cDNA>Gal4/+; dlgs20F/dlgs20F (mutant dlgs alleles) are heat-shocked at 37° C. for 1 hr during the third instar larval stage to induce FLP-directed recombination and later mated to UAS:GFP/UAS:GFP; dlgs20F/yellow+ males. Germline mosaics are induced in homozygote dlgs20F-mutant females carrying one copy of a digs cDNA ("rescuing") transgene flanked by two recombination target sites (symbolized by ">") and followed by a Gal4 coding sequence. The source of recombinase is a first chromosome insertion of a fusion of the hsp70 promoter (denoted by "hsp70") to the FLP coding sequence. Excision of the rescuing digs cDNA from cell clones in larval tissue gives rise to adult female germ lines that produce oocytes that do not contain neither zygotic nor maternally contributed information for the production of functional Lgs protein. At the same time the Gal4 coding sequence is spliced to the transgenic promoter sequence, which induces formation of the heterologous transcriptional activator. Upon fertilization of the zygotically and maternally digs mutant oocytes, the Gal4 transcriptional activator turns on a UAS:GFP transgene contributed by the paternal sperm which mark the mutant eggs by GFP expression. With this method, about fifty percent of the produced eggs express GFP and thus have excised the lgs rescue transgene. For analysis, cuticles are prepared by standard techniques from mutant embryos, and examined by dark field microscopy.

Generation of Digs Mutant Embryos Expressing Constitutively Active Arm

In order to express constitutively active Arm ("ΔArm"), females of the genotype described above are heat shocked at 37° C. for 1 hr during late pupal stages and mated to males of the genotype UAS:GFP,UAS:ΔArm/UAS:GFP,UAS:ΔArm; dlgs$^{20F}$/yellow$^+$. Due to the additional presence of the UAS:ΔArm transgene in these males all offspring that had arisen from a digs mutant oocytes expressed both the marker protein GFP and a constitutively active Arm protein that permanently induced Wg target genes.

EXAMPLE V

Expression of Lgs in *E. coli*

The following method describes recombinant expression of Lgs in bacterial cells. Alternatively, recombinant proteins can be produced and isolated from insect and mammalian cells (Sambrook, Fritsch et al. 1989). DNA encoding full-length or a truncated Lgs form is fused downstream of an epitope tag or glutathione-S-transferase (GST) cDNA and a thrombin cleavage site contained within an inducible bacterial expression vector. Such epitope tags include poly-his, S-protein, thioredoxin, and immunoglobin tags. A variety of plasmids can be employed, including commercially available plasmid such as pGEX-4T (Pharmacia).

Briefly, a bacterial expression plasmid containing the Lgs sequence, for instance fused to a GST-sequence is transformed by conventional methods into protease deficient *E. coli* such as BL21 (e.g., Stratagene). A bacterial colony containing the plasmid is then expanded overnight in selection medium to reach saturation. The next morning, this culture is diluted 1:100 and bacterial are allowed to grow to an optical density (OD$_{600}$) of 0.6. Protein production is initiated by addition of an inducer of the promoter under which GST-Lgs fusion protein is expressed. A variety of inducers can be employed depending on the expression vector used, including IPTG.

Expressed GST tagged Lgs can then be purified, for instance, using affinity beads or affinity chromatography, such as glutathione beads (commercially available, e.g., from Pharmacia). Extracts are prepared by lysing the Lgs-expressing bacteria in sonication buffer (10 mM Tris HCl pH 8.0, 150 mM NaCl, 1 mM EDTA, 1.5% sarkosyl, 2% Triton-X-100, 1 mM DTT and protease inhibitors), followed by short sonication on ice (e.g., 3 times 20 seconds at middle power) and centrifugation. Cleared supernatants are then incubated under gentle rotation for example with glutathione beads for 2 hrs at 4° C. Next beads are washed several time in washing buffer (20 mM Tris pH 8.0, 200 mM NaCl, 1 mM EDTA, 1 mM DTT, 1 mM MgCl$_2$, 0.5% NP40), and finally stored in storage buffer (20 mM Tris pH 8.0, 200 mM NaCl, 1 mM EDTA, 1 mM DTT, 1 mM MgCl2, 10% glycerol, 0.5% NP40, and proteinase inhibitors). Alternatively, a His-tagged or IgG tagged Lgs can be purified using Ni$^{2+}$-chelate affinity chromatography or Protein A or Protein G column chromatography, respectively.

The quality of the preparations can be checked, e.g., by SDS-gel electrophoresis and silver staining or Western blot.

In case the epitope tagged has to be cleaved, several methods are available depending on the presence of a cleavage site between the epitope tagged and the Lgs protein. For example, it is possible to produce a GST-Lgs fusion protein containing a thrombin cleavage site right before the first Lgs amino acid. Briefly, a GST-Lgs preparation on glutathione-affinity beads is washed several times in cleavage buffer (50 mM Tris HCl pH 7.0, 150 mM NaCl, 1 mM EDTA, 1 mM DTT). Thrombin is then added and the samples are incubated for over 16 hrs at room temperature. Supernatants are then collected and analyzed for successful cleavage of Lgs from the beads by polyacrylamide gel electrophoresis and silver staining or Western blot. The purified proteins can be used, e.g., to generate anti-Lgs antibodies as described in (Harlow and Lane 1988)

EXAMPLE VI

Protein-Protein Interactions Involving Lgs

An in vitro co-immunoprecipitation assay can be performed to find or confirm Lgs interaction partners. For instance, HEK293 cells at 50% confluence are transfected by a lipofection method. For this purpose, mammalian expression vectors containing cDNA encoding for tagged Lgs and potential interaction partners are combined with Lipofectamine transfection reagent (Life Technologies, Inc.) following the manufacturer recommendations, and overlaid onto monolayers of cells. Cells are lysed 25 hrs after transfection in co-IP buffer (20 mM Tris HCl pH 7.5, 140 mM NaCl, 1.5 mM MgCl$_{21}$ 1 mM EDTA, 1 mM DTT, 1% Triton-X100, 10% glycerol, 1 mM Natrium vanadate, 50 mM NaF, and protease inhibitors). Immunoprecipitations are performed in co-IP buffer using anti-tag antibodies (e.g., anti-HA, clone 3F10, Boehringer Mannheim) conjugated to protein G-agarose (Boehringer Mannheim). Control immunoprecipitations are performed using rat or mouse IgG (Sigma-Aldrich). After 3 hrs incubation at 4° C., beads are washed 4 times in washing buffer (20 mM Tris HCl pH 7.5, 140 mM NaCl, 1.5 mM MgCl$_2$, 1 mM EDTA, 1 mM DTT, 1 Triton-X100, 1 mM Natrium vanadate, 50 mM NaF) and resuspended in 25 μl of Laemmli buffer. Immune complexes are analyzed by SDS-PAGE/immunoblot assay using anti- Lgs polyclonal antibodies provided by the invention or anti-tag antibodies, followed by horseradish peroxidase conjugated secondary antibody (Amersham Pharmacia Biotech). Detection can be performed using an enhanced chemiluminescence detection method (e.g., ECL, Amersham Pharmacia Biotech).

A GST-fusion protein in vitro binding assay can be performed, e.g., to map binding domains, confirm an interaction partner or find additional interacting proteins. For this purpose, proteins are in vitro translated (IVT) using reticulocyte lysates (TNT-lysates, Promega Corporation) containing [$^{35}$S] methionine following the instructions provided by the manufacturer. Glutathione S-transferase (GST) fusion proteins, produced as illustrated in the Example V, are immobilized on glutathione-Sepharose and blocked in binding buffer (20 mM Tris pH 8.0, 200 mM NaCl, 1 mM EDTA, 1 mM DTT, 1 mM MgCl2, 10% glycerol, 0.5% NP40, 0.05% BSA, and proteinase inhibitors) for 45 min. Two µg of immobilized GST proteins are then incubated for 1.5 hrs with 0.5-4 µl of IVT proteins in binding buffer. The beads are washed four times in washing buffer (20 mM Tris pH 8.0, 200 mM NaCl, 1 mM EDTA, 1 mM DTT, 1 mM MgCl$_2$, 0.5% NP40) and boiled in Laemmli SDS sample buffer. The use of equivalent amounts of intact GST fusion proteins and successful IVT of the AR has to be confirmed by SDS-PAGE analysis using Coomassie staining or autoradiography, respectively.

A yeast two hybrid assay can additionally be performed to confirm the results of the in vitro binding assays described above or to screen a cDNA library for new interaction partners (Fields and Sternglanz 1994). To confirm a specific binding (e.g., β-Cat) or to map the binding region between Lgs and an interaction partner the desired cDNAs are subcloned into appropriate yeast expression vectors that link them either to a Lex DNA binding domain (e.g., pLexA, Clontech) or an acidic activation domain (e.g., pGJ4-5, Clontech). The appropriate pair of plasmids is then transformed together with a reporter plasmid (e.g., pSH18-34, Clontech) into an appropriate yeast strain (e.g., EGY48) by the lithium acetate-polyethylene glycol method and grown on selective media (Sambrook, Fritsch et al. 1989). Transformants are analyzed for reporter gene activity as described by the manufacturer of the vector-reporter plasmid used. To establish reproducibility the interactions is tested in both directions.

To isolate novel Lgs-binding proteins (Bartel, Fields "The Yeast two-Hybrid System" Oxford UP, 1997) an appropriate yeast strain is transformed with a beta-Galactosidase reporter plasmid, a yeast expression vector containing Lgs cDNA, or parts thereof (such as the dLgs/hLgs-homology regions), fused to the LexA DNA-binding domain sequence ("bait vector") and a second yeast expression vector containing a transcriptional activation domain fused to a collection of cDNA sequences ("prey vector" library, e.g., RFLY1 0-12 h embryo library, described in PNAS 93, 3011ff.). The triple transformants containing the reporter plasmid, and the bait and prey vectors are then grown on selective media, and selected for interaction-dependent activation of the auxotrophic and beta-Galactosidase reporters. From selected clones the respective prey construct is reisolated and the specificity of bait/prey-interaction is assessed, by checking for absence of interaction with unrelated bait-constructs. Finally the confirmed interactors are sequenced and full-length cDNAs are assembled and tested again for specific interaction with the bait.

In two unrelated screens using Lgs full-length and Lgs N (amino acids 1-732) as baits, we isolated independent cDNA clones of a novel protein, Daughter of Legless (dDoll). Doll specifically binds to the homology domain 1 of dLgs (amino acids 318-345) and hLgs/BCL9 (amino acids 177-205) through its C-terminal PHD-finger, a Zinc-finger related structural motif (see U.S. provisional application No. 60/277,976).

EXAMPLE VII

Immunohistochemistry

Localization of Lgs protein can be performed on *Drosophila* embryo, imaginal discs, adult tissue sections, vertebrate tumor cell lines, or vertebrate tissues using the anti-Lgs antibodies provided by this invention. For instance, if a transformed cell line like HEK 293 cells (ATCC) is used, cells are seeded into polylysine-coated 8 well chambers (Nalge-Nunc Internat.) and grown overnight at 37° C. The next day, cells are fixed with 3.7%-formaldehyde in PBS for 10 min., permeabilized in 0.5% Triton-X-100 for another 10 min, and blocked with a 1:1000 dilution of pre-immunoserum in 2% BSA-PBS for 1 h at RT. Cells are then incubated with a 1:1000 dilution of anti-Lgs polyclonal rabbit immunoserum provided by this invention for 2 hrs at RT. The slides are washed three times for 5 min in PBS and incubated with a 1:200 dilution (v/v) of TRITC-conjugated swine anti-rabbit immunoglobulin (Dako, Inc.). The washing step is repeated before applying coverslips using Vectashield® mounting medium (Vector Laboratories, Inc.). Detection of other proteins such as Arm/β-Cat or Pan/Tcf can be performed in the same way using specific antibodies. As a positive control part of the cells can be transfected, e.g., by a lipofection method with a Lgs expression plasmid, such as pcDNA3.1 (Invitrogen). Two days after transfection, control cells are stained with anti-Lgs antibodies as described above.

EXAMPLE VIII

Luciferase Reporter Gene Assays

The effect of Lgs on Tcf transactivation activity can be performed in a cell culture system using a Tcf reporter gene. A Tcf-responsive reporter gene is a construct which comprises a readily detectable or assayable gene such as β-galactosidase, green fluorescent protein, chloramphenicol acetyltransferase or luciferase, linked in cis to a Tcf response element and a minimal promoter. Depending on the expression vectors used, this protocol can be applied for mammalian as well as for *Drosophila* cell lines. For instance, HEK293 cells (ATCC) are a well suitable system. Hereby, Lgs and β-Cat full length cDNA are cloned into a mammalian expression vector, such as pcDNA3 (Invitrogen), and transfected together with a Tcf driven luciferase reporter plasmid (TOPFLASH, Upstate biotechnology, New York, USA) into HEK 293 cells. Any means for introducing genetic material into cells can be used, including but not limited to infection, electroporation or transfection. For instance, to introduce DNA into HEK 293 cells, a lipofection agent like the Lipofectamine transfection reagent (Life Technologies, Inc.) can be used. A *renilla* luciferase reporter plasmid, e.g., pRL-SV40, (Promega Corporation, Madison USA), is co-transfected to normalize for transfection efficiency. Cell extracts are prepared 48 h after transfection and assayed for firefly and *renilla* luciferase activity as described by the manufacturer (Dual luciferase reporter assay system, Promega Corporation). All the luciferase values are normalized for *renilla* luciferase activity.

EXAMPLE IX

RNA Interference Experiments

RNA interference (RNAi) is a form of post-transcriptional gene silencing mediated by short double stranded RNAs (dsRNA) that has been described in plants, nematode, invertebrates organisms and mammalian cell culture ((Ngo, Tschudi et al. 1998) (Vaucheret and Fagard 2001) [Caplen, 2000 #170; Kennerdell, 1998 #171; Timmons, 1998 #172]). However, in plants a transcriptional gene silencing mechanism based on DNA methylation has also been suggested (Wassenegger 2000). DsRNAs have been shown to induce a degradation response in which single stranded RNA complementary to the short dsRNA is rapidly degraded (Montgomery, Xu et al. 1998). RNAi can thus be used to reduce gene expression for instance in whole organisms or invertebrate and vertebrate cell lines (Kennerdell and Carthew 1998), (Elbashir, Harborth et al. 2001), (Caplen, Fleenor et al. 2000). Several methods to introduce dsRNA into cells can be found in the literature. By hand of an example, we describe herein the treatment of Drosophila cells with dLgs dsRNA.

Lgs dsRNA Preparation

Lgs dsRNA can be made from cDNA or genomic DNA templates, as long as most of the dsRNA corresponds to exon regions. Normally, target regions of 700 to 800 base pair are the most active. However, is known that dsRNAs as short as 200 base pair and as long as 2000 base pairs have potent interfering activities. Both RNA strands can be synthesized simultaneously from a PCR fragment, which contains for instance a T7, SP6 or a T3 promoter on each end. This PCR fragment can be generated by amplification of Lgs cDNA or genomic DNA with 2 primers containing, e.g., T7-polymerase binding sites. Primers complementary sequences should be 20 to 24 nucleotides in length with a 22 nucleotides optimum and 60° C. optimum Tm. The 5' end of each primer should correspond to, e.g., a 27 nucleotides T7 promoter sequence (TAATACGACTCACTATAGG-GAGACCAC (SEQ ID NO:22)). The PCR reaction is then performed with a suitable template containing Lgs sequences. Taq polymerase gives the best yields, but another polymerase like Pfu may be used, too. The first 10 cycles should have a 40° C. annealing step, followed by 35 cycles with a 55° C. annealing step. DMSO can be added to a final concentration of 5%-when needed. Phenol-chloroform extract and ethanol precipitation in NH$_4$OAc may be used to isolate the PCR template from the reaction mix however other commercially available PCR-purification kit can be used as well. The RNA synthesis reaction can be performed in 50 μl volume with 1 μg of PCR DNA template using an appropriate RNA polymerase. The MEGAscript™ kits from Ambion work very well. The RNA becomes double-stranded during the synthesis reaction. The DNA template can be removed with RNase-free DNAase and the dsRNA can be purified by phenol-chloroform extraction and ethanol precipitation. Typical yields of RNA from 1 μg DNA template are in the 80 to 120 μg range. dsRNA is stored as a NaOAc/ethanol precipitate at −80° C. until immediately before use.

The quality of the dsRNA can be monitored by native agarose gel electrophoresis in TBE. Only preparations should be used in which the electrophoretic mobility of most of the RNA is shifted to the mobility expected for dsRNA (very close to duplex DNA mobility) of the appropriate length.

Transfection of Lgs dsRNA into Drosophila S2 Cells

S2 cells are propagated in Schneider S2 Drosophila medium (GIBCO) supplemented with 10% FCS. One day before transfection one million cells are seeded into 6 well plates and grown overnight at 25° C. Cells are then transfected using the cationic lipid CellFectine (GIBCO) using an adaptation of the manufacturer's protocol. Briefly, a total of 5 μg DNA and dsRNA is complexed with 20 1 of CellFectine lipid mix in 1.2 ml serum free growth medium (e.g., DES expression medium from Invitrogen, Carlsbad, USA). The complexes are incubate for 15 minutes at RT and then added to the cells from which the normal growth medium has been replaced with 1 ml serum free medium. Four hours later 1.2 ml growth medium supplemented with 30% FCS is added to the cells. One day after transfection the medium is replaced with fresh medium containing 10% FCS. Cells can be assayed from 2 days after transfection (e.g., for Lgs protein level or for Tcf transcriptional activity).

Similarly, mammalian Lgs expression can be reduced using the method described in (Elbashir, Harborth et al. 2001).

EXAMPLE X

Search for Lgs Homologues

Bcl9, a human protein involved in B-cell lymphoma was identified by searching a public sequence database (www.ch.embnet.org/software/aBLAST.html) with fragments of about 500 amino acids of the Drosophila Lgs protein. The matrix used was Pam70 and the parameters were set so that repetitive sequences were filtered out. Although the overall homology of Bcl9 and dLgs is very low, they share several short stretches of amino acids with high homology and in the same sequential order (see FIGS. 7A-7B (SEQ ID NOs:2-13)). Local alignments were generated using A WWW server implementation of LALIGN (version 2.0u6319919. The parameters used are: matrix: pam120; gap penalties: −14/−4; alignment 4-edited by hand.

The hlgs-1 gene was found by searching the public high throughput sequence database for predicted coding sequences (cDNA) with homology to the translated sequence of Bcl9 protein fragments (FIGS. 10A (SEQ ID NO:16)-10B (SEQ ID NO:17)). The program used was tblastn, whereas the parameters and matrixes were the same as described above for Lgs. The gene is situated on chromosome 11 and several EST are present in the public human genome databases. Translation of the predicted cDNA and EST and a first assembly attempt results in a predicted protein containing all the homology domains of FIGS. 7A-7B (SEQ ID NOS:2-13). For instance hLgs-1 has a 54% and 57% amino acids identity with dLgs and hLgs, respectively, in domain 1, and a 23% and 60% amino acid identity, respectively, in domain 2 (data not shown).

EXAMPLE XI

Rescue of dLgs−/− Flies with hLgs/Bcl9 cDNA Expression

In order to confirm the functional homology between Drosophila and human Lgs, the human gene was introduced into Drosophila mutant embryos lacking endogeneous dLgs. Specifically, a tub:hLgs/BCL9 transgene was introduced into mutant lgs20F/lgs20F and lgs17E/lgs21L flies (described above). These Lgs mutant flies display larval or pupal lethality. In contrast, flies carrying the tub:hLgs/BCL9 transgene survive to adulthood and are capable of exclosing from the pupa. This demonstrates that despite the low sequence homology hLgs can replace dLgs function in the flies and is thus a true functional homologue.

EXAMPLE XII

Screening for Small Molecules Inhibiting Lgs-β-Cat or Lgs-Doll

Several assays are available to test for inhibitors of protein-protein interactions. They can be cell-based or in vitro-based. Cell-based assays are for instance reporter gene assays and yeast or mammalian two hybrid assays. Cell-free assays can be subdivided into heterogeneous and homogeneous assays. In general homogeneous assays are preferred because they avoid washing steps and therefore results in higher throughput compared to heterogeneous assays (e.g., ELISA). Novel homogeneous assay technologies are, for example, the scintillation proximity assay (SPA) (Cook 1996), and fluorescence-based assays such as homogeneous, time resolved fluorescence (HTRF) (Kolb, Burke et al. 1997) and fluorescence polarisation (FP) (Sittampalam, Kahl et al. 1997). By means of an example we describe herein the conditions to screen a chemical library at high throughput for inhibitors of the hLgs-β-Cat interaction using the HTRF technique.

A homogeneous time-resolved fluorescence (HTRF) assay was developed to monitor hLgs/β-Cat binding. This assay employs a histidin-tagged (His-tag) hLgs(300-434) fragment, a GST-fused β-Cat(Armadillo repeat 1-13), and two fluorophore-conjugated detection reagents, XL665-labeled anti-His- and europium cryptate-labeled anti-GST antibodies. The recombinant proteins needed for the assay are produced in BL21 bacteria (e.g., Novagen) and purified over a Nickel column (His-tagged hBcl9) or glutathione beads (GST-β-Cat(Arm-repeats 1-13)). As a negative control a His-tagged hLgs fragment lacking the β-Cat binding domain (hLgs(300-434)Δcoil) was generated. The other reagents and the technical devices needed are commercially available (e.g., by Wallac or Packard instruments). Energy transfer from europium cryptate to the acceptor chromophore XL665 can only occur if the distance between the two molecules is short. Binding of hLgs to β-Cat in binding buffer (20 mM Tris-HCl pH 8.0, 200 mM NaCl, 1 mM DTT, 1 mM $MgCl_2$, 10% glycerol, 0.5% NP40, 0.05% BSA) brings the fluorophores into close proximity, allowing fluorescence resonance energy transfer to occur. In the presence of a molecule which inhibits hLgs-β-Cat interaction the distance between donor and acceptor fluorophore is increased resulting in a reduced fluorescence signal. This assay can be up-scaled to work in 384 well plates allowing the screening of several thousand potential inhibitory compounds a day.

EXAMPLE XIII

Use of Lgs Homology Domain Two Peptides to Inhibit Wnt Signaling In Vivo

To demonstrate the essential role of the sequence homology domains (HD) of Lgs described in FIGS. 7A-7B (SEQ ID NOs:2-13) for the propagation of the Wnt signaling pathway, a Tcf-reporter gene assay was performed. In this, HEK293 cells at 50% confluence were plated into 24-well plates and transfected by a lipofection method. 240 ng of TOPFLASH luciferase reporter plasmid (Upstate biotechnology, New York, USA), 4 ng of pcDNA3-ΔArm, 200 ng of pcDNA3-EGFP-hLgs-peptide and 10 ng of a *renilla* luciferase reporter plasmid pRL-SV40 (Promega Corporation, Madison USA) were diluted into 25 μl of OPTI-MEM Medium (Life Technologies, Inc.) and combined with 1.2 μl of Lipofectamine (Life Technologies, Inc.) in 25 μl OPTI-MEM. After incubation for 20 min, 0.175 ml of OPTI-MEM was added and the mixtures were overlaid onto monolayers of cells. After culturing at 37° C./5% $CO_2$ for 6 hr, 0.225 ml of OPTI-MEM containing 20% FCS was added to the cultures. Cell extracts were prepared 48 h after transfection and assayed for firefly and *renilla* luciferase activity as described by the manufacturer (Dual luciferase reporter assay system, Promega Corporation). Small peptides including the HD2 (such as hLgs/Bcl9(199-392) or hLgs/Bcl9 (279-392)) strongly inhibit Arm-Tcf transcriptional activity.

Figure 15B:
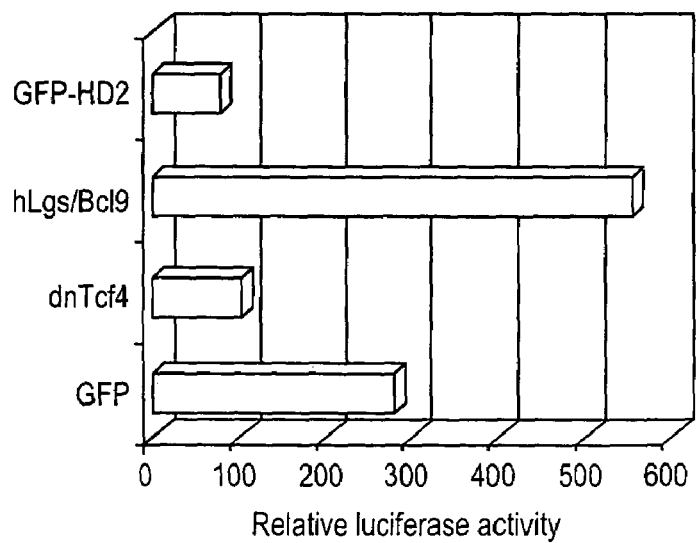

Importantly, Lgs HD 2 peptides also inhibit Tcf-driven luciferase activity in SW480 colon carcinoma cells (American Tissue Culture Collection), which have a constitutively active β-Cat due to a mutation in the APC gene [Smith, 1993 #186] (FIG. 15B). As a positive control, a dominant negative hTcf4 (dnTcf4) protein was used [Roose, 1999 #187]. Cells were transfected as described above but using Lipofectamine 2000 (GIBCO Life Technologies) instead of Lipofectamine following the manufacturer recommendations.

These results indicate that Lgs peptides can be used for the therapy of diseases characterized by an over-activation of downstream components of the Wnt pathway.

The invention claimed is:

1. An isolated polypeptide consisting of:
   (i) a *Drosophila* Legless (dLgs) protein consisting of amino acids 1 to 1464 of SEQ ID NO:23, or
   (ii) a peptide fragment of (i), wherein said fragment has the amino acid sequence of SEQ ID NO:2 or SEQ ID NO:4 and inhibits tcf-driven luciferase activity in colon cancer cells, or
   (iii) a peptide fragment of (i) having at least 90% amino acid sequence identity to the amino acid sequence of SEQ ID NO:4 and inhibits tcf-driven luciferase activity in colon cancer cells, or
   (iv) a peptide having at least 90% amino acid sequence identity to the amino acid sequence of SEQ ID NO:5 and inhibits tcf-driven luciferase activity in colon cancer cells, or
   (v) a peptide fragment of (i) having at least 90% amino acid sequence identity to the amino acid sequence of SEQ ID NO:2 and inhibits tcf-driven luciferase activity in colon cancer cells, or
   (vi) a peptide fragment of (i) having at least 90% amino acid sequence identity to the amino acid sequence of SEQ ID NO:3 and inhibits tcf-driven luciferase activity in colon cancer cells.

2. A chimeric molecule comprising the polypeptide of claim 1 fused to a heterologous polypeptide.

3. The chimeric molecule according to claim 2, wherein said heterologous polypeptide is selected from the group consisting of an antigenic epitope, glutathione-S-transferase, thioredoxin, and antibody.

4. A pharmaceutical composition comprising the polypeptide of claim 1, and a pharmaceutically acceptable carrier.

5. An isolated polypeptide comprising a *Drosophila* Legless (dLgs) protein comprising amino acids 1 to 1464 of SEQ ID NO:23.

6. The isolated protein as claimed in claim 5, wherein said protein is encoded by a nucleotide molecule having the nucleotide sequence of SEQ ID NO:1.

7. A chimeric molecule comprising the polypeptide of claim 5 fused to a heterologous polypeptide.

8. The chimeric molecule according to claim 7, wherein said heterologous polypeptide is selected from the group consisting of an antigenic epitope, glutathione-S-transferase, thioredoxin, and antibody.

9. A pharmaceutical composition comprising the polypeptide of claim 5, and a pharmaceutically acceptable carrier.

* * * * *

SEQUENCE LISTING

```
<160> NUMBER OF SEQ ID NOS: 22

<210> SEQ ID NO 1
<211> LENGTH: 6909
<212> TYPE: DNA
<213> ORGANISM: Drosophila lgs
<220> FEATURE:
<221> NAME/KEY: exon
<222> LOCATION: (691)..(981)
<223> OTHER INFORMATION:
<220> FEATURE:
<221> NAME/KEY: exon
<222> LOCATION: (468)..(632)
<223> OTHER INFORMATION:
<220> FEATURE:
```

-continued

```
<221> NAME/KEY: exon
<222> LOCATION: (1456)..(1665)
<223> OTHER INFORMATION:
<220> FEATURE:
<221> NAME/KEY: exon
<222> LOCATION: (2394)..(4397)
<223> OTHER INFORMATION:
<220> FEATURE:
<221> NAME/KEY: exon
<222> LOCATION: (4679)..(4870)
<223> OTHER INFORMATION:
<220> FEATURE:
<221> NAME/KEY: exon
<222> LOCATION: (4927)..(6456)
<223> OTHER INFORMATION:

<400> SEQUENCE: 1
```

| | |
|---|---:|
| acgagtgctt ctcttattat gcgagctgtt tattccaaag tatgttcgca attttcgact | 60 |
| cctgctaaca taacgcacgg ttaaagcagg aacatttggg cctataagcc caaaatttca | 120 |
| ttagcttaat acgatgctcc gaagtgttat tgcatttgca catatacata aaattgtgac | 180 |
| atagaatagg agaattccac atacaaatac aaaaatacaa atcctccag taaaatttaa | 240 |
| aacgatatcg tgttttgctt cgcgtatctc acgtgagatg taatcgcatg catatgagtg | 300 |
| gtgagtgcct gcgtgcagtt cctggtctaa atatgcttaa ttgcgttcgc cgacttcaaa | 360 |
| agcaataaaa cgatggattt taattgctac ttgagcaatt agccacacaa gggatcttgg | 420 |
| gaaggtcgat ttgaaggaat tcgatttcta ggatgctctc gacaaca atg ccc cgc | 476 |

```
                                                    Met Pro Arg
                                                      1
agt cca acc caa caa cag ccg caa cca aac tcc gat gcc tcc tca aca       524
Ser Pro Thr Gln Gln Gln Pro Gln Pro Asn Ser Asp Ala Ser Ser Thr
  5                  10                  15 agt gca tct gga tca aat cct gga gca gcg atc gga aat ggg gac tcg       572
Ser Ala Ser Gly Ser Asn Pro Gly Ala Ala Ile Gly Asn Gly Asp Ser
 20                  25                  30                  35 gcg gcg agc aga agt tct ccg aag acc ctt aat agc gaa ccc ttt tct       620
Ala Ala Ser Arg Ser Ser Pro Lys Thr Leu Asn Ser Glu Pro Phe Ser
                 40                  45                  50 act ttg tcg ccg ggtaagactt gtattgattt ctctttgtcc ggaattataa           672
Thr Leu Ser Pro
             55 caactttctg tgtttcca gat caa ata aaa ttg acg cca gaa gaa ggc act       723
                    Asp Gln Ile Lys Leu Thr Pro Glu Glu Gly Thr
                                    60                  65 gag aaa agc gga cta tca act agt gat aaa gct gcc act gga gga gcc       771
Glu Lys Ser Gly Leu Ser Thr Ser Asp Lys Ala Ala Thr Gly Gly Ala
             70                  75                  80 cca ggc agt gga aat aat ctg ccc gag gga caa act atg cta agg cag       819
Pro Gly Ser Gly Asn Asn Leu Pro Glu Gly Gln Thr Met Leu Arg Gln
         85                  90                  95 aac tct acg agc aca atc aac tcg tgc cta gtc gct tct cca caa aac       867
Asn Ser Thr Ser Thr Ile Asn Ser Cys Leu Val Ala Ser Pro Gln Asn
    100                 105                 110 tcc agt gaa cac tcg aat agc agc aat gtg tct gct aca gtg ggc ctt      915
Ser Ser Glu His Ser Asn Ser Ser Asn Val Ser Ala Thr Val Gly Leu
115                 120                 125                 130 act cag atg gta gat tgt gac gag caa tcg aag aaa aac aaa tgt agt      963
Thr Gln Met Val Asp Cys Asp Glu Gln Ser Lys Lys Asn Lys Cys Ser
                135                 140                 145 gtg aag gac gag gaa gct ggtaagactg ccctacaaat ggtttaaaat             1011
Val Lys Asp Glu Glu Ala
                150
```

-continued

```
tttaaaatgt attggcgttc acctttgtta atcatttaat tgtttttttt ttgctatact    1071
tacaatttta gttttaaact tgtaaacttg actaaaactc gcgaagctcg gatcaaaaca    1131
gacattttct tggaaccgta attaagctca taaaaatatt aattcatctt gatggaatgc    1191
atatcataga tgtactcaaa catctcaaga aagacctcaa attggatcaa ctaattagtt    1251
tgagaaaaaa ttgctgtact tttaagaata tattaattta aaaatttgct gagtgaaatg    1311
atataatagt cacaataatt tttagttaaa ctgctaaagc attttgaata gccgtgctac    1371
gcagatgcta ctagacgcgg tgtaaaagct aattttttatt taaagctgt cctaatattc    1431 cataaccatt aatgtcccat ttca gaa ata agt tct aat aaa gca aaa ggt        1482
                           Glu Ile Ser Ser Asn Lys Ala Lys Gly
                                   155                 160 caa gca gct ggt ggc ggc tgc gaa aca ggt tct aca tcc agt ttg act        1530
Gln Ala Ala Gly Gly Gly Cys Glu Thr Gly Ser Thr Ser Ser Leu Thr
       165                 170                 175 gtc aag gaa gaa ccc acc gat gtc tta ggc agt tta gta aat atg aaa        1578
Val Lys Glu Glu Pro Thr Asp Val Leu Gly Ser Leu Val Asn Met Lys
   180                 185                 190 aaa gaa gaa aga gaa aat cat tcg cca acg atg tcc cct gtt ggt ttt        1626
Lys Glu Glu Arg Glu Asn His Ser Pro Thr Met Ser Pro Val Gly Phe
195                 200                 205 ggt tca att ggt aat gca cag gac aac tcc gct aca ccg ggtaagtttt        1675
Gly Ser Ile Gly Asn Ala Gln Asp Asn Ser Ala Thr Pro
210                 215                 220 aagagatcca tataaagcaa ataacaagaa ttaatgtcag ttaccaattt tatttgatag    1735
tcaaagaact actatagcga tatctcctgc cttttaattt tattttaatt aggaaatacg    1795
aatatttcta atttgtaaaa taaaattgat taattaacta gaatttaaaa accttttgaa    1855
ttaggacata cccttccaaa aatcagtaat cattgggaac gagagtgtgg tcccgaagga    1915
gactactata aaacctttg agctatctga tactgcacgc tactaaaaat gattagttta    1975
ggaaaatggg tgtaattttg taggaagttt tcattttaga agaaatgtga ttattttatt    2035 aaacccctc aagcggaact acatttgttc tacgatattt tggaaaaaca aatggttaag    2095
ttggaaagtg cctataaaac agaattccac ggtttcaaat actaaccagg tttttgattt    2155
aattttgatt aaatgagaaa ttatcacact tcagttaaaa tgtttaattc gattaaggtc    2215
ggacaatcac agcagatttc cattttttgcg tgtatatata aagtcgcct tcacactctt    2275 ctggcgcgct tcaccactac gtggagttcc gcccgcagtg attttatatag atgatttacg    2335 agttatttaa tttttttatgg tgtattttaa taaatatctt atttattcat tttacata    2393 gtt aaa att gaa aga att tca aac gac agt acc acg gaa aaa aaa gga       2441
Val Lys Ile Glu Arg Ile Ser Asn Asp Ser Thr Thr Glu Lys Lys Gly
       225                 230                 235 tcg tcc ttg aca atg aat aat gac gaa atg agc atg gaa ggc tgc aat       2489
Ser Ser Leu Thr Met Asn Asn Asp Glu Met Ser Met Glu Gly Cys Asn
   240                 245                 250 cag ttg aat ccc gat ttt atc aat gaa tct tta aat aat cct gca att       2537
Gln Leu Asn Pro Asp Phe Ile Asn Glu Ser Leu Asn Asn Pro Ala Ile
255                 260                 265                 270 tcg agc ata tta gta agc gga gta gga cca ata ccc gga atc gga gtt       2585
Ser Ser Ile Leu Val Ser Gly Val Gly Pro Ile Pro Gly Ile Gly Val
           275                 280                 285 gga gcg ggg acg gga aat tta ttg act gcc aac gcc aat gga atc tcc       2633
Gly Ala Gly Thr Gly Asn Leu Leu Thr Ala Asn Ala Asn Gly Ile Ser
       290                 295                 300
```

-continued

| | |
|---|---|
| tcg ggt agc agt aat tgt ttg gat tac atg caa cag caa aat cac ata<br>Ser Gly Ser Ser Asn Cys Leu Asp Tyr Met Gln Gln Gln Asn His Ile<br>305                        310                        315 | 2681 |
| ttc gtg ttt tca act cag ctg gcc aac aaa ggg gcc gaa tca gtt tta<br>Phe Val Phe Ser Thr Gln Leu Ala Asn Lys Gly Ala Glu Ser Val Leu<br>320                        325                        330 | 2729 |
| agc ggt caa ttt caa act att att gcg tat cac tgc act cag cct gct<br>Ser Gly Gln Phe Gln Thr Ile Ile Ala Tyr His Cys Thr Gln Pro Ala<br>335                        340                        345                        350 | 2777 |
| aca aaa agc ttc ctg gaa gac ttt ttt atg aaa aac cct tta aag att<br>Thr Lys Ser Phe Leu Glu Asp Phe Phe Met Lys Asn Pro Leu Lys Ile<br>                        355                        360                        365 | 2825 |
| aac aag tta cag cgg cac aat tcc gtc ggt atg cca tgg ata ggc atg<br>Asn Lys Leu Gln Arg His Asn Ser Val Gly Met Pro Trp Ile Gly Met<br>          370                        375                        380 | 2873 |
| ggg cag gtt gga cta act cct cct aat cct gta gcc aaa ata aca caa<br>Gly Gln Val Gly Leu Thr Pro Pro Asn Pro Val Ala Lys Ile Thr Gln<br>385                        390                        395 | 2921 |
| cag cag cca cat aca aag acc gta ggc cta ttg aaa ccc caa ttc aat<br>Gln Gln Pro His Thr Lys Thr Val Gly Leu Leu Lys Pro Gln Phe Asn<br>400                        405                        410 | 2969 |
| caa cat gaa aac agc aaa cgt agt act gta agc gcg cct agc aac tct<br>Gln His Glu Asn Ser Lys Arg Ser Thr Val Ser Ala Pro Ser Asn Ser<br>415                        420                        425                        430 | 3017 |
| ttt gtc gac cag tct gat cct atg ggc aac gaa act gaa ttg atg tgc<br>Phe Val Asp Gln Ser Asp Pro Met Gly Asn Glu Thr Glu Leu Met Cys<br>                        435                        440                        445 | 3065 |
| tgg gaa ggc gga tcc tca aac acc agt agg tct gga caa aac tca cga<br>Trp Glu Gly Gly Ser Ser Asn Thr Ser Arg Ser Gly Gln Asn Ser Arg<br>          450                        455                        460 | 3113 |
| aat cat gta gac agt atc agt aca tcc agc gag tca cag gca ata aag<br>Asn His Val Asp Ser Ile Ser Thr Ser Ser Glu Ser Gln Ala Ile Lys<br>465                        470                        475 | 3161 |
| ata ctg gaa gca gct ggc gtt gat ttg gga cag gtc aca aaa gga agc<br>Ile Leu Glu Ala Ala Gly Val Asp Leu Gly Gln Val Thr Lys Gly Ser<br>          480                        485                        490 | 3209 |
| gat cct ggc ctg aca act gaa aac aac att gta tca ctg caa gga gtt<br>Asp Pro Gly Leu Thr Thr Glu Asn Asn Ile Val Ser Leu Gln Gly Val<br>495                        500                        505                        510 | 3257 |
| aag gtt cca gac gaa aac ctt aca cca caa cag cgg caa cat cgg gaa<br>Lys Val Pro Asp Glu Asn Leu Thr Pro Gln Gln Arg Gln His Arg Glu<br>                        515                        520                        525 | 3305 |
| gaa cag ttg gca aaa ata aaa aaa atg aat caa ttt ctt ttt cct gaa<br>Glu Gln Leu Ala Lys Ile Lys Lys Met Asn Gln Phe Leu Phe Pro Glu<br>          530                        535                        540 | 3353 |
| aat gag aat tca gta gga gct aat gta agc tca cag ata aca aaa att<br>Asn Glu Asn Ser Val Gly Ala Asn Val Ser Ser Gln Ile Thr Lys Ile<br>545                        550                        555 | 3401 |
| cca gga gat tta atg atg ggg atg tcg ggt ggc gga ggc gga tct att<br>Pro Gly Asp Leu Met Met Gly Met Ser Gly Gly Gly Gly Gly Ser Ile<br>          560                        565                        570 | 3449 |
| ata aat ccg acg atg cga caa ctg cat atg cca ggt aac gcc aaa tcg<br>Ile Asn Pro Thr Met Arg Gln Leu His Met Pro Gly Asn Ala Lys Ser<br>575                        580                        585                        590 | 3497 |
| gag ctc tta tcg gcg aca agt tca gga ctt tcg gaa gat gta atg cat<br>Glu Leu Leu Ser Ala Thr Ser Ser Gly Leu Ser Glu Asp Val Met His<br>                        595                        600                        605 | 3545 |
| cca ggg gat gtt ata tca gat atg ggt gcc gta ata gga tgt aat aat<br>Pro Gly Asp Val Ile Ser Asp Met Gly Ala Val Ile Gly Cys Asn Asn<br>          610                        615                        620 | 3593 |

```
aat caa aaa acc agt gtg caa tgt gga tct gga gta ggt gtt gtc act     3641
Asn Gln Lys Thr Ser Val Gln Cys Gly Ser Gly Val Gly Val Val Thr
            625                 630                 635 gga aca act gca gct gga gta aat gtc aat atg cat tgc tca agc tcc     3689
Gly Thr Thr Ala Ala Gly Val Asn Val Asn Met His Cys Ser Ser Ser
    640                 645                 650 ggc gcc ccg aat ggc aat atg atg gga agc tct acg gat atg cta gcc     3737
Gly Ala Pro Asn Gly Asn Met Met Gly Ser Ser Thr Asp Met Leu Ala
655                 660                 665                 670 tcg ttt ggc aac aca agc tgc aac gtc atc gga acg gcc cca gat atg     3785
Ser Phe Gly Asn Thr Ser Cys Asn Val Ile Gly Thr Ala Pro Asp Met
        675                 680                 685 tct aag gaa gtt tta aat caa gat agc cga acc cat tca cat caa ggg     3833
Ser Lys Glu Val Leu Asn Gln Asp Ser Arg Thr His Ser His Gln Gly
            690                 695                 700 gga gtt gct caa atg gag tgg tcg aag att caa cat caa ttt ttc gaa     3881
Gly Val Ala Gln Met Glu Trp Ser Lys Ile Gln His Gln Phe Phe Glu
    705                 710                 715 gaa cgc ctc aag ggg ggc aag ccc aga caa gtc act gga act gta gta     3929
Glu Arg Leu Lys Gly Gly Lys Pro Arg Gln Val Thr Gly Thr Val Val
720                 725                 730 cca caa cag caa acc cct tct gga tct ggt gga aac tcg tta aac aac     3977
Pro Gln Gln Gln Thr Pro Ser Gly Ser Gly Gly Asn Ser Leu Asn Asn
735                 740                 745                 750 cag gtg cga ccc ctg caa ggt cca cct cct cct tac cac tcc atc cag     4025
Gln Val Arg Pro Leu Gln Gly Pro Pro Pro Pro Tyr His Ser Ile Gln
            755                 760                 765 aga tct gcg tca gta cca ata gcc act caa tcg ccc aat ccc tcg agt     4073
Arg Ser Ala Ser Val Pro Ile Ala Thr Gln Ser Pro Asn Pro Ser Ser
    770                 775                 780 cca aac aat cta tct ctc ccg tca ccg cgg aca acc gca gca gtc atg     4121
Pro Asn Asn Leu Ser Leu Pro Ser Pro Arg Thr Thr Ala Ala Val Met
785                 790                 795 gga ttg ccg acc aac tct cct agc atg gat gga aca gga tca tta tct     4169
Gly Leu Pro Thr Asn Ser Pro Ser Met Asp Gly Thr Gly Ser Leu Ser
        800                 805                 810 gga tct gtt ccg caa gct aat act tcg acg gtt cag gca ggc aca aca     4217
Gly Ser Val Pro Gln Ala Asn Thr Ser Thr Val Gln Ala Gly Thr Thr
815                 820                 825                 830 aca gtg ctc tca gca aac aag aac tgt ttt cag gca gac acc cca tcg     4265
Thr Val Leu Ser Ala Asn Lys Asn Cys Phe Gln Ala Asp Thr Pro Ser
            835                 840                 845 ccg tca aat caa aat cgt agt aga aat acc gga tcg tca agc gtt ctt     4313
Pro Ser Asn Gln Asn Arg Ser Arg Asn Thr Gly Ser Ser Ser Val Leu
    850                 855                 860 acg cat aac tta agc agc aac cca agt acc ccc tta tct cat cta tcc     4361
Thr His Asn Leu Ser Ser Asn Pro Ser Thr Pro Leu Ser His Leu Ser
865                 870                 875 cca aag gaa ttt gag tct ttc ggt cag tcc tct gct ggtatgttat          4407
Pro Lys Glu Phe Glu Ser Phe Gly Gln Ser Ser Ala
        880                 885                 890 atttgtttaa ttttttttaaa gacaaatcaa atatgaattg cgttaataat aagttatata   4467
ttacataact cggaaatttg atagaaaaaa tcaggaatag aaaaaataaa ttattttccg   4527
gaccgcccat ccatttcttg aatccaattt ctggagtgat tgttagagat aatctactat   4587
taaaattaaa cacgaaaatt catatccgtt aattgaaaat cactattgtt taataagaaa   4647
ttaaaaatat gtttattata atatttctac a ggt gat aac atg aaa agt agg      4699
                                  Gly Asp Asn Met Lys Ser Arg
```

```
                                895
cga cca agc cca cag ggt cag cgg tca cca gta aat agt cta ata gag    4747
Arg Pro Ser Pro Gln Gly Gln Arg Ser Pro Val Asn Ser Leu Ile Glu
        900                 905                 910 gca aat aaa gat gta cga ttt gct gca tcc agt cct ggt ttt aac ccg    4795
Ala Asn Lys Asp Val Arg Phe Ala Ala Ser Ser Pro Gly Phe Asn Pro
915                 920                 925 cat cca cat atg caa agc aat tca aat tca gca tta aac gcc tat aaa    4843
His Pro His Met Gln Ser Asn Ser Asn Ser Ala Leu Asn Ala Tyr Lys
930                 935                 940                 945 atg ggc tct acc aat ata cag atg gag gtaaatattt aaatatttta          4890
Met Gly Ser Thr Asn Ile Gln Met Glu
            950 tttaacgttt ttgtgttaat ttatcttcct tttcag cgt caa gca tca gcg caa    4944
                                       Arg Gln Ala Ser Ala Gln
                                           955             960 ggt gga tcc gta caa ttt agt cgg cgc tcc gat aat att ccg cta aat    4992
Gly Gly Ser Val Gln Phe Ser Arg Arg Ser Asp Asn Ile Pro Leu Asn
            965                 970                 975 ccc aat agt ggc aat cgg ccg cca cca aac aag atg acc caa aac ttc    5040
Pro Asn Ser Gly Asn Arg Pro Pro Pro Asn Lys Met Thr Gln Asn Phe
            980                 985                 990 gat cca atc tct tct ttg gca caa  atg tcc caa caa cta  aca agt tgc  5088
Asp Pro Ile Ser Ser Leu Ala Gln  Met Ser Gln Gln Leu  Thr Ser Cys
            995                 1000                 1005 gtg tcc  agc atg ggt agt cca  gcc gga act ggt ggt  atg acg atg     5133
Val Ser  Ser Met Gly Ser Pro  Ala Gly Thr Gly Gly  Met Thr Met
1010             1015                  1020 atg ggg  ggt ccg gga ccg tcc  gac atc aat att gag  cat gga ata     5178
Met Gly  Gly Pro Gly Pro Ser  Asp Ile Asn Ile Glu  His Gly Ile
1025             1030                  1035 att tcg  gga cta gat gga tca  gga ata gat acc ata  aat caa aat     5223
Ile Ser  Gly Leu Asp Gly Ser  Gly Ile Asp Thr Ile  Asn Gln Asn
1040             1045                  1050 aac tgt  cat tca atg aat gtc  gta atg aac tca atg  ggt ccc cga     5268
Asn Cys  His Ser Met Asn Val  Val Met Asn Ser Met  Gly Pro Arg
1055             1060                  1065 atg ctg  aat cct aaa atg tgc  gta gca ggc ggt cca  aat gga ccg     5313
Met Leu  Asn Pro Lys Met Cys  Val Ala Gly Gly Pro  Asn Gly Pro
1070             1075                  1080 cct ggc  ttt aat cct aat tcc  ccc aat ggt gga tta  aga gag aat     5358
Pro Gly  Phe Asn Pro Asn Ser  Pro Asn Gly Gly Leu  Arg Glu Asn
1085             1090                  1095 tcc ata  ggg tct ggc tgt ggc  tca gca aac tct tca  aac ttt caa     5403
Ser Ile  Gly Ser Gly Cys Gly  Ser Ala Asn Ser Ser  Asn Phe Gln
1100             1105                  1110 ggg gtt  gtt cca cct ggt gcc  aga atg atg ggt cga  atg cca gtc     5448
Gly Val  Val Pro Pro Gly Ala  Arg Met Met Gly Arg  Met Pro Val
1115             1120                  1125 aat ttt  ggt tcg aat ttc aat  ccg aat att cag gta  aag gcg agt     5493
Asn Phe  Gly Ser Asn Phe Asn  Pro Asn Ile Gln Val  Lys Ala Ser
1130             1135                  1140 acc cca  aac acc ata caa tac  atg cca gta agg gca  cag aac gcc     5538
Thr Pro  Asn Thr Ile Gln Tyr  Met Pro Val Arg Ala  Gln Asn Ala
1145             1150                  1155 aac aac  aat aac aac aat gga  gct aat aat gtg cga  atg cca cct     5583
Asn Asn  Asn Asn Asn Asn Gly  Ala Asn Asn Val Arg  Met Pro Pro
1160             1165                  1170 agt ctg  gaa ttt ttg cag agg  tac gct aac cct caa  atg ggt gct     5628
```

```
        Ser Leu Glu Phe Leu Gln Arg Tyr Ala Asn Pro Gln Met Gly Ala
            1175                1180                1185 gta ggc aat ggg tcg cca ata tgc cca cca tca gcc agc gac ggt            5673
Val Gly Asn Gly Ser Pro Ile Cys Pro Pro Ser Ala Ser Asp Gly
    1190                1195                1200 act cct gga atg cca gga ttg atg gcg gga cca gga gcc gga ggt            5718
Thr Pro Gly Met Pro Gly Leu Met Ala Gly Pro Gly Ala Gly Gly
    1205                1210                1215 atg cta atg aat tct tcc gga gag caa cac cag aac aag atc aca            5763
Met Leu Met Asn Ser Ser Gly Glu Gln His Gln Asn Lys Ile Thr
    1220                1225                1230 aac aat cct ggg gca agc aat ggt att aac ttc ttt cag aat tgc            5808
Asn Asn Pro Gly Ala Ser Asn Gly Ile Asn Phe Phe Gln Asn Cys
    1235                1240                1245 aat caa atg tct att gtt gac gaa gag ggt gga tta ccc ggc cat            5853
Asn Gln Met Ser Ile Val Asp Glu Glu Gly Gly Leu Pro Gly His
    1250                1255                1260 gac gga tca atg aat att ggt caa cca tct atg ata agg ggc atg            5898
Asp Gly Ser Met Asn Ile Gly Gln Pro Ser Met Ile Arg Gly Met
    1265                1270                1275 cgt cca cat gcc atg cgg cca aat gta atg ggt gcg cgg atg cca            5943
Arg Pro His Ala Met Arg Pro Asn Val Met Gly Ala Arg Met Pro
    1280                1285                1290 ccc gtt aac agg caa att cag ttt gca cag tca tcg gat ggt att            5988
Pro Val Asn Arg Gln Ile Gln Phe Ala Gln Ser Ser Asp Gly Ile
    1295                1300                1305 gac tgt gtc ggg gat ccg tca tca ttt ttc act aac gct tcc tgc            6033
Asp Cys Val Gly Asp Pro Ser Ser Phe Phe Thr Asn Ala Ser Cys
    1310                1315                1320 aac agc gct gga cca cac atg ttt gga tca gca caa cag gcc aat            6078
Asn Ser Ala Gly Pro His Met Phe Gly Ser Ala Gln Gln Ala Asn
    1325                1330                1335 cag cct aag aca caa cac ata aag aac ata cct agt gga atg tgt            6123
Gln Pro Lys Thr Gln His Ile Lys Asn Ile Pro Ser Gly Met Cys
    1340                1345                1350 caa aac caa tcg gga ctt gca gtg gca caa ggg cag atc caa ctg            6168
Gln Asn Gln Ser Gly Leu Ala Val Ala Gln Gly Gln Ile Gln Leu
    1355                1360                1365 cat ggg caa gga cat gcg cag ggt cag tct tta att gga cct act            6213
His Gly Gln Gly His Ala Gln Gly Gln Ser Leu Ile Gly Pro Thr
    1370                1375                1380 aat aat aat tta atg tca act gcc gga agt gtc agt gct act aac            6258
Asn Asn Asn Leu Met Ser Thr Ala Gly Ser Val Ser Ala Thr Asn
    1385                1390                1395 ggt gtc tct ggc atc aat ttc gta ggt ccc tct tct acg gac ctg            6303
Gly Val Ser Gly Ile Asn Phe Val Gly Pro Ser Ser Thr Asp Leu
    1400                1405                1410 aag tat gcc cag caa tat cat agt ttt cag cag cag tta tat gct            6348
Lys Tyr Ala Gln Gln Tyr His Ser Phe Gln Gln Gln Leu Tyr Ala
    1415                1420                1425 acc aac acc aga agt caa caa caa cag cat atg cac cag cag cac            6393
Thr Asn Thr Arg Ser Gln Gln Gln Gln His Met His Gln Gln His
    1430                1435                1440 cag agc aac atg ata aca atg ccg ccg aat tta tca cca aat cca            6438
Gln Ser Asn Met Ile Thr Met Pro Pro Asn Leu Ser Pro Asn Pro
    1445                1450                1455 acg ttc ttt gtc aac aaa taaacttcta aattttgcc gccctcgtca               6486
Thr Phe Phe Val Asn Lys
    1460
```

-continued

```
tgtattgttt actagtctcc aaattaagac atgcatctct aaataagatt ttttgaagct      6546
tatttactta ggtgttttta caacggagaa aataaactt tggatatgca aatgataacg       6606
ttggaaacaa cataattcat ttgcaacttt tagaagtcac gtcgaagtta aatgtagaat      6666
ctgtatttta acataatagg tcatctgtaa aaataattaa acatcgaaat tttagttatc      6726
agcagctatt ttctgttatt atttaatatg tgcgctgctc tctctgtgtt aaatgaaatt      6786
aaaatatata tataaatgta aaacgctatt gatatatatt gctctcaact gtattgtaat      6846
caatattaag agaactgtaa attcttccat ataaggtaa tgaaaaaaaa aaaaaaaaa        6906 aaa                                                                    6909

<210> SEQ ID NO 2
<211> LENGTH: 28
<212> TYPE: PRT
<213> ORGANISM: Drosophila lgs

<400> SEQUENCE: 2

Ile Phe Val Phe Ser Thr Gln Leu Ala Asn Lys Gly Ala Glu Ser Val
1               5                   10                  15

Leu Ser Gly Gln Phe Gln Thr Ile Ile Ala Tyr His
            20                  25

<210> SEQ ID NO 3
<211> LENGTH: 28
<212> TYPE: PRT
<213> ORGANISM: Human lgs/bcl9

<400> SEQUENCE: 3

Val Tyr Val Phe Ser Thr Glu Met Ala Asn Lys Ala Ala Glu Ala Val
1               5                   10                  15

Leu Lys Gly Gln Val Glu Thr Ile Val Ser Phe His
            20                  25

<210> SEQ ID NO 4
<211> LENGTH: 35
<212> TYPE: PRT
<213> ORGANISM: Drosophila lgs

<400> SEQUENCE: 4

Glu Asn Leu Thr Pro Gln Gln Arg Gln His Arg Glu Glu Gln Leu Ala
1               5                   10                  15

Lys Ile Lys Lys Met Asn Gln Phe Leu Phe Pro Glu Asn Glu Asn Ser
            20                  25                  30

Val Gly Ala
        35

<210> SEQ ID NO 5
<211> LENGTH: 35
<212> TYPE: PRT
<213> ORGANISM: Human lgs/bcl9

<400> SEQUENCE: 5

Asp Gly Leu Ser Gln Glu Gln Leu Glu His Arg Glu Arg Ser Leu Gln
1               5                   10                  15

Thr Leu Arg Asp Ile Gln Arg Met Leu Phe Pro Asp Glu Lys Glu Phe
            20                  25                  30

Thr Gly Ala
        35
```

```
<210> SEQ ID NO 6
<211> LENGTH: 15
<212> TYPE: PRT
<213> ORGANISM: Drosophila lgs

<400> SEQUENCE: 6

Gln Met Glu Trp Ser Lys Ile Gln His Gln Phe Phe Glu Glu Arg
1               5                   10                  15

<210> SEQ ID NO 7
<211> LENGTH: 15
<212> TYPE: PRT
<213> ORGANISM: Human lgs/bcl9

<400> SEQUENCE: 7

Gln Ile Ala Trp Leu Lys Leu Gln Gln Glu Phe Tyr Glu Glu Lys
1               5                   10                  15

<210> SEQ ID NO 8
<211> LENGTH: 9
<212> TYPE: PRT
<213> ORGANISM: Drosophila lgs

<400> SEQUENCE: 8

Leu Gln Gly Pro Pro Pro Pro Tyr His
1               5

<210> SEQ ID NO 9
<211> LENGTH: 9
<212> TYPE: PRT
<213> ORGANISM: Human lgs/bcl9

<400> SEQUENCE: 9

Val Arg Gly Pro Pro Pro Pro Tyr Gln
1               5

<210> SEQ ID NO 10
<211> LENGTH: 112
<212> TYPE: PRT
<213> ORGANISM: Drosophila lgs

<400> SEQUENCE: 10

Ser Ala Ser Val Pro Ile Ala Thr Gln Ser Pro Asn Pro Ser Pro
1               5                   10                  15

Asn Asn Leu Ser Leu Pro Ser Pro Arg Thr Thr Ala Ala Val Met Gly
            20                  25                  30

Leu Pro Thr Asn Ser Pro Ser Met Asp Gly Thr Gly Ser Leu Ser Gly
        35                  40                  45

Ser Val Pro Gln Ala Asn Thr Ser Thr Val Gln Ala Gly Thr Thr Thr
    50                  55                  60

Val Leu Ser Ala Asn Lys Asn Cys Phe Gln Ala Asp Thr Pro Ser Pro
65                  70                  75                  80

Ser Asn Gln Asn Arg Ser Arg Asn Thr Gly Ser Ser Ser Val Leu Thr
                85                  90                  95

His Asn Leu Ser Ser Asn Pro Ser Thr Pro Leu Ser His Leu Ser Pro
            100                 105                 110

<210> SEQ ID NO 11
<211> LENGTH: 111
<212> TYPE: PRT
<213> ORGANISM: Human lgs/bcl9

<400> SEQUENCE: 11
```

```
Gly Pro Pro Pro Pro Thr Ala Ser Gln Pro Ala Ser Val Asn Ile Pro
1               5                   10                  15

Gly Ser Leu Pro Ser Ser Thr Pro Tyr Thr Met Pro Glu Pro Thr
            20                  25                  30

Leu Ser Gln Asn Pro Leu Ser Ile Met Met Ser Arg Met Ser Lys Phe
        35                  40                  45

Ala Met Pro Ser Ser Thr Pro Leu Tyr His Asp Ala Ile Lys Thr Val
50                  55                  60

Ala Ser Ser Asp Asp Ser Pro Pro Ala Arg Ser Pro Asn Leu Pro
65              70                  75                  80

Ser Met Asn Asn Met Pro Gly Met Gly Ile Asn Thr Gln Asn Pro Arg
                85                  90                  95

Ile Ser Gly Pro Asn Pro Val Val Pro Met Pro Thr Leu Ser Pro
            100                 105                 110

<210> SEQ ID NO 12
<211> LENGTH: 16
<212> TYPE: PRT
<213> ORGANISM: Drosophila lgs

<400> SEQUENCE: 12

Asn Pro Lys Met Cys Val Ala Gly Gly Pro Asn Gly Pro Pro Gly Phe
1               5                   10                  15

<210> SEQ ID NO 13
<211> LENGTH: 16
<212> TYPE: PRT
<213> ORGANISM: Human lgs/bcl9

<400> SEQUENCE: 13

Asp Ala Ala Leu Cys Lys Pro Gly Gly Pro Gly Gly Pro Asp Ser Phe
1               5                   10                  15

<210> SEQ ID NO 14
<211> LENGTH: 4281
<212> TYPE: DNA
<213> ORGANISM: Human lgs/bcl9

<400> SEQUENCE: 14
```

| | | |
|---|---|---|
| atgcattcca gtaaccctaa agtgaggagc tctccatcag aaacacaca gagtagccct | 60 |
| aagtcaaagc aggaggtgat ggtccgtccc cctacagtga tgtccccatc tggaaacccc | 120 |
| cagctggatt ccaaattctc caatcagggt aaacagggg gctcagccag ccaatcccag | 180 |
| ccatccccct gtgactccaa gagtgggggc cataccccta agcactccc tggcccaggt | 240 |
| gggagcatgg ggctgaagaa tggggctgga atggtgccaa agggcaaggg gaaaagggag | 300 |
| cgaagtattt ccgccgactc ctttgatcag agagatcctg ggactccaaa cgatgactct | 360 |
| gacattaaag aatgtaattc tgctgaccac ataaagtccc aggattccca gcacacacca | 420 |
| cactcgatga ccccatcaaa tgctacagcc cccaggtctt ctacccctc ccatggccaa | 480 |
| actactgcca cagagcccac acctgctcag aagactccag ccaaagtggt gtacgtgttt | 540 |
| tctactgaga tggccaataa agctgcagaa gctgttttga agggccaggt tgaaactatc | 600 |
| gtctcttcc acatccagaa catttctaac aacaagacag agagaagcac agcgcctctg | 660 |
| aacacacaga tatctgccct tcggaatgat ccgaaacctc tcccacaaca gcccccagct | 720 |
| ccggccaacc aggaccagaa ttcttcccag aataccagac tgcagccaac tccacccatt | 780 |
| ccggcaccag cacccaagcc tgccgcaccc ccacgtcccc tggaccggga gagtcctggg | 840 |

```
gtagaaaaca aactgattcc ttctgtagga agtcctgcca gctccactcc actgccccca    900
gatggtactg ggcccaactc aactcccaac aatagggcag tgaccoctgt ctcccagggg    960
agcaatagct cttcagcaga tcccaaagcc cctccgcctc caccagtgtc cagtggcgag   1020
ccccccacac tgggagagaa tcccgatggc ctatctcagg agcagctgga gcaccgggag   1080
cgctccttac aaactctcag agatatccag cgcatgcttt ttcctgatga aaagaattc    1140
acaggagcac aaagtggggg accgcagcag aatcctgggg tattagatgg gcctcagaaa   1200
aaaccgaaag ggccaataca ggccatgatg gcccaatccc aaagcctagg taagggacct   1260
gggcccccgga cagacgtggg agctccattt ggccctcaag gacatagaga tgtacccttt   1320
tctccagatg aaatggttcc accttctatg aactcccagt ctgggaccat aggacccgac   1380
caccttgacc atatgactcc cgagcagata gcgtggctga aactgcagca ggagttttat   1440
gaagagaaga ggaggaagca ggaacaagtg gttgtccagc agtgttccct ccaggacatg   1500
atggtccatc agcacgggcc tcggggagtg gtccgaggac ccccccctcc ataccagatg   1560
accccctagtg aaggctgggc acctgggggt acagagccat tttctgatgg tatcaacatg   1620
ccacattctc tgccccgag gggcatggct ccccacccca acatgccagg gagccagatg   1680
cgcctccctg gatttgcagg catgataaac tctgaaatgg aagggccgaa tgtccccaac   1740
cctgcatcta gaccaggtct ttctggagtc agttggccag atgatgtgcc aaaaatccca   1800
gatggtcgaa attttcctcc tggccagggc attttcagcg gtcctggccg aggggaacgc   1860
ttcccaaacc cccaaggatt gtctgaagag atgtttcagc agcagctggc agagaaacag   1920
ctgggtctcc ccccagggat ggccatggaa ggcatcaggc ccagcatgga gatgaacagg   1980
atgattccag gctcccagcg ccacatggag cctgggaata ccccatttt ccctcgaata   2040
ccagttgagg gccctctgag tccttctagg ggtgactttc caaaaggaat tcccccacag   2100
atgggccctg gtcgggaact tgagtttggg atggttccta gtgggatgaa gggagatgtc   2160
aatctaaatg tcaacatggg atccaactct cagatgatac ctcagaagat gagagaggct   2220
ggggcgggcc ctgaggagat gctgaaatta cgcccaggtg gctcagacat gctgcctgct   2280
cagcagaaga tggtgccact gccatttggt gagcaccccc agcaggagta tggcatgggc   2340
cccagaccat tccttcccat gtctcagggt ccaggcagca acagtggctt gcggaatctc   2400
agagaaccaa ttgggcccga ccagaggact aacagccggc tcagtcatat gccaccacta   2460
cctctcaacc cttccagtaa ccccaccagc ctcaacacag ctcctccagt tcagcgcggc   2520
ctggggcgga agcccttgga tatatctgtg gcaggcagcc aggtgcattc cccaggcatt   2580
aaccctctga gtctcccac gatgcaccaa gtccagtcac caatgctggg ctcgccctcg   2640
gggaacctca gtcccccca gactccatcg cagctggcag gcatgctggc gggcccagct   2700
gctgctgctt ccattaagtc ccccctgtt ttggggtctg ctgctgcttc acctgtccac   2760
ctcaagtctc catcacttcc tgccccgtca cctggatgga cctcttctcc aaaacctccc   2820
cttcagagtc ctgggatccc tccaaaccat aaagcacccc tcaccatggc ctccccagcc   2880
atgctgggaa atgtagagtc aggtggcccc ccacctccta cagccagcca gctgcctct    2940
gtgaatatcc ctggaagtct tccctctagt acaccttata ccatgcctcc agagccaacc   3000
cttttcccaga acccactctc tattatgatg tctcgaatgt ccaagtttgc aatgcccagt   3060
tccaccccgt tataccatga tgctatcaag actgtggcca gctcagatga cgactcccct   3120
ccagctcgtt ctcccaactt gccatcaatg aataatatgc caggaatggg cattaataca   3180
```

-continued

```
cagaatcctc gaatttcagg tccaaacccc gtggttccga tgccaaccct cagcccaatg    3240
ggaatgaccc agccactttc tcactccaat cagatgccct ctccaaatgc cgtgggaccc    3300
aacatacctc ctcatggggt cccaatgggg cctggcttga tgtcacacaa tcctatcatg    3360
gggcatgggt cccaggagcc accgatggta cctcaaggac ggatgggctt ccccccagggc   3420 ttccctccag tacagtctcc cccacagcag gttccattcc ctcacaatgg ccccagtggg    3480
gggcagggca gcttcccagg agggatgggt ttcccaggaa aaggcccct tggccgcccc     3540 agcaacctgc cccaaagttc agcagatgca gcactttgca agcctggagg ccccgggggt    3600
cctgactcct tcactgtcct ggggaacagc atgccttcgg tgtttacaga cccagatctg    3660
caggaggtca tccgacctgg agccaccgga atacctgagt ttgatctatc ccgcattatt    3720
ccatctgaga agcccagcca gacgctgcaa tatttccctc gaggggaagt tccaggccgt    3780
aaacagcccc agggtcctgg acctgggttt tcacacatgc aggggatgat gggcgaacaa    3840
gcccccagaa tggactagc attacctggc atgggaggtc cagggccagt gggaactccg     3900
gacatccctc ttggtacagc tccatccatg ccaggccaca accccatgag accaccagcc    3960
tttctccaac aaggcatgat gggacctcac atcggatga tgtcaccagc acaatctaca     4020
atgcccggcc agcccaccct gatgagcaat ccagctgctg ccgtgggcat gattcctggc    4080
aaggatcggg ggcctgccgg gctctacacc caccctgggc ctgtgggctc tccaggcatg    4140
atgatgtcca tgcagggcat gatgggaccc caacagaaca tcatgatccc cccacagatg    4200
aggccccggg gcatggctgc tgacgtgggc atgggtggat ttagccaagg acctggcaac    4260
ccaggaaaca tgatgtttta a                                              4281
```

<210> SEQ ID NO 15
<211> LENGTH: 1426
<212> TYPE: PRT
<213> ORGANISM: Human lgs/bcl9

<400> SEQUENCE: 15

```
Met His Ser Ser Asn Pro Lys Val Arg Ser Pro Ser Gly Asn Thr
  1               5                  10                  15

Gln Ser Ser Pro Lys Ser Lys Gln Glu Val Met Val Arg Pro Pro Thr
             20                  25                  30

Val Met Ser Pro Ser Gly Asn Pro Gln Leu Asp Ser Lys Phe Ser Asn
         35                  40                  45

Gln Gly Lys Gln Gly Gly Ser Ala Ser Gln Ser Gln Pro Ser Pro Cys
     50                  55                  60

Asp Ser Lys Ser Gly Gly His Thr Pro Lys Ala Leu Pro Gly Pro Gly
 65                  70                  75                  80

Gly Ser Met Gly Leu Lys Asn Gly Ala Gly Asn Ala Lys Gly Lys
                 85                  90                  95

Gly Lys Arg Glu Arg Ser Ile Ser Ala Asp Ser Phe Asp Gln Arg Asp
                100                 105                 110

Pro Gly Thr Pro Asn Asp Asp Ser Asp Ile Lys Glu Cys Asn Ser Ala
            115                 120                 125

Asp His Ile Lys Ser Gln Asp Ser Gln His Thr Pro His Ser Met Thr
        130                 135                 140

Pro Ser Asn Ala Thr Ala Pro Arg Ser Ser Thr Pro Ser His Gly Gln
145                 150                 155                 160

Thr Thr Ala Thr Glu Pro Thr Pro Ala Gln Lys Thr Pro Ala Lys Val
                165                 170                 175
```

```
Val Tyr Val Phe Ser Thr Glu Met Ala Asn Lys Ala Ala Glu Ala Val
            180                 185                 190

Leu Lys Gly Gln Val Glu Thr Ile Val Ser Phe His Ile Gln Asn Ile
        195                 200                 205

Ser Asn Asn Lys Thr Glu Arg Ser Thr Ala Pro Leu Asn Thr Gln Ile
    210                 215                 220

Ser Ala Leu Arg Asn Asp Pro Lys Pro Leu Pro Gln Gln Pro Pro Ala
225                 230                 235                 240

Pro Ala Asn Gln Asp Gln Asn Ser Ser Gln Asn Thr Arg Leu Gln Pro
                245                 250                 255

Thr Pro Pro Ile Pro Ala Pro Ala Pro Lys Pro Ala Ala Pro Pro Arg
            260                 265                 270

Pro Leu Asp Arg Glu Ser Pro Gly Val Glu Asn Lys Leu Ile Pro Ser
        275                 280                 285

Val Gly Ser Pro Ala Ser Ser Thr Pro Leu Pro Pro Asp Gly Thr Gly
    290                 295                 300

Pro Asn Ser Thr Pro Asn Asn Arg Ala Val Thr Pro Val Ser Gln Gly
305                 310                 315                 320

Ser Asn Ser Ser Ser Ala Asp Pro Lys Ala Pro Pro Pro Pro Pro Val
                325                 330                 335

Ser Ser Gly Glu Pro Pro Thr Leu Gly Glu Asn Pro Asp Gly Leu Ser
            340                 345                 350

Gln Glu Gln Leu Glu His Arg Glu Arg Ser Leu Gln Thr Leu Arg Asp
        355                 360                 365

Ile Gln Arg Met Leu Phe Pro Asp Glu Lys Glu Phe Thr Gly Ala Gln
    370                 375                 380

Ser Gly Gly Pro Gln Gln Asn Pro Gly Val Leu Asp Gly Pro Gln Lys
385                 390                 395                 400

Lys Pro Glu Gly Pro Ile Gln Ala Met Met Ala Gln Ser Gln Ser Leu
                405                 410                 415

Gly Lys Gly Pro Gly Pro Arg Thr Asp Val Gly Ala Pro Phe Gly Pro
            420                 425                 430

Gln Gly His Arg Asp Val Pro Phe Ser Pro Asp Glu Met Val Pro Pro
        435                 440                 445

Ser Met Asn Ser Gln Ser Gly Thr Ile Gly Pro Asp His Leu Asp His
    450                 455                 460

Met Thr Pro Glu Gln Ile Ala Trp Leu Lys Leu Gln Gln Glu Phe Tyr
465                 470                 475                 480

Glu Glu Lys Arg Arg Lys Gln Glu Gln Val Val Gln Gln Cys Ser
                485                 490                 495

Leu Gln Asp Met Met Val His Gln His Gly Pro Arg Gly Val Val Arg
            500                 505                 510

Gly Pro Pro Pro Pro Tyr Gln Met Thr Pro Ser Glu Gly Trp Ala Pro
        515                 520                 525

Gly Gly Thr Glu Pro Phe Ser Asp Gly Ile Asn Met Pro His Ser Leu
    530                 535                 540

Pro Pro Arg Gly Met Ala Pro His Pro Asn Met Pro Gly Ser Gln Met
545                 550                 555                 560

Arg Leu Pro Gly Phe Ala Gly Met Ile Asn Ser Glu Met Glu Gly Pro
                565                 570                 575

Asn Val Pro Asn Pro Ala Ser Arg Pro Gly Leu Ser Gly Val Ser Trp
            580                 585                 590

Pro Asp Asp Val Pro Lys Ile Pro Asp Gly Arg Asn Phe Pro Pro Gly
```

-continued

```
                595                 600                 605
Gln Gly Ile Phe Ser Gly Pro Gly Arg Gly Glu Arg Phe Pro Asn Pro
    610                 615                 620
Gln Gly Leu Ser Glu Glu Met Phe Gln Gln Leu Ala Glu Lys Gln
625                 630                 635                 640
Leu Gly Leu Pro Pro Gly Met Ala Met Glu Gly Ile Arg Pro Ser Met
                645                 650                 655
Glu Met Asn Arg Met Ile Pro Gly Ser Gln Arg His Met Glu Pro Gly
            660                 665                 670
Asn Asn Pro Ile Phe Pro Arg Ile Pro Val Glu Gly Pro Leu Ser Pro
            675                 680                 685
Ser Arg Gly Asp Phe Pro Lys Gly Ile Pro Pro Gln Met Gly Pro Gly
    690                 695                 700
Arg Glu Leu Glu Phe Gly Met Val Pro Ser Gly Met Lys Gly Asp Val
705                 710                 715                 720
Asn Leu Asn Val Asn Met Gly Ser Asn Ser Gln Met Ile Pro Gln Lys
                725                 730                 735
Met Arg Glu Ala Gly Ala Gly Pro Glu Glu Met Leu Lys Leu Arg Pro
            740                 745                 750
Gly Gly Ser Asp Met Leu Pro Ala Gln Gln Lys Met Val Pro Leu Pro
    755                 760                 765
Phe Gly Glu His Pro Gln Gln Glu Tyr Gly Met Gly Pro Arg Pro Phe
    770                 775                 780
Leu Pro Met Ser Gln Gly Pro Gly Ser Asn Ser Gly Leu Arg Asn Leu
785                 790                 795                 800
Arg Glu Pro Ile Gly Pro Asp Gln Arg Thr Asn Ser Arg Leu Ser His
                805                 810                 815
Met Pro Pro Leu Pro Leu Asn Pro Ser Ser Asn Pro Thr Ser Leu Asn
            820                 825                 830
Thr Ala Pro Pro Val Gln Arg Gly Leu Gly Arg Lys Pro Leu Asp Ile
        835                 840                 845
Ser Val Ala Gly Ser Gln Val His Ser Pro Gly Ile Asn Pro Leu Lys
    850                 855                 860
Ser Pro Thr Met His Gln Val Gln Ser Pro Met Leu Gly Ser Pro Ser
865                 870                 875                 880
Gly Asn Leu Lys Ser Pro Gln Thr Pro Ser Gln Leu Ala Gly Met Leu
                885                 890                 895
Ala Gly Pro Ala Ala Ala Ser Ile Lys Ser Pro Val Leu Gly
            900                 905                 910
Ser Ala Ala Ser Pro Val His Leu Lys Ser Pro Ser Leu Pro Ala
        915                 920                 925
Pro Ser Pro Gly Trp Thr Ser Ser Lys Pro Pro Leu Gln Ser Pro
    930                 935                 940
Gly Ile Pro Pro Asn His Lys Ala Pro Leu Thr Met Ala Ser Pro Ala
945                 950                 955                 960
Met Leu Gly Asn Val Glu Ser Gly Gly Pro Pro Pro Thr Ala Ser
                965                 970                 975
Gln Pro Ala Ser Val Asn Ile Pro Gly Ser Leu Pro Ser Ser Thr Pro
            980                 985                 990
Tyr Thr Met Pro Pro Glu Pro Thr  Leu Ser Gln Asn Pro  Leu Ser Ile
        995                 1000                1005
Met Met  Ser Arg Met Ser Lys  Phe Ala Met Pro Ser  Ser Thr Pro
    1010                1015                1020
```

-continued

```
Leu Tyr His Asp Ala Ile Lys Thr Val Ala Ser Ser Asp Asp Asp
    1025                1030                1035

Ser Pro Pro Ala Arg Ser Pro Asn Leu Pro Ser Met Asn Asn Met
    1040                1045                1050

Pro Gly Met Gly Ile Asn Thr Gln Asn Pro Arg Ile Ser Gly Pro
    1055                1060                1065

Asn Pro Val Val Pro Met Pro Thr Leu Ser Pro Met Gly Met Thr
    1070                1075                1080

Gln Pro Leu Ser His Ser Asn Gln Met Pro Ser Pro Asn Ala Val
    1085                1090                1095

Gly Pro Asn Ile Pro Pro His Gly Val Pro Met Gly Pro Gly Leu
    1100                1105                1110

Met Ser His Asn Pro Ile Met Gly His Gly Ser Gln Glu Pro Pro
    1115                1120                1125

Met Val Pro Gln Gly Arg Met Gly Phe Pro Gln Gly Phe Pro Pro
    1130                1135                1140

Val Gln Ser Pro Pro Gln Gln Val Pro Phe Pro His Asn Gly Pro
    1145                1150                1155

Ser Gly Gly Gln Gly Ser Phe Pro Gly Gly Met Gly Phe Pro Gly
    1160                1165                1170

Glu Gly Pro Leu Gly Arg Pro Ser Asn Leu Pro Gln Ser Ser Ala
    1175                1180                1185

Asp Ala Ala Leu Cys Lys Pro Gly Gly Pro Gly Gly Pro Asp Ser
    1190                1195                1200

Phe Thr Val Leu Gly Asn Ser Met Pro Ser Val Phe Thr Asp Pro
    1205                1210                1215

Asp Leu Gln Glu Val Ile Arg Pro Gly Ala Thr Gly Ile Pro Glu
    1220                1225                1230

Phe Asp Leu Ser Arg Ile Ile Pro Ser Glu Lys Pro Ser Gln Thr
    1235                1240                1245

Leu Gln Tyr Phe Pro Arg Gly Glu Val Pro Gly Arg Lys Gln Pro
    1250                1255                1260

Gln Gly Pro Gly Pro Gly Phe Ser His Met Gln Gly Met Met Gly
    1265                1270                1275

Glu Gln Ala Pro Arg Met Gly Leu Ala Leu Pro Gly Met Gly Gly
    1280                1285                1290

Pro Gly Pro Val Gly Thr Pro Asp Ile Pro Leu Gly Thr Ala Pro
    1295                1300                1305

Ser Met Pro Gly His Asn Pro Met Arg Pro Pro Ala Phe Leu Gln
    1310                1315                1320

Gln Gly Met Met Gly Pro His His Arg Met Met Ser Pro Ala Gln
    1325                1330                1335

Ser Thr Met Pro Gly Gln Pro Thr Leu Met Ser Asn Pro Ala Ala
    1340                1345                1350

Ala Val Gly Met Ile Pro Gly Lys Asp Arg Gly Pro Ala Gly Leu
    1355                1360                1365

Tyr Thr His Pro Gly Pro Val Gly Ser Pro Gly Met Met Met Ser
    1370                1375                1380

Met Gln Gly Met Met Gly Pro Gln Gln Asn Ile Met Ile Pro Pro
    1385                1390                1395

Gln Met Arg Pro Arg Gly Met Ala Ala Asp Val Gly Met Gly Gly
    1400                1405                1410
```

```
    Phe Ser Gln Gly Pro Gly Asn Pro Gly Asn Met Met Phe
        1415                1420                1425

<210> SEQ ID NO 16
<211> LENGTH: 3948
<212> TYPE: DNA
<213> ORGANISM: Human lgs-1

<400> SEQUENCE: 16
atggcctgct tcccatcccc tgctgccatc tcctgcaccc ttagggcaca gtgggcatct      60
cgggagctgc tcagcggaca gactagggtt accccccaccc caggaggaga gaagctccag    120
ggagcccgcc gctgtccccc gcggtcattg cccctgccc cagccaagcc aatgcaccca      180
gaaaataaat tgaccaatca tggcaagaca gggaatggcg gggcccaatc tcagcaccag    240
aatgtgaacc aaggacccac ctgcaacgtg ggctcgaagg gcgtgggggc gggaaccat     300 ggggccaagg ccaaccagat ctcgcctagc aactcaagtc tgaagaaccc ccaggcaggg    360 gtgcccccttt tcagctcgct caagggcaag gtgaagaggg accggagtgt gtctgtggac    420
tctggagagc agcgagaggc tggaccccca tccctggatt cagaggccaa agaggtggcg    480
ccgcggagta gcggcgctg tgtgctggag cggaagcagc cgtacagtgg ggacgaatgg     540
tgctctggac cggacagtga ggaggacgac aagcccattg gggccacccca caaagctgct    600 ttcaaagaag acggctttca ggacaaggca tcacacttct ctccagcac gtacagtcct    660 gaaacctcca ggaggaagct gccccaagcc ccgaaggctt ccttcctggg gcagcagggc    720
cgagtcattt ggaaacctct ctcggaggag ctccgtgatc aaggtgcaga tgcggcaggt    780
gggccggcct caatcatgtc tccaatcgcg acggtgaatg cgagtggctt gtccaaagag    840
cagctggagc atcggaaacg gtccctccag acgctgcgag acattgagcg actgctgctc    900
cgcagcggag agactgagcc cttcctcaag ggggccccca ggaggagcgg cgggctgaag    960
aaatatgagg aacccttgca gtccatgatt tcacagacac agagcctagg ggcccccccg   1020
ctggagcatg aagtgcctgg gcaccccccg ggtggggaca tggggcagca gatgaacatg   1080
atgatacaga ggctgggcca ggacagcctc acgcctgagc aggtggcctg cgcaagctg    1140 caggaggagt actacgaaga gaaacggcgg aaagaggaac agattgggct gcatgggagc   1200
cgtcctctgc aggacatgat gggcatgggg gcatgatgg tgagggggcc ccgcctcct    1260 taccacagca agcctgggga tcagtggcca cctggaatgg gtgcgcagct gcgggggccc   1320
atggatgttc aagatcccat gcagctccgg gcggacctc cctttcctgg gccccgtttc   1380
ccaggcaacc agatacaacg ggtacctggg tttgggggca tgcagagtat gcccatggag   1440
gtgcccatga atgccatgca gaggcccgtg agaccaggca tgggctggac cgaagacttg   1500 cccccctatgg ggggacccag caattttgcc cagaacacca tgccctaccc aggtgggcag   1560
ggtgaggcgg agcgattcat gactccccgg gtccgtgagg agctgctgcg caccagctg    1620 ctggagaagc ggtcgatggg catgcagcgc ccctgggca tggcaggcag tggcatggga   1680
cagagcatgg agatggagcg gatgatgcag gcgcaccgac agatggatcc tgccatgttt   1740
cccgggcaga tggctggtgg tgagggcctg gcgggcactc ccatgggcat ggagtttggt   1800
ggaggccggg gcctcctgag ccctcccatg gggcagtctg gctgaggga ggtgacccca   1860 cccatggggc caggcaacct caacatgaac atgaatgtca acatgaacat gaacatgaac   1920
ctgaacgtgc agatgacccc gcagcagcag atgctgatgt cgcagaagat gcggggccct   1980
ggggacttga tggggcccca gggcctcagt cctgaggaga tggcccgggt tcgggcccag   2040
```

-continued

```
aacagcagtg gcatggtgcc cttgccttct gccaacccgc caggacctct caagtcgccc    2100
caggtcctcg gctcctccct cagtgtccgt tcacccactg gctcgcccag caggctcaag    2160
tctccttcca tggcggtgcc ttctccaggc tgggttgcct cacccaagac ggccatgccc    2220
agcccggggg tctcccagaa caagcagccg cctctcaaca tgaactcttc caccaccctg    2280
agcaacatgg aacaggaccc cacaccttcc cagaacccc tgtcactgat gatgacccag    2340
atgtccaagt acgccatgcc cagctccacc ccgctctacc acaatgccat caagaccatc    2400
gccacctcag acgacgagct gctgcccgac cggcccctgc tgccccccc accaccaccg    2460 cagggctccg ggccaggtgg cccgactcc ctgaatgccc cctgtggccc agtgcccagc    2520
tcctcccaga tgatgccctt cccccctcgg ctgcagcagc ccatggtgc catggccccc    2580 actggggtg gggcggggg gcctggcctg cagcagcact acccgtcagg catggccctg    2640
cctcccgagg acctgcccaa ccagccgcca ggccccatgc ctccccagca gcacctgatg    2700
ggcaaagcca tggctgggcg catgggcgac gcatacccac cgggtgtgct ccctggggtg    2760
gcatcagtgc tgaacgaccc cgagctgagc gaggtgatcc ggcccacccc aacggggatc    2820
cccgagttcg acttgtcgag gatcatcccc tctgagaagc caagcagcac cctccagtac    2880
ttccccaaga gcgagaacca gccccccaag gctcagcccc ctaatctgca tctcatgaac    2940
ctgcagaaca tgatggcgga gcagactccc tctcggcctc ccaacctccc aggccagcag    3000
ggcgatcggc cgctggtggt ggtgataccg ggtacccggg ctatggcgcc ggcgcagcgc    3060
tgccctctgt gccgccagac cttcttctgt ggtcgcgggc acgtttacag ccgcaagcac    3120
cagcggcagc tgaaggaggc tttggagagg ctcctgcccc aggtggaggc ggcccgcaag    3180
gccatccgcg ccgctcaggt ggagcgctat gtgcccgaac acgagcgatg ctgctggtgc    3240
ctgtgctgcg gctgtgaggt gcgggaacac ctgagccatg gaaacctgac ggtgctgtac    3300
ggggggctgc tggagcatct ggccagccca gagcacaaga agcaaccaa caaattctgg    3360 tgggagaaca agctgaggt ccagatgaaa gagaagtttc tggtcactcc ccaggattat    3420
gcgcgattca agaaatccat ggtgaaaggt ttggattcct atgaagaaaa ggaggataaa    3480
gtgatcaagg agatggcagc tcagatccgt gaggtggagc agagccgaca ggaggtggtt    3540
cggtctgtct tagagacagg tcccccaaga tacgccctca cagtccggtc ccccgccgtc    3600
ctctcccggc gcacgctcaa gtccggtgcc ttccccccgc agaccccga ggcgcaccct    3660 caagctcggt gcctctgcgc ccccgcagg ggcgccctca gcctgagcc ccgggcgc     3720 accctcaagc tcggtgtacc ccccatacc acccgcaagg cgcgccctca tgccgcgaag    3780
acttcgcccc gccaaggtg cacccgtcaa gccccgaata aacccagtc actccaactt    3840 gcaggcaaag ctagaaaaac tgcgctgcat ttgcaaacaa aagctcttgt tggcgatgac    3900
gatactgttt tgggtgtgaa actgtcaatt gctaactacg atctgtga              3948
```

<210> SEQ ID NO 17
<211> LENGTH: 1115
<212> TYPE: PRT
<213> ORGANISM: Human lgs-1

<400> SEQUENCE: 17

```
Phe Lys Glu Asp Gly Phe Gln Asp Lys Ala Ser His Phe Phe Ser Ser
1               5                   10                  15

Thr Tyr Ser Pro Glu Thr Ser Arg Arg Lys Leu Pro Gln Ala Pro Lys
            20                  25                  30

Ala Ser Phe Leu Gly Gln Gln Gly Arg Val Ile Trp Lys Pro Leu Ser
```

-continued

```
                35                  40                  45
Glu Glu Leu Arg Asp Gln Gly Ala Asp Ala Ala Gly Gly Pro Ala Ser
 50                  55                  60
Ile Met Ser Pro Ile Ala Thr Val Asn Ala Ser Gly Leu Ser Lys Glu
65                  70                  75                  80
Gln Leu Glu His Arg Glu Arg Ser Leu Gln Thr Leu Arg Asp Ile Glu
                85                  90                  95
Arg Leu Leu Leu Arg Ser Gly Glu Thr Glu Pro Phe Leu Lys Gly Ala
                100                 105                 110
Pro Arg Arg Ser Gly Gly Leu Lys Lys Tyr Glu Glu Pro Leu Gln Ser
                115                 120                 125
Met Ile Ser Gln Thr Gln Ser Leu Gly Gly Pro Leu Glu His Glu
                130                 135                 140
Val Pro Gly His Pro Pro Gly Gly Asp Met Gly Gln Gln Met Asn Met
145                 150                 155                 160
Met Ile Gln Arg Leu Gly Gln Asp Ser Leu Thr Pro Glu Gln Val Ala
                165                 170                 175
Trp Arg Lys Leu Gln Glu Glu Tyr Tyr Glu Glu Lys Arg Arg Lys Glu
                180                 185                 190
Glu Gln Ile Gly Leu His Gly Ser Arg Pro Leu Gln Asp Met Met Gly
                195                 200                 205
Met Gly Gly Met Met Val Arg Gly Pro Pro Pro Tyr His Ser Lys
                210                 215                 220
Pro Gly Asp Gln Trp Pro Pro Gly Met Gly Ala Gln Leu Arg Gly Pro
225                 230                 235                 240
Met Asp Val Gln Asp Pro Met Gln Leu Arg Gly Gly Pro Pro Phe Pro
                245                 250                 255
Gly Pro Arg Phe Pro Gly Asn Gln Ile Gln Arg Val Pro Gly Phe Gly
                260                 265                 270
Gly Met Gln Ser Met Pro Met Glu Val Pro Met Asn Ala Met Gln Arg
                275                 280                 285
Pro Val Arg Pro Gly Met Gly Trp Thr Glu Asp Leu Pro Pro Met Gly
                290                 295                 300
Gly Pro Ser Asn Phe Ala Gln Asn Thr Met Pro Tyr Pro Gly Gly Gln
305                 310                 315                 320
Gly Glu Ala Glu Arg Phe Met Thr Pro Arg Val Arg Glu Glu Leu Leu
                325                 330                 335
Arg His Gln Leu Leu Glu Lys Arg Ser Met Gly Met Gln Arg Pro Leu
                340                 345                 350
Gly Met Ala Gly Ser Gly Met Gly Gln Ser Met Glu Met Glu Arg Met
                355                 360                 365
Met Gln Ala His Arg Gln Met Asp Pro Ala Met Phe Pro Gly Gln Met
                370                 375                 380
Ala Gly Gly Glu Gly Leu Ala Gly Thr Pro Met Gly Met Glu Phe Gly
385                 390                 395                 400
Gly Gly Arg Gly Leu Leu Ser Pro Pro Met Gly Gln Ser Gly Leu Arg
                405                 410                 415
Glu Val Asp Pro Pro Met Gly Pro Gly Asn Leu Asn Met Asn Met Asn
                420                 425                 430
Val Asn Met Asn Met Asn Met Asn Leu Asn Val Gln Met Thr Pro Gln
                435                 440                 445
Gln Gln Met Leu Met Ser Gln Lys Met Arg Gly Pro Gly Asp Leu Met
                450                 455                 460
```

```
Gly Pro Gln Gly Leu Ser Pro Glu Glu Met Ala Arg Val Arg Ala Gln
465                 470                 475                 480

Asn Ser Ser Gly Met Val Pro Leu Pro Ser Ala Asn Pro Pro Gly Pro
            485                 490                 495

Leu Lys Ser Pro Gln Val Leu Gly Ser Ser Leu Ser Val Arg Ser Pro
        500                 505                 510

Thr Gly Ser Pro Ser Arg Leu Lys Ser Pro Ser Met Ala Val Pro Ser
            515                 520                 525

Pro Gly Trp Val Ala Ser Pro Lys Thr Ala Met Pro Ser Pro Gly Val
        530                 535                 540

Ser Gln Asn Lys Gln Pro Pro Leu Asn Met Asn Ser Ser Thr Thr Leu
545                 550                 555                 560

Ser Asn Met Glu Gln Asp Pro Thr Pro Ser Gln Asn Pro Leu Ser Leu
            565                 570                 575

Met Met Thr Gln Met Ser Lys Tyr Ala Met Pro Ser Ser Thr Pro Leu
        580                 585                 590

Tyr His Asn Ala Ile Lys Thr Ile Ala Thr Ser Asp Asp Glu Leu Leu
            595                 600                 605

Pro Asp Arg Pro Leu Leu Pro Pro Pro Pro Gln Gly Ser Gly
        610                 615                 620

Pro Gly Gly Pro Asp Ser Leu Asn Ala Pro Cys Gly Pro Val Pro Ser
625                 630                 635                 640

Ser Ser Gln Met Met Pro Phe Pro Pro Arg Leu Gln Gln Pro His Gly
                645                 650                 655

Ala Met Ala Pro Thr Gly Gly Gly Gly Gly Pro Gly Leu Gln Gln
        660                 665                 670

His Tyr Pro Ser Gly Met Ala Leu Pro Pro Glu Asp Leu Pro Asn Gln
            675                 680                 685

Pro Pro Gly Pro Met Pro Gln Gln His Leu Met Gly Lys Ala Met
        690                 695                 700

Ala Gly Arg Met Gly Asp Ala Tyr Pro Pro Gly Val Leu Pro Gly Val
705                 710                 715                 720

Ala Ser Val Leu Asn Asp Pro Glu Leu Ser Glu Val Ile Arg Pro Thr
            725                 730                 735

Pro Thr Gly Ile Pro Glu Phe Asp Leu Ser Arg Ile Ile Pro Ser Glu
        740                 745                 750

Lys Pro Ser Ser Thr Leu Gln Tyr Phe Pro Lys Ser Glu Asn Gln Pro
            755                 760                 765

Pro Lys Ala Gln Pro Pro Asn Leu His Leu Met Asn Leu Gln Asn Met
        770                 775                 780

Met Ala Glu Gln Thr Pro Ser Arg Pro Pro Asn Leu Pro Gly Gln Gln
785                 790                 795                 800

Gly Asp Arg Pro Leu Val Val Ile Pro Gly Thr Arg Ala Met Ala
            805                 810                 815

Pro Ala Gln Arg Cys Pro Leu Cys Arg Gln Thr Phe Phe Cys Gly Arg
        820                 825                 830

Gly His Val Tyr Ser Arg Lys His Gln Arg Gln Leu Lys Glu Ala Leu
            835                 840                 845

Glu Arg Leu Leu Pro Gln Val Glu Ala Ala Arg Lys Ala Ile Arg Ala
        850                 855                 860

Ala Gln Val Glu Arg Tyr Val Pro Glu His Glu Arg Cys Cys Trp Cys
865                 870                 875                 880
```

-continued

```
Leu Cys Cys Gly Cys Glu Val Arg Glu His Leu Ser His Gly Asn Leu
            885                 890                 895

Thr Val Leu Tyr Gly Gly Leu Leu Glu His Leu Ala Ser Pro Glu His
        900                 905                 910

Lys Lys Ala Thr Asn Lys Phe Trp Trp Glu Asn Lys Ala Glu Val Gln
    915                 920                 925

Met Lys Glu Lys Phe Leu Val Thr Pro Gln Asp Tyr Ala Arg Phe Lys
930                 935                 940

Lys Ser Met Val Lys Gly Leu Asp Ser Tyr Glu Gln Lys Glu Asp Lys
945                 950                 955                 960

Val Ile Lys Glu Met Ala Ala Gln Ile Arg Glu Val Glu Gln Ser Arg
                965                 970                 975

Gln Glu Val Val Arg Ser Val Leu Glu Thr Gly Pro Pro Arg Tyr Ala
            980                 985                 990

Leu Thr Val Arg Ser Pro Ala Val  Leu Ser Arg Arg Thr  Leu Lys Ser
        995                 1000                1005

Gly Ala  Phe Pro Pro Gln Thr  Pro Glu Ala His Pro  Gln Ala Arg
    1010                1015                1020

Cys Leu  Cys Ala Pro Arg Arg  Gly Ala Leu Lys Pro  Glu Pro Pro
    1025                1030                1035

Gly Arg  Thr Leu Lys Leu Gly  Val Pro Pro His Thr  Thr Arg Lys
    1040                1045                1050

Ala Arg  Pro His Ala Ala Lys  Thr Ser Pro Arg Pro  Arg Cys Thr
    1055                1060                1065

Arg Gln  Ala Pro Asn Lys Thr  Gln Ser Leu Gln Leu  Ala Gly Lys
    1070                1075                1080

Ala Arg  Lys Thr Ala Leu His  Leu Gln Thr Lys Ala  Leu Val Gly
    1085                1090                1095

Asp Asp  Asp Thr Val Leu Gly  Val Lys Leu Ser Ile  Ala Asn Tyr
    1100                1105                1110

Asp Leu
    1115

<210> SEQ ID NO 18
<211> LENGTH: 49
<212> TYPE: DNA
<213> ORGANISM: Artificial Sequence
<220> FEATURE:
<221> NAME/KEY: misc_structure
<222> LOCATION: (1)..(49)
<223> OTHER INFORMATION: T7 Promoter containing dsRNA-lgs-R1

<400> SEQUENCE: 18
taatacgact cactataggg agaccacttc catgctcatt tcgtcatta                49

<210> SEQ ID NO 19
<211> LENGTH: 48
<212> TYPE: DNA
<213> ORGANISM: Artificial Sequence
<220> FEATURE:
<221> NAME/KEY: misc_structure
<222> LOCATION: (1)..(48)
<223> OTHER INFORMATION: dsRNA-lgs-F1

<400> SEQUENCE: 19
taatacgact cactataggg agaccactag gatctctcga caacaatg                 48

<210> SEQ ID NO 20
<211> LENGTH: 49
```

```
<212> TYPE: DNA
<213> ORGANISM: Artificial Sequence
<220> FEATURE:
<221> NAME/KEY: misc_structure
<222> LOCATION: (1)..(49)
<223> OTHER INFORMATION: F Primer

<400> SEQUENCE: 20
taatacgact cactataggg agaccacaca agaccaagtg gacgatatg            49

<210> SEQ ID NO 21
<211> LENGTH: 48
<212> TYPE: DNA
<213> ORGANISM: Artificial Sequence
<220> FEATURE:
<221> NAME/KEY: misc_structure
<222> LOCATION: (1)..(48)
<223> OTHER INFORMATION: R Primer

<400> SEQUENCE: 21
taatacgact cactataggg agaccacaat ttgcaagcaa tctgtgac             48

<210> SEQ ID NO 22
<211> LENGTH: 27
<212> TYPE: DNA
<213> ORGANISM: Artificial Sequence
<220> FEATURE:
<221> NAME/KEY: misc_structure
<222> LOCATION: (1)..(27)
<223> OTHER INFORMATION: T7 Promoter

<400> SEQUENCE: 22
taatacgact cactataggg agaccac                                    27
```